United States Patent [19]

Gubin et al.

[11] Patent Number: 4,957,925

[45] Date of Patent: Sep. 18, 1990

[54] AMINOALKOXYPHENYL DERIVATIVES, PROCESS OF PREPARATION AND COMPOSITIONS CONTAINING THE SAME

[75] Inventors: Jean Gubin; Pierre Chatelain, both of Brussels; Marcel Descamps, Wavre, all of Belgium; Dino Nisato, Saint Georges D'Orques, France; Henri Inion, Wemmel, Belgium; Jean Lucchetti, Chastre, Belgium; Jean-Marie Mahaux, Brussels, Belgium; Jean-Noël Vallat, Toulouse, France

[73] Assignee: Sanofi, Paris, France

[21] Appl. No.: 82,554

[22] Filed: Aug. 7, 1987

Related U.S. Application Data

[63] Continuation-in-part of Ser. No. 6,233, Jan. 23, 1987, abandoned.

[30] Foreign Application Priority Data

Feb. 14, 1986 [FR] France ................. 86 02045

[51] Int. Cl.$^5$ ............... C07D 487/04; C07D 237/28; A61K 31/435; A61K 31/50
[52] U.S. Cl. .................... 514/299; 514/253; 514/233.2; 544/127; 544/362; 546/121; 546/183; 546/153; 546/300; 548/329; 549/466; 549/479
[58] Field of Search ............... 546/183; 514/299, 228, 514/232, 253; 544/127, 362

[56] References Cited

U.S. PATENT DOCUMENTS

| 3,947,470 | 3/1976 | Brenner | 549/57 |
| 4,013,012 | 7/1978 | Gubin | 544/127 |
| 4,117,128 | 9/1978 | Brenner | 549/146 |

FOREIGN PATENT DOCUMENTS 2341578  1/1978  France.

*Primary Examiner*—Mark L. Berch
*Attorney, Agent, or Firm*—Bacon & Thomas

[57] ABSTRACT

An aminoalkoxyphenyl compound of formula

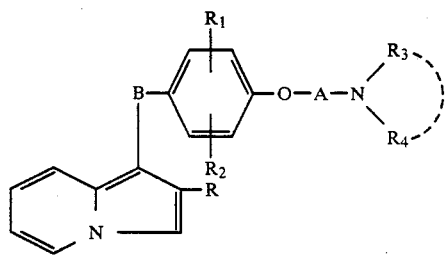

as well as a pharmaceutically acceptable salt of this compound.

28 Claims, No Drawings

AMINOALKOXYPHENYL DERIVATIVES, PROCESS OF PREPARATION AND COMPOSITIONS CONTAINING THE SAME

This application is a continuation-in-part of copending application Ser. No. 006,233, filed Jan. 23, 1987 now abandoned.

The present invention relates to new carbocyclic or heterocyclic derivative and to a process for preparing them.

More particularly, the invention relates to the novel aminoalkoxy-phenyl derivatives represented by the general formula:

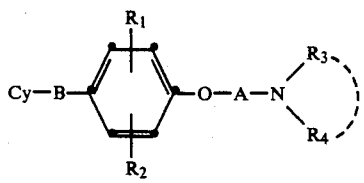

I in which:

B represents a —S—, —SO— or —SO$_2$— group,

R$_1$ and R$_2$, which are identical or different, each denote hydrogen, a methyl or ethyl radical or a halogen such as chlorine, bromine or iodine, A denotes a straight- or branched-alkylene radical having from 2 to 5 carbon atoms or a 2-hydroxypropylene radical in which the hydroxy is optionally substituted by a lower alkyl radical, R$_3$ denotes an alkyl radical or a radical of formula —Alk—R$_5$ in which Alk denotes a single bond or a linear- or branched-alkylene radical having from 1 to 5 carbon atoms and R$_5$ denotes a pyridyl, phenyl, 2,3-methylenedioxyphenyl or 3,4-methylenedioxypehnyl radical or a phenyl group substituted with one or more substituents, which may be identical or different, selected from halogen atoms, lower alkyl groups or lower alkoxy groups, R$_4$ denotes hydrogen or an alkyl radical, or R$_3$ and R$_4$ when taken together, denote an alkylene or alkenylene radical having from 3 to 6 carbona toms and optionally substituted with a phenyl radical or optionally interrupted by

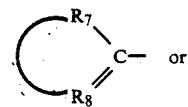

R$_6$ denoting hydrogen or a lower alkyl or phenyl radical,

Cy represents a group of formula:

(D)

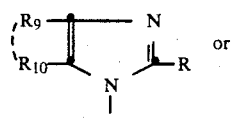

(E)

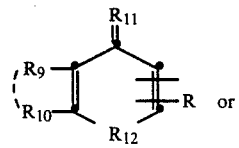

(F)

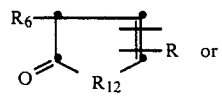

(G)

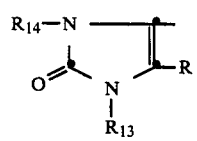

(H)

R represents hydrogen, an alkyl radical, a cycloalkyl radical, a benzyl radical or a phenyl radical optionally substituted with one or more substituents, which may be identical or different, selected from halogen atoms, for example fluorine, chlorine, bromine atoms and from lower alkyl, lower alkoxy or nitro groups, R$_7$ and R$_8$ are taken together with the carbon atom to which they are attached to form:

an optionally aromatic mono- or di-cyclic carbocyclic group having from 5 to 10 carbon atoms and optionally substituted by a R group in the α-position with respect to the methyne group, an optionally aromatic 5-membered heterocyclic group, the heteroatoms or heterogroups being selected from the groups O, S, N, —N—R$_6$; O and N; O and —N—R$_6$;

S and N; S and —N—R$_6$; N and N; N and —N—R$_6$, the heterocyclic group being optionally substituted by a R group in the α-position with respect to the methyne group and optionally substituted by one or two groups selected from lower alkyl and phenyl groups, an optionally aromatic 6- to 10-membered mono- or di-cyclic heterocyclic group, the heteroatoms or heterogroups being selected from the groups O, S, N, —N—R$_6$; O and N; O and —N—R$_6$;

S and N; S and —N—R$_6$; N and N; N and —N—R$_6$, the heterocyclic group being optionally substituted by a R group in the α-position with respect to the methyne group, R$_9$ and R$_{10}$, which are the same or different, each represent hydrogen, a lower alkyl radical or a phenyl radical or when they are taken together with the carbon atoms to which they are attached represent an optionally aromatic 6-membered carbocyclic ring, $R_{11}$ represents oxygen or sulphur $R_{12}$ represents oxygen, sulphur or a group

$R_{13}$ and $R_{14}$, which are identical or different, each represent hydrogen, a lower alkyl radical or a Benzoyl radical with the proviso that when Cy represents a benzo[b]furyl or benzo[b]

thienyl group and B represents a —SO$_2$— group, $R_3$ represents a radical —Alk—$R_5$.

In the present context, both in the description and in the claims, the following meaning attaches to the terms stated above:

"alkyl" denotes straight- or branched-saturated aliphatic hydrocarbon residues having up to 8 carbon atoms, such as methyl, ethyl, n-propyl, isopropyl, n-butyl, isobutyl, tert-butyl, n-pentyl, neopentyl, n-hexyl, n-heptyl or n-octyl, "lower alkyl" denotes saturated aliphatic hydrocarbon residues having up to 4 carbon atoms, such as methyl, ethyl, n-propyl, isopropyl, n-butyl, iso-butyl, tert-butyl or 1-methylpropyl, "lower alkoxy" denotes a hydroxy group substituted with a lower alkyl group as defined above, "cycloalkyl" denotes an alicyclic ring having from 3 to 6 carbon atoms.

Thus, taking into account the meanings given above:

R can denote, in particular, a methyl, ethyl, n-propyl, isopropyl n-butyl, isobutyl, tert-butyl, 1-methylpropyl, n-pentyl, neopentyl, phenyl, monofluoro-, monochloro- or monobromophenyl, difluoro-, dichloro- or dibromophenyl, monomethyl- or dimethylphenyl, or monomethoxy- or dimethoxyphenyl radical, a methylphenyl radical substituted with a halogen atom or a cyclopropyl radical, A can denote, in particular, a 1,2-ethylene, 1,3-propylene, 2-methyl-3-propylene, 1,4-tetramethylene or 1,5-pentamethylene chain, $R_3$ can denote, in particular, a methyl, ethyl, n-propyl, isopropyl, n-butyl, isobutyl, tert-butyl, 1-methyl-propyl, n-pentyl, n-hexyl, n-heptyl n-octyl, phenyl, benzyl or phenethyl radical, a methoxyphenyl or a dimethoxyphenethyl, for example 3,4-dimethoxyphenethyl radical, a dimethylphenethyl, dimethoxyphenyl, dimethoxybenzyl or pyridylethyl radical or a phenethyl radical substituted in the aromatic portion, with methyl and methoxy radicals, $R_4$ can denote, in particular, a methyl, ethyl, n-propyl, isopropyl, n-butyl isobutyl, tert-butyl, n-pentyl, neopentyl, n-hexyl, n-heptyl or n-octyl radical, $R_3$ and $R_4$, taken together, can denote, in particular, a 1,4-tetramethylene 1,5-pentamethylene, 3-oxo-1,5-pentamethylene, 3-aza-1,5-pentamethylene, 3-methyl-aza-1,5-pentamethylene, 3-phenylaza-1,5-pentamethylene or —CH=CH—N=CH— radical, so that $R_3$ and $R_4$, taken with the nitrogen atom to which they are attached, can denote, in particular, pyrrolidinyl, piperidyl, morpholinyl, piperazinyl, 4-methylpiperazinyl, 4-phenylpiperazinyl or 1H-imidazolyl radical.

Cy can denote, in particular, a phenyl, cyclohexenyl, indenyl, naphthyl, dihydronaphthyl, pyridyl, dihydropyridyl, furyl, dihydrofuryl, thienyl, dihydrothienyl, pyrrolyl, dihydropyrrolyl, pyrazolyl, imidazolyl, pyrimidyl, pyrazinyl, pyridazinyl, oxazolyl, isoxazolyl, thiazolyl, benzofuryl, benzothienyl, indolyl, benzimidazolyl, benzoxazolyl, quinolinyl, benzisoxazolyl, cinnolinyl, quinoxalinyl, quinazolinyl, indolizinyl, thienopyridyl, tetrahydrothienopyridyl, pyrrolopyridyl, pyrazolopyridyl, pyrrolopyridazinyl, imidazopyridyl, dihydrofuranonyl, imidazolinonyl, chromonyl.

A particularly valuable class of compounds of formula I are those in which Cy represents an indolizinyl group.

A preferred class of compounds of formula I are those in which Cy represents an indolizin-1-yl group.

Another class of compounds of formula I are those in which $R_3$ represents a group of formula —Alk—$R_5$.

Particularly useful compounds of formula I are those in which the chain

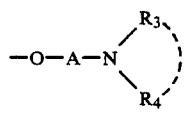

represents a [N-methyl-N-(3,4-dimethoxy-β8-phenethyl)amino]propyloxy group.

Other valuable compounds of formula I are those in which R represents an isopropyl or cyclopropyl group.

The invention also relates to the pharmaceutically acceptable salts of the compounds of formula I formed with an organic or inorganic acid.

As examples of organic salts of this type, there may be mentioned the oxalate, maleate, fumarate, methanesulphonate, benzoate, ascorbate, pamoate, succinate, hexamate, bismethylenesalicylate, ethanedisulphonate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulphonate and theophyllineacetate, as well as the salts formed with an amino acid such as the lysine or histidine salt.

As examples or inorganic salts of this type, the hydrochloride, hypobromide, sulphate, sulphamate, phosphate and nitrate may be mentioned.

Another object of the invention relates to the N-oxide derivatives of the compounds of formula I.

The compounds of formula I can exist, in some cases, in the form of optical isomers, in particular as a result of the asymmetric carbon present when A represents a 2-hydroxypropylene chain.

The invention relates, at the same time, to all the isomers of the compounds of formula I, the isomers being considered in the dextrorotatory or laevorotatory form, or in the form of a mixture, for example in the form of a racemic mixture.

It has been found that the aminoalkoxyphenyl derivatives of the invention possess exceptional pharmacological properties, especially calcium transport inhibitory properties, as well as bradycardic, hypotensive and antiadrenergic properties.

From this viewpoint, the preferred compounds of the invention are those in which B represents a —SO$_2$— group.

These properties are capable of making the compounds in question very useful on the treatment of certain pathological syndromes of the cardiovascular system, especially in the treatment of angina pectoris, hypertension, arrhythmia and cerebral circulatory insufficiency.

In the antitumour field, the compounds of the invention may be useful as potentiators of anticancer drugs.

Consequently, the invention also relates to pharmaceutical or veterinary compositions containing, as active principle, at least one aminoalkoxyphenyl derivative of formula I or a pharmaceutically acceptable salt of this derivative, or an N-oxide derivative thereof, in combination with a pharmaceutical vehicle or a suitable excipient.

Another object of the invention relates to a method for treating pathological syndromes of the cardiovascular system especially angina pectoris, hypertension, arrhythmia and cerebral vascular insufficiency in a host in need of such treatment comprising the administration to this host of an effective dose of an aminoalkoxyphenyl derivative of the invention.

Depending on the administration route selected, the daily dosage for a human being weighing 60 kg will be between 2 and 500 mg of active principle.

The compounds of formula I can be obtained:

I. When B represents a —S— or —$SO_2$— group and A represents an alkylene radical, by condensing, in the presence of an acid acceptor and in a polar solvent such as dimethylsulphoxide or an alcohol, for example butanol, or a ketone such as methyl ethyl ketone, or a nonpolar solvent such as an aromatic hydrocarbon, for emample benzene, toluene or xylene, a 4-alkoxyphenyl derivative of general formula:

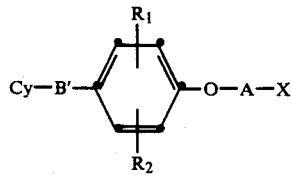
II in which B' represents a —S— or —$SO_2$— group, Cy, $R_1$ and $R_2$ have the same meaning as above, A represents an alkylene radical as defined in the formula I and X represents a halogen atom, preferably bromine, or an alkylsulphonyloxy group having from 1 to 4 carbon atoms such as for example, methanesulphonyloxy, or an arylsulphonyloxy group having from 6 to 10 carbon atoms, such as benzenesulphonyloxy or p-tolunesulphonyloxy, with an amine of general formula:

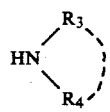
III in which $R_3$ and $R_4$ have the same meaning as above to form the desired aminoalkoxyphenyl derivative of formula I in the form of a free base.

In general, the condensation in question is performed at a temperature between room-temperature and the refluxing-temperature of the medium, the acid acceptor being, for example, an alkali metal carbonate or hydroxide or an excess of amine of formula III.

The compounds of formula II in question can be obtained: (a) when X is a halogen, by condensation of a 4-hydroxyphenyl derivative of general formula:

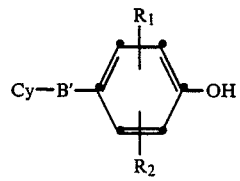
IV in which Cy, B', $R_1$ and $R_2$ have the same meaning as above, with a dihaloalkane of general formula Hal—A—Hal  V in which A denotes an alkylene radical as defined in the formula I and Hal denotes a halogen atom, preferably bromine, this reaction being performed under reflux in a solvent such as methyl ethyl ketone or N,N-dimethylformamide and in the presence of a basic agent such as an alkali metal carbonate, for example potassium carbonate, an alkali metal hydride such as sodium hydride, an alkali metal hydroxide, for example sodium or potassium hydroxide, or an alkali metal alcoholate, for example sodium methylate or ethylate, (b) when X denotes an alkylsulphonyloxy or arylsulphonyloxy group, by condensation of a halide of general formula:

Hal—W in which Hal has the same meaning as above and W denotes an alkylsulphonyl radical having from 1 to 4 carbon atoms, for example methanesulphonyl, or an arylsulphonyl radical having from 6 to 10 carbon atoms, for example benzenesulphonyl or p-toluenesulphonyl, in a solvent which is an acid acceptor, for example pyridine, with a 4-hydroxyalkoxy derivative of general formula:

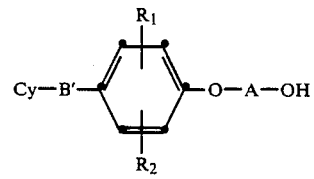
VI

Cy, B', $R_1$ and $R_2$ have the same meaning as above and A denotes an alkylene radical as defined in formula I.

As regards the compounds of formula VI, these can be prepared by condensing, in a suitable solvent such as N,N-dimethylformamide and in the presence of a basic agent such as an alkali metal carbonate, for example potassium carbonate, an alkali metal hydroxide such as sodium or potassium hydroxide, an alkali metal hydride such as sodium hydride or an alkali metal alcoholate, for example sodium methylate or ethylate, a 4- hydroxyphenyl derivative of formula IV above with a halogenated alcohol of general formula:

Hal—A—OH  VII in which A denotes an alkylene radical as defined in the formula I and Hal has the same meaning as above.

Compounds of formula IV are known products, for instance those compounds in which Cy represents a benzofuryl or benzothienyl group and B' represents a —SO$_2$— group. These compounds are disclosed in U.S. Pat. No. 4,117,128.

The other compounds of formula IV can be prepared in a general procedure, by adapting to the desired compound the method described in the aforesaid U.S. patent or the methods described hereunder.

In most cases, those compounds of formula IV can be obtained by fixing a 4-O-protected benznesulphonyl or phenylthio chain to the required carbocycle or heterocycle using a Friedel-Crafts reaction and deprotecting the oxygen in the 4-position of the benzenesulphonyl or phenylthio group by means of classical procedures to regenerate the OH group.

Hereunder are examples of methods commonly used for preparing derivatives of formula IV:

(a) Compounds of formula IV in which Cy represents a group (D) The compounds of formula IV in which Cy represents a 2-R-indolizin-1-yl group can be prepared from a compound of general formula:

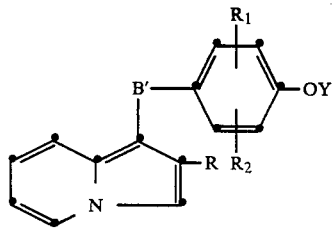

in which B', R, R$_1$ and R$_2$ have the same meaning as above and Y denotes an alkylsulphonyl radical having from 1 to 4 carbon atoms, for example methanesulphonyl, an arylsulphonyl radical having from 6 to 10 carbon atoms, for example benzenesulphonyl or p-toluenesul-Phonyl,analkanoyl radical having from 1 to 4 carbon atoms, for example acetyl or Y represents a benzyl or a methyl radical, namely:

by hydrolysis, under reflux and in basic medium when an alkylsulphonyl, arylsulphonyl or alkanoyl radical, by hydrogenation using an appropriate catalyst for instance palladium charcoal when Y represents a benzyl radical, by demethylation using an appropriate agent such as pyridine 20 hydrochloride at 180°–220° C. or aqueous hydrobromic acid when Y represents a methyl radical.

As regards the compounds of formula VIII, these can be prepared by cyclization under reflux of a picolyl sulphone or sulphide of general formula:

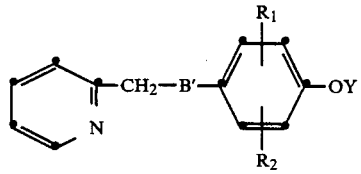

in which B', R$_1$, R$_2$ and Y have the same meaning as above, with an α-haloketone of general formula:

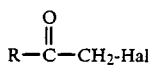

in which R and Hal have the same meaning as above, this being performed in a solvent such as methyl ethyl ketone and in the presence of a basic agent such as an alkali metal carbonate for example potassium carbonate or an alkali metal bicarbonate for example sodium bicarbonate.

As regards the picolyl sulphones of formula IX, these are obtained by reaction of 2-(chloromethyl)-pyridine of formula:

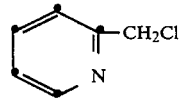

with an alkali metal 4-(alkylsulphonyloxy)- or 4-(arylsulphinyloxy)benzenesulphinate derivative for example sodium 4-(p-toluenesulphonyloxy)benzenesulphinate according to the process described in J. Chem. Soc. 1965 p. 3090. The derivative of formula XI is a product which is known and which can be prepared by known methods.

As an alternative procedure the compounds of formula IV in which Cy represents a 2-R-indolizin-1-yl group and B' represents a —S— group can be directly obtained from a picolyl sulphide of general formula:

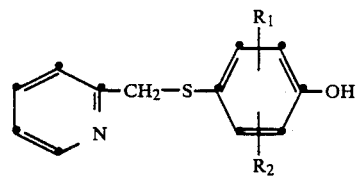

in which R$_1$ and R$_2$ have the same meaning as above, by reacting with a α-haloketone of formula X and cyclising the pyridinium salt so obtained under reflux in a solvent such as water and in the presence of a basic agent such as an alkali metal carbonate for example potassium carbonate or an alkali metal bicarbonate for example sodium bicarbonate.

The compounds of formula XII are known compounds having been published in J. Med. Chem. 26, 218 (1983) or compounds which can be prepared by known procedures and those of formula IX in which B' represents a —S— group can be obtained from the compounds of formula XII by reaction with an alkylsulphonyl or arylsulphonyl halide.

(2) The compounds of formula IV in which Cy represents a 2-R-indolizin-3-yl group can be prepared by reacting an indolizine derivative of general formula:

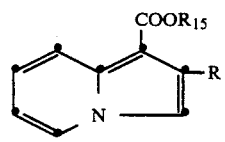

in which R has the same meaning as above and R$_{15}$ represents a lower alkyl radical preferably ethyl, with a halide of general formula:

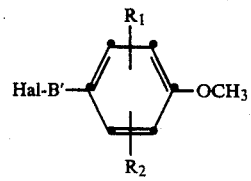

in which B', R₁, R₂ and Hal have the same meaning as above and in the presence of a Friedel-Crafts catalyst such as aluminium chloride to provide a compound of general formula:

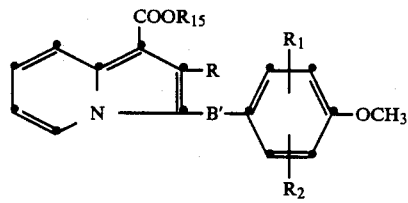

in which B', R, R₁, R₂ and R₁₅ have the same meaning as above.

The compound of formula XV is subsequently demethylated using an ethanethiol/aluminum chloride mixture to give a 4-methoxyphenyl derivative of general formula:

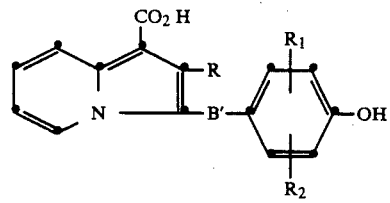

in which B', R, R₁ and R₂ have the same meaning as above which, when heated to about 200° C. provides the required compound of formula IV.

The compounds of formula XIII are either known compounds having been published in J. Chem. Soc. 1962 pp. 2627–2629 or compounds which can be prepared in accordance with the method described therein.

(3) The compounds of formula IV in which Cy represents a 2-R-imidazo[1,2a]pyrid-3-yl group can be prepared from a 2-R-imidazo[!,2-a]pyridine with a halide of formula XIV and in the presence of a Friedel-Crafts catalyst such as aluminium chloride to provide a compound of general formula:

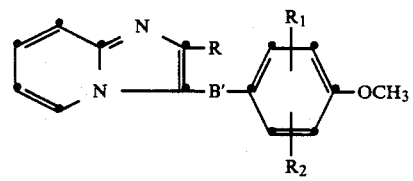

in which B', R, R₁ and R₂ have the same meaning as above.

The compound of formula XVII is subsequently demethylated using an appropriate agent for instance hydrobromic acid or an ethanethiol/ aluminium chloride mixture to.give the required compound of formula IV.

2-Aryl-imidazo[1,2-a]pyridines are known from J. Med. Chem. 8, p. 305 (1965). The other 2-R-imidazo[!,2-a]pyridines can be obtained in accordance with the method described in the aforesaid reference or using classical procedures.

(4) The compounds of formula IV in which Cy represents a pyridyl or 3-R-4-pyridyl group can be obtained by demethylating with an appropriate agent such as aqueous hydrobromic acid, a 4-methoxyphenyl derivative of general formula:

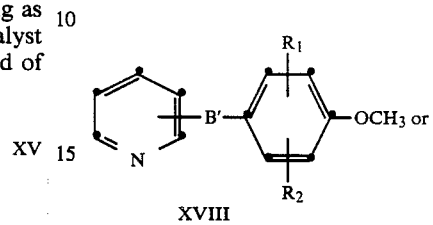

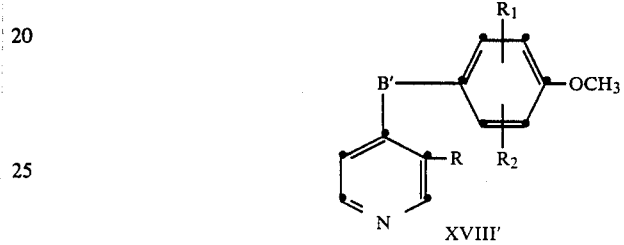

in which B', R₁ and R₂ have the same meaning as above and R has the same meaning as above with the exception of hydrogen, to provide the required compounds of formula IV.

The compounds offormulae XVIII and XVIII' in which B' represents group can be prepared by oxidizing a sulfide derivative of general formula:

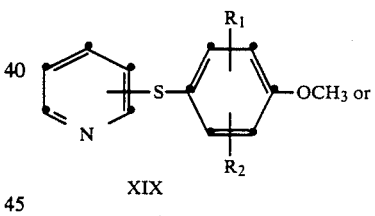

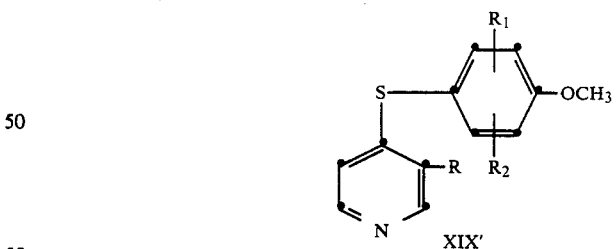

in which R₁ and R₂ have the same meaning as above and R has the same meansing as in formula XVIII or XVIIIl.

Compounds of formula XIX are known having been described in U.S. Pat. No. 4,128,552. The other compounds of formula XIX can be obtained in accordance with the method described in the aforesaid U.S. patent while those compounds of formula XIX' can be prepared from a 3-R-pyridine, in which R is other than hydrogen, by oxidation with hydrogen peroxide in acetic acid to provide the corresponding 3-R-pyridine-N-oxide which when reacted with a nitric acid/sulphuric acid mixture gives rise to the corresponding 3-R-4-nitro-pyridine-N-oxide.

This nitro derivative is then reacted first with acetyl bromide, then with iron powder in acetic acid to give the corresponding 3-R-4-bromo-pyridine which, when treated with a thiophenol derivative of general formula:

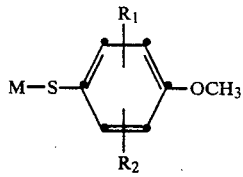

XX in which $R_1$ and $R_2$ have the same meaning as above and M represents an alkali metal atom such as sodium, provides the required compound of formula XIX'.

(5) The compounds of formula IV in which Cy represents a 2-R-quinolin-3-yl group can be prepared by reacting an α-haloketone of formula X with a metal derivative of general formula:

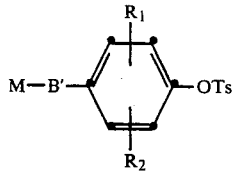

XXI in which M, B', $R_1$ and $R_2$ have the same meaning as above and Ts represents a p-toluenesulphonyl group, to provide a ketone of general formula:

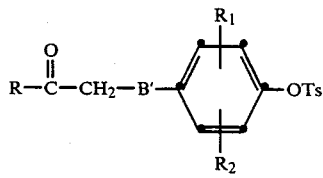

XXII in which B', R, $R_1$, $R_2$ and Ts have the same meaning as above. This ketone of formula XXII when treated with 2-amino-benzaldehyde [Helv Chem. Act. vol. XVIII, p. 1235 (1935)] gives the 4-methoxyphenyl derivative of general formula:

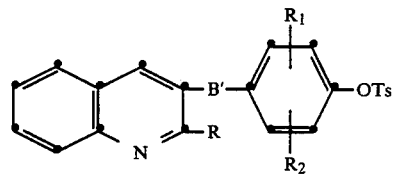

XXIII in which B', R, $R_1$, $R_2$ and Ts have the same meaning as above, which is subsequently hydrolysed in basic medium for instance in aqueous alkali metal hydroxide, to provide the required compound of formula IV.

(6) The compounds of formula IV in which Cy represents a 3-R-cinnolin-4-yl or 4-R-cinnolin-3-yl group can be obtained by reacting a 3-R-4-halogenocinnoline (J. Chem. Soc. 1953, p. 609) with a thiophenol derivative of general formula:

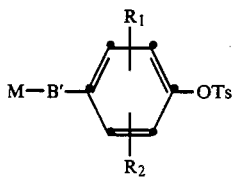

XXIV in which M, $R_1$, $R_2$ and Ts have the same meaning as above and B' represents in which formula: a —S— group to provide the 4-tosyloxyphenyl derivative of general

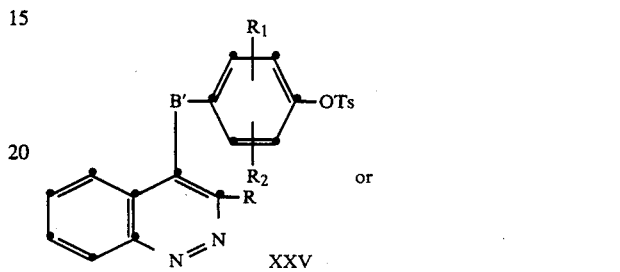

or

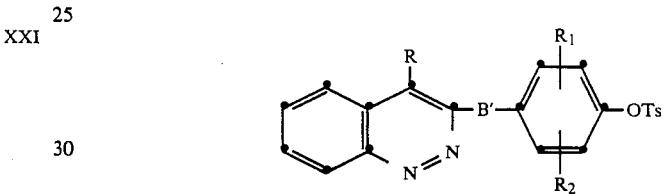

XXV' in which R, $R_1$, $R_2$ and Ts have the same meaning as above and B' represents a —S— group.

The 4-tosyloxyphenyl derivative of formula XXV or XXV' is subsequent hydrolysed in basic medium for instance in aqueous alkali metal hydroxide to give the required compound of formula IV in which B' represents a —S— group.

Compounds of formula XXIV in which —OTs is replaced by —OCH3 can also be used. In such case the corresponding compound of formula XXV or XXV' is demethylated using for instance hydrobromic acid.

The sulphide derivative of formula XXV or XXV' when oxidized with a suitable agent such as hydrogen peroxide in acetic acid or potassium permanganate, provides the compound of formula XXV or XXV' in which B' represents a —SO$_2$— group, which compound after hydrogenation on a required compounds of formula IV in which B' represents a —SO$_2$— group.

Alternatively the compounds of formula IV in question in which B' represents a —SO$_2$— group can be obtained from a 3-R-4- halogenocinnoline or a 4-R-3-halogeno-cinnoline by reacting with a benzenesulphonyl derivative of general formual XXIV in which B' represents a —SO$_2$— group to obtain a compound of formula XXV or XXV' in which B' represetns a —SO$_2$— group which is detosylated as described above to provide the required compound of formula IV.

(7) The compounds of formula IV in which Cy represents a 6-R-pyrrolo[1,2-b]pyridazin-5-yl group can be prepared by reacting a 3- halogenomethylpyridazine with a metal derivative of formula XXI to provide a pyridazine derivative of general formula:

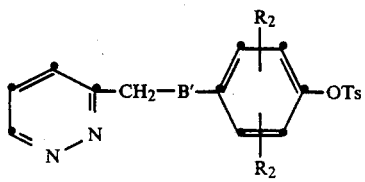

XXVI in which B', R₁, R₂ and Ts have the same meaning as above, which is subsequently reacted with an α-haloketone of formula X in the presence of a non-nucleophilic base such as for example 1,8-diazabicyclo[5,4,0] undec-7ene to give the pyrrolo[1,2-b]pyridazine derivative of general formula:

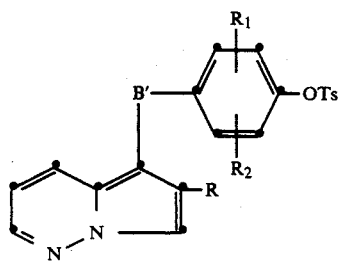

XXVII in which B', R, R₁, R₂ and Ts have the same meansing as above.

The tosyl derivative of formula XXVII is then hydrolysed in a basic medium for instance aqueous alkali metal hydroxide, to provide the required compound of formula IV.

3-Chloromethyl-pyridazine is a known compound having been published in Khim. Geterot. Sikl. Soedin. 3, pp. 412–414 (1970).

(8) The compounds of formula IV in which Cy represents a 2-R-pyrazolo 5-a]pyrid-1-yl group can be prepared, in accordance with the method described in European patent application No. 121,197, by treating a 2-R-pyrazolo[1,5-a]pyridine with a halide of formula XIV in the 5. presence of a Friedel-Crafts catalyst such as for example aluminium chloride, to provide the 4-methoxyphenyl derivative of general formula:

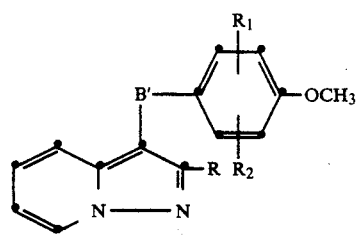

XXVIII in which B', R, R₁ and R₂ have the same meaning as above.

The pyrrolopyridine derivative of formula XXVIII is then demethylated for instance by using pyridine hydrochloride at 200°–220° C. to provide the required compound of formula IV.

(9) The compounds of formula IV in which Cy represents a phenyl group can be prepared by reacting benzene with a halide of formula XIV in the presence of a Friedel-Crafts catalyst such as aluminium chloride, to provide the required compound of formula IV.

(10) The compounds of formula IV in which Cy represents a 2-R-phenyl group or a 1-R-2-naphthyl group can be prepared by treating a halide of general formula:

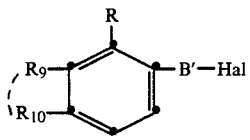

XXIX in which B', R and Hal have the same meaning as above and R₉ and R₁₀ each represent hydrogen or are taken together with the carbon atom to which they are attached to form a phenyl group, with a methoxyphenyl derivative of general formula:

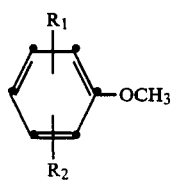

XXX in which R₁ and R₂ have the same meaning as above, in the presence of a Friedel-Crafts catalyst such as aluminium chloride, to obtain the compounds of general formula:

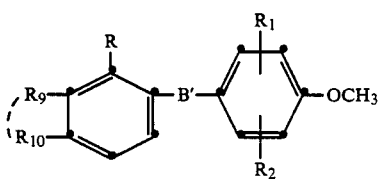

XXXI in which B', R, R₁ and R₂ have the same meaning as above and R₉ and R₁₀ have the same meaning as in formula XXIX.

The compounds of formula XXXI are then demethylated using for instance aqueous iodhydric acid to provide the required compound of formula IV.

Compounds of formula XXIX are known products having been described in C.A. 81, 63285 g, or can be obtained in accordance with known procedures.

(11) The compounds of formula IV in which Cy represents an optionally monoor di-substituted 2-R-4,5-dihydro-furan-3-yl group can be prepared by heating a ketone derivative of formula XXII with a 1,2-dihalogenoethane of general formula:

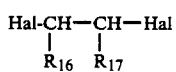

XXXII in which R₁₆ and R₁₇, which are the same or different, each represent hydrogen, a lower alkyl radical or a phenyl radical, in the presence of a basic agent such as an alkali metal carbonate, to obtain a cyclopropane derivative of general formula:

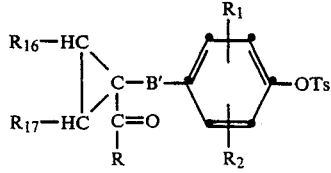

in which B', R, R$_1$, R$_2$, R$_{16}$, R$_{17}$ and Ts have the same meaning as above.

The cyclopropane derivative of formula XXXIII is subsequently heated between 100 and 130° C. in the presence of a phase transfer catalyst such as for instance triphenylphosphine or tricaprylylmethyl ammonium chloride to provide a 4-tosyloxyphenyl derivative of general formula:

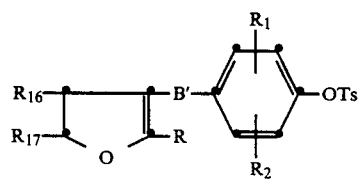

in which B', R, R$_1$, R$_2$, R$_{16}$, R$_{17}$ and Ts have the same meaning as above and the said 4-tosyloxyphenyl derivative is then detosylated by treatment with a basic agent such as an alkali metal hydroxide, to provide the required compound of formula IV.

(12) The compounds of formula IV in which Cy represents an optionally mono- or di- substituted 2-R-furan-3-yl group can be obtained by oxidizing for instance with manganese oxide, a 4,5-dihydrofuran derivative of formula XXXIV to obtain a furan derivative of general formula:

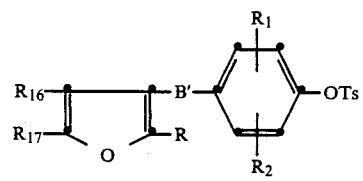

in which B', R, R$_1$, R$_2$, R$_{16}$, R$_{17}$ and Ts have the same meaning as above, which furan derivative is subsequently treated with a basic agent such as an alkali metal hydroxide, to obtain the required compound of formula IV.

(13) The compounds of formula IV in which Cy represents a 2-R-furan-3-yl or 2-R-thien-3-yl or 2-R-pyrrol-3-yl group can be prepared by reacting a compound of general formula:

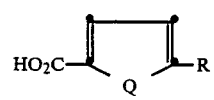

in which R has the same measning as above and Q represents —O, —S or

with a halide of formula XIV and in the presence of a Friedel-Crafts catalyst such as aluminium chloride to obtain a 4-methoxy derivative of general formula:

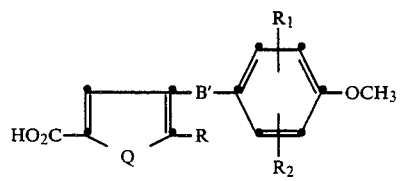

in which B', R, R$_1$, R$_2$ and Q have the same meaning as above, which is subsequently decarboxylated by heating and demethylated with an appropriate agent such as pyridine hydrochloride or aqueous hydrobromic acid, to provide the required compound of formula IV.

Alternatively, the compounds of formula IV in which Cy represents an optionally substituted 2-R-furan-3-yl group can be prepared by oxidizing, for instance with manganese oxide, a 4-tosyloxyphenyl derivative of formula XXXIV to obtain an optionally substituted 2-R-3-(4-tosyloxybenzenesulphonyl)furan derivative which is subsequently treated by a basic medium for instance an alkali metal hydroxide, to provide the required compound of formula IV.

(14) The compound of formula IV in which Cy represents a 1-R-imidazol-2yl or 1-R-benzimidazol-2-yl group can be obtained by reacting a 1-R-imidazole or 1-R-benzimidazole with a halide of formula XIV in the presence of a Friedel-Crafts catalyst such as aluminium chloride, to obtain a compound of general formula:

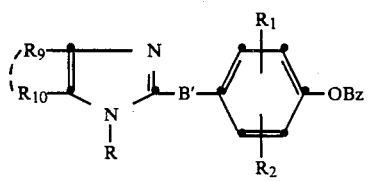

in which B', R, R$_1$ and R$_2$ have the same meaning as above, R$_9$ and R$_{10}$ each represent hydrogen or are taken together with the carbon atoms to which they are attached to form a phenyl group and Bz represents a benzyl group, which is subsequently debenzylated using for instance palladium charcoal to obtain the required compound of formula IV.

When R represents hydrogen, imidazole or benzimidazole is protected in the 1-position with an appropriate N-protecting group for instance a benzyl group which can subsequently be removed, if desired, using classical procedures.

The compounds of formula IV in which Cy represents an optionally substituted 5-R-isoxazol-4-yl derivative can be prepared by reacting an isoxazole derivative of general formula:

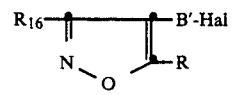

in which B', R, R$_{16}$ and Hal have the same meansing as above wtih a 4-methoxy derivative of formula XXX in the presence of a Friedel-Crafts catalyst such as aluminium chloride to obtain the compounds of general formula:

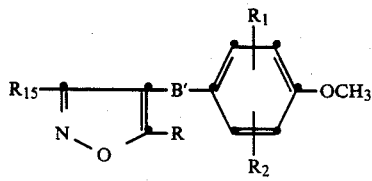

XXXX in which B', R, R₁, R₂ and R₁₆ have the same meaning as above, which is optionally demethylated, to provide the required compound of formula IV.

Compounds of formula XXXIX are known products having been described in Gazz. Chim. Ital. 76, 30 (1946) while the other compounds of formula XXXIX can be obtained in accordance with the method described therein or classical methods.

(16) The compounds of formula IV in which B' represents a —SO₂— group and Cy represents a group of formula (D) in which R₇ and R₈ are taken together with the carbon atom to which they are attached to form a non aromatic mono- or di-cyclic carbocyclic group having from 5 to 10 carbon atoms and optionally substituted by a R group in the α-position with respect to the methyne group, for instance a 3-R-inden-yl, 2-R-cyclohexen-1-yl or 1-R-3,4-dihydro-naphth-2-yl group can be prepared, in accordance with the method described in J. Org. Chem., vol. 35, No. 12, pp. 4217–4222 (1970) by heating a compound of general formula:

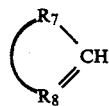

XXXXI in which R₇ and R₈ are taken together with the carbon atom to which they are attached to form a group having from 5 to 10 carbon atoms and optionally substituted by a R group in the α-position with respect to the methyne group, with a halide of formula XIV in an appropriate solvent such as benzene and in the presence of anhydrous cupric chloride and triethylamine, to obtain a 4-tosyloxyphenyl derivative of general formula:

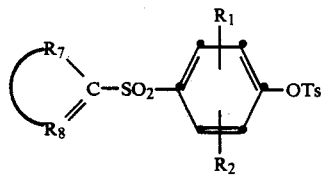

XXXXII in which R₁, R₂ and Ts have the same meaning as above and R₇ and R₈ have the same meaning as in formula XXXXI which is then detosylated using an appropriate agent such as an alkali metal hydroxide to obtain the required compound of formula IV.

(b) Compounds of formula IV in which Cy represents a group (E). The compounds of formula IV in which Cy represents a 2-R-imidazol-1yl or 2-R-benzimidazol-1-yl group can be obtained by reacting a 2-R-imidazole or 2-R-benzimidazole with a halide of formula XIV in the presence of a Friedel-Crafts catalyst such as aluminium chloride, to provide a compound of general formula:

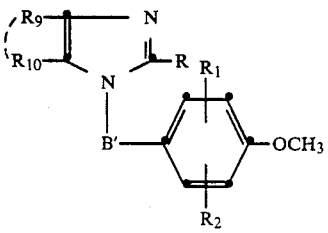

XXXXIII in which B', R, R₁ and R₂ have the same meaning as above and R₉ and R₁₀ each represent hydrogen or are taken together with the carbon atoms to which they are attached to form a phenyl group.

The compound of formula XXXXIII is then demethylated using an appropriate agent for instance an ethanethiol/aluminium chloride mixture to give the required compound of formula IV.

(c) Compounds of formula IV in which Cy represents a group (F)

The compounds of formula IV in which Cy represents for instance a 2-R-chromon-3-yl group and B' represents a —SO₂— group can be prepared by reacting a 2-R-3-halogeno-chromone with a 4-methoxy derivative of formula XIV in which B' represents a —SO₂— group, in the presence of a Friedel-Crafts catalyst such as aluminium chloride, to obtain the chromone derivative of general formula:

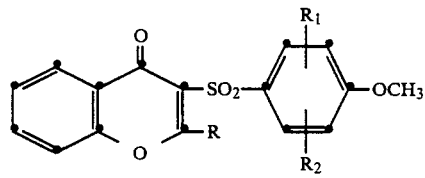

XXXXIV in which R, R₁ and R₂ have the same meaning as above, which is optionally demethylated using for instance aqueous hydrobromic acid or pyridine hydrochloride, to provide the required compound of formula IV.

(d) Compounds of formula IV in which Cy represents a group (G)

The compounds of formula IV in which Cy represents an optionally substituted 5-R-2,3-dihydro-furan-2-one-4-yl can be prepared by reacting, in basic medium, for instance potassium carbonate, a ketone of formula XXII with a 2-halogenoacetate of general formula:

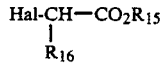

XXXXV in which Hal, R₁₅ and R₁₆ have the same meaning as above, to obtain a ketoester which is first hydrolysed in basic medium and then treated with a strong acid to provide the carboxylic acid derivative of general formula:

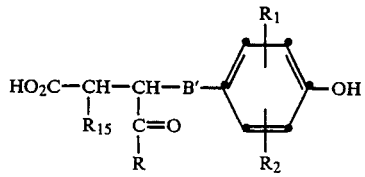

in which B', R, $R_1$, $R_2$ and $R_{16}$ have the same meaning as above.

The acid of formula XXXXVI when treated with trifluoroacetic acid or thionyl chloride provides the required compound of formula IV.

(e) Compounds of formula IV in which Cy represents a group (H)

The compounds of formula IV in which Cy represents an optionally substituted 5-R-1,3-dihydro-2H-imidazol-2-one-4-yl can be obtained by reacting a 5-R-imidazol-2-one with a halide of formula XIV to obtain a compound of general formula:

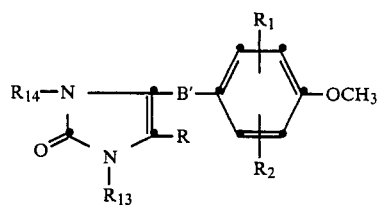

in which R, $R_1$, $R_2$, $R_{13}$, $R_{14}$ and B' have the same meaning as above which is subsequently demethylated using appropriate procedures such as in the presence of iodhydric acid, pyridine hydrochloride or hydrobromic acid, to obtain the required compound of formula I.

As an alternative procedure, the compounds of formula IV in question can be prepared by adapting the method similar to that described in J. Am. Chem. Soc. 68, p. 2350 (1946).

According to an alternative method, the compounds of formula I in which B represents a —S— or —SO$_2$— group and A represents an alkylene radical, preferably those in which A represents a propylene radical, can also be obtained by reacting, in the presence of a basic agent such as an alkali metal carbonate, for example potassium carbonate, an alkali metal hydroxide such as sodium or potassium hydroxide, an alkali metal hydride such as sodium hydride or an alkali metal alcoholate, for example sodium methylate or ethylate, a 4-hydroxyphenyl derivative of formula IV above with a compound of general formula:

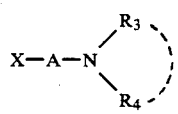

in which X has the same meaning as above and preferably represents chlorine or a benzenesulphonyl or p-toluenesulphonyl radical, A represents an alkylene radical and $R_3$ and $R_4$ have the same meaning as above, the reaction taking place at a temperature between room-temperature and the refluxing temperature of the medium and in a polar solvent such as methyl ethyl ketone or dimethylsulphoxide to form the desired aminoalkoxyphenyl derivative of formula I in the form of the free base.

When $R_4$ represents hydrogen, the nitrogen atom is preferably protected by a labile group for instance a protecting group which can be eliminated in basic medium for example the tertiobutoxycarbonyl (BOC) group.

The compounds of formula XXXXVIII are products which are known or which can be prepared by known methods.

The compounds of formula I in which Cy represents a group (E), A represents an alkylene chain and B represents a —S— or —SO$_2$— group can also be prepared by reacting a 2-R-imidazole or 2-R-benzimidazole with a halide of general formula:

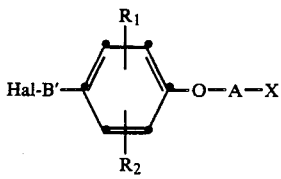

in which B', $R_1$, $R_2$, Hal and X have the same meaning as above and A represents an alkylene chain, in the presence of an acid acceptor such as triethylamine to obtain a compound of general formula:

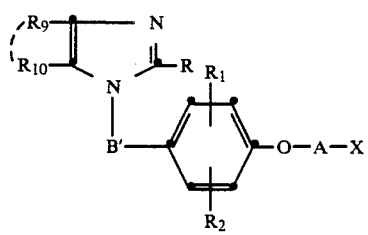

in which B', R, $R_1$, $R_2$ and X have the same meaning as above, $R_9$ and $R_{10}$ each represent hydrogen or are taken together with the carbon atom to which they are attached to form a phenyl group and A represents an alkylene chain, which compound is subsequently reacted with an amine of formula III to obtain the required compound of formula I in the form of a free base.

Similarly, the compounds of formula I in which Cy represents an optionally mono- or di- substituted 2-R-4,5-dihydro-furan-3-yl group, A represents an alkylene chain and B represents a —S— or —SO$_2$— group, can be prepared by hydrolysing a cyclopropane derivative of formula XXXII in the presence of an aqueous alkali metal hydroxide solution to provide a 4-methoxyphenyl derivative of general formula:

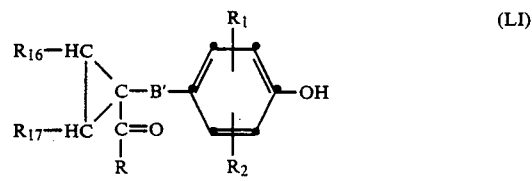

in which B', R, $R_1$, $R_2$, $R_{16}$ and $R_{17}$ have the same meaning as above, which is then reacted:

with a dihaloalkane of formula V and the resulting product with an amine of formula III or with a compound of general formula XXXXVIII, to provide an aminoalkoxyphenyl derivative of general formula:

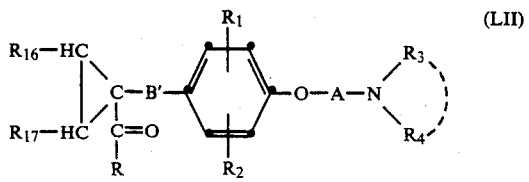

in which B', R, $R_1$, $R_2$, $R_3$, $R_4$, $R_{16}$ and $R_{17}$ have the same meaning as above and A represents an alkylene chain.

The cyclopropane derivative of formula (LII) is subsequently heated between 100 and 130° C. in the presence of a phase transfer catalyst such as for instance triphenylphosphine or tricaprylylmethyl ammonium chloride to provide the required 2,3-dihydrofuran derivative of formula I in the form of a free base.

II. When B represents a —SO— group, by treating, with an oxidizing agent, a sulphide of formula I in which B represents a —S— group, this compound of formula I being in the form of the free base of a salt thereof so as to obtain the required compound in the form of the free base or a salt thereof.

Where the required compound is provided in the form of a salt, the free base thereof can be recovered by treatment with a basic agent such as an alkali metal carbonate for example potassium carbonate or an alkali metal bicarbonate for example sodium bicarbonate.

Generally, the reaction takes place in water or in an organic solvent such as methylene chloride and in the presence of a suitable oxidizing agent such as for example sodium periodate, potassium permanganate or 3chloroperbenzoic acid.

Depending on the oxidizing agent used, mixtures of sulphoxides or sulphones can be obtained. These mixtures can be separated by conventional procedures for instance by chromatography.

III. When B represents a —S— or —$SO_2$— group and A represents an optionally substituted 2-hydroxypropylene chain, by reacting under reflux a 4-hydroxyphenyl derivative of formula IV with an epihalohydrin, such as epichlorhydrin or epibromhydrin in dextrorotatory or laevorotatory form or in the form of a mixture of these isomers, for example in racemic form, and in the presence of a basic agent such as an alkali metal carbonate, for example potassium carbonate, an alkali metal hydroxyde, for example sodium or potassium hydroxide, an alkali metal hydride, such as sodium hydride or an alkali metal alcoholate, for example sodium methylate of ethylate, and in a polar solvent such as methyl ethyl ketone to give the oxoiranylmethoxy derivatives of general formula:

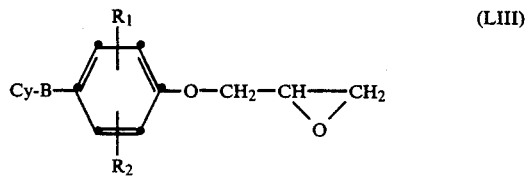

in which Cy, B, R, $R_1$ and $R_2$ have the same meaning as above.

The oxyranylmethoxy derivatives of formula (LIII) are then treated under reflux with an amine of formula III, this being performed in a polar solvent such as methyl ethyl ketone or in an excess of amine of formula III to give the desired compound of formula I in the form of the free base in which A represents a 2-hydroxypropylene chain which can be reacted, if desired, with a lower alkyl halide in the presence of a strong base to provide the compound of formula I in the form of the free base in which A represents a 2-hydroxypropylene chain in which the hydroxy is substituted by a lower alkyl radical.

In some cases, by-products may be formed in parallel with the compounds of formula (LIII) above, on this case 4-(3-halo-2-hydroxypropoxy)benzenesulphonyl derivatives.

On reaction with the amine of formula III, these derivatives will nevertheless give rise to the desired compounds of formula I in which A represents a 2-hydroxypropylene chain.

The compounds of formulae II, IV, VI and XIV in which Cy represents an indolizin-1yl group together with the compounds of formula VIII are new intermediate compounds.

In consequence, they constitute another subject of the invention.

Overall, these particular compounds of formulae II, IV, VI, VIII and XIV can be represented by the general formula:

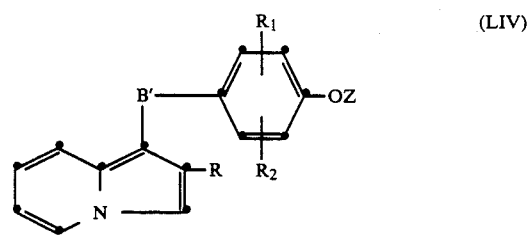

in which B', R, $R_1$ and $R_2$ have the same meaning as above and Z denotes hydrogen, an oxiranylmethyl radical, an alkylsulphonyl radical having from 1 to 4 carbon atoms, an arylsulphonyl radical having from 6 to 10 carbon atoms or a radical of formula:

—A—$Z_1$ in which A denotes a linear- or branched-alkylene radical having from 2 to 5 carbon atoms and $Z_1$ denotes a halogen atom, a hydroxy radical, an alkylsulphonyloxy radical having from 1 to 4 carbon atoms or an arylsulphonyloxy radical having from 6 to 10 carbon atoms.

The compounds of formula I thereby obtained in the form of the free base can then be converted to pharmaceutically acceptable salts by reaction with a suitable organic or inorganic acid, for example oxalic, maleic, fumaric, methanesulphonic, benzoic, ascorbic, pamoic, succinic, hexamic, bismethylenesalicylic, ethanedisulphonic, acetic, propionic, tartaric, salicylic, citric, gluconic, lactic, malic, cinnamic, mandelic, citraconic, aspartic, palmitic, stearic, itaconic, glycolic, p-aminobenzoic, glutamic, benzenesulphonic or theophyllineacetic acid or with lysine or histidine.

Similarly, the N-oxide derivatives of the compounds of formula I can be formed by oxidizing the compound of formula I in question with an appropriate oxidizing agent for instance hydrogen peroxide or 3-chloroperbenzoic acid.

Monoalkyl- or dialkylaminoalkoxybenzenesulphonyl-benzofuran or benzothiophene derivatives are reported in U.S. Pat. No. 4,117,128 as presenting pharmacological effects in the cardiovascular field.

In the course of the elaboration of the present invention, tests were carried out with compounds specifically cited in the aforesaid US patent, more particularly with 2-ethyl- or 2-n-butyl-3-[4-(2-diethylaminoethoxy)benzenesulphony]benzofuran.

From results of these tests, it could be concluded that in the dog at the dose of 10 mg/kg by intravenous route, these known compounds only present a weak α-antiadrenergic activity and no or practically no β-antiadrenergic effect.

It has now been surprisingly discovered, in the context of the present irn,ention, that by replacing the mono- or di-alkylaminoalkoxy chain of the benzenesulphonyl-benzofurans or benzothiophenes of the prior art by an aralkylaminoalkoxy chain, compounds are obtained which show much greater α- and β-antiadrenergic activities than those of the known compounds in question.

For instance, aralkylaminoalkoxybenzenesulphorylbenzofurans or benzothiophenes in question have shown, at doses as low as 0.1 to 1.5 mg/kg, sub-total inhibition of the α-adrenergic effect together with an important β-antiadrenergic action.

Such very valuable antiadrenergic properties were also found to be present in compounds similar in structure to the aralkylaminoalkoxybenzenesulphonyl-benzofurans and benzothiophenes in question but in which the benzofuran or benzothiophene moiety is replaced by another carbocyclic or heterocyclic group.

Therefore, one class of compounds of the inzention relates to those compounds of formula I and the pharmaceutically acceptable salts or N oxide thereof, in which Cy, $R_1$, $R_2$, $R_4$ and A have the same meaning as in formula I, B represents a —$SO_2$— group and $R_3$ represents a radical —Alk—$R_5$.

A particularly valuable class of compounds of the irn.ention are those in which $R_1$, $R_2$, $R_4$ and A have the same meaning as in formula I, B represents a —$SO_2$— group, $R_3$ represents a radical —Alk—$R_5$, Cy represents a group selected from:
indolizinyl more particularly 2-R-indolizin-1-yl and 2-R-indolizin3-yl
benzofuryl or benzothienyl more larly 2-R-benzofur-3-yl and 2-R-benzothien-3-yl
quinolinyl such as 2-R-quinolin-3-yl
pyrrolo[1,2-b]pyridazinyl more particularly 6-R-pyrrolo[1,2-b]pyridazin-5-yl
pyrazolo[1,5-a]pyridyl more particularly 2-R-pyrazolo[1,5-a]pyrid-3-yl
imidazo[1,2-a]pyridyl more particularly 2-R-imidazo[1,2-a]pyrid-3-yl
4,5-dihydrofuranyl more particularly 2-R-3,4-dihydrofuran-3-yl group.

Similarly indolizine derivatives which are substituted in the 1-position with an alkyloxybenzoyl chain which is itself substituted with a mono- or di-alkyl amino group, and which are stated to have pharmacological effects in the cardiovascular field, are already known.

In this connection, there may be mentioned French Patent No. 2,341,578 and Eur. J. Med. Chem. 1977, 12, No. 4 pp. 345-350, which specifically describe 2-ethyl-, 2-n-propyl- or 2-n-butyl-1-[4-(3-di-n-propyl- or 3-di-n-butylaminopropoxy)-benzoyl]indiolizine optionally dimethylated on the benzoyl radical.

These known compounds showed antiadrenergic activities which were nonexistent or low, at all events too low to be of any value for therapy.

Other monoalkyl- or dialkyl-aminoalkoxybenzoyl derivatives are also known.

For instance are reported in the literature monoalkyl- or dialkyl-aminobenzoyl derivatives of:
thiophene [(J. Med. Chem. V, 13 (3) pp. 359–366 (1970)]
naphthalene or dihydronaphthalene (Chim. Ther. V, 7 (5) pp. 369-377)
pyridine [Ing. Chim. V, 59 (283) pp. 3–13 (1977)]
thieno[3,2-c]pyridine [Heterocycles, V, 22 (5), pp. 1235–1247 (1984)]
Chim. Ther. V, 12 (5) pp. 483–487 (1977)]
indole [Eur. J. Med. Chem. - Chim. Ther. V, 12 (5) pp. 483–487 (1977)]
furan (French patent No. 2,400,515)
chromone (U.S. Pat. No. 4,220,645)

Tests carried out with these known compounds showed that same of them presented antiadrenergic activities but which were low, at all events too low to be of any value for therapy.

It has now been found, in addition, that mono- or di-alkylaminoalkoxy benzenesulphonyl derivatives ressembling those described in U.S. Pat. No. 4,117,128 but in which the benzofuran or benzothiophene moiety has been replaced by another carbocyclic or heterocyclic ring present more valuable antiadrenergic properties than known sulphonyl derivatives of the aforesaid U.S. patent or known benzoyl derivatives of the above-cited references.

For instance, α- and β-antiadrenergic properties were registered, in the dog by intravenous route at doses as low as 0.1 to 1.5 mg/kg with respect to mono- or di-alkylaminoalkoxybenzenesulphonyl derivatives of formula I in which Cy represents another group than benzofuryl or benzothienyl for instance a quinolinyl or pyrrolo[1,2-b]pyridazinyl moiety.

Yet, another valuable class of compounds of the invention are those in which $R_1$, $R_2$, $R_4$ and A have the same meaning as in formula I, B represents a —$SO_2$— group and $R_3$ represents an alkyl radical with the proviso that Cy is different from benzo[b]furyl or benzo[b]thienyl.

A particularly valuable class of compounds of the invention are those in which $R_1$, $R_2$, $R_4$ and A have the same meaning as in formule I, B represents a —$SO_2$— group, $R_3$ represents an alkyl radical and Cy represents a group selected from:
quinolinyl more particularly 2-R-quinolin-3-yl
pyrrolo[1,2-b]pyridazinyl more particularly 6-R-pyrrolo[1,2-b]pyridazin-5-yl.
pyrazolo[1,5-a]pyridyl more particularly 2-R-pyrazolo[1,5-a]pyrid-3-yl.
imidazo[1,2-a]pyridyl more particularly 2-R-imidazo[1,2-a]pyrid-3-yl.
4,5-dihydrofurannyl more particularly 2-R-4,5-dihydrofuran-3-yl group.

Moreover, it has been found that the calcium inhibitory activity of the comoounds of the invention is at least equal to, if not greater than, that observed in tests performed witn the xnown comoounds. In contrast to the known compounds, it has thus been possible to demonstrate for the comoounds of the present invention a pharmacological soectrum revealing anticalcium and α- and β-antiadrenergic components with a balanced intensity which is of theraoeutic value, for example, for treatment of angina.

As has been recorded in detail by R. Charlier in "Bruxelles Medical", No. 9, September 1969, pages 543–560, it is accepted than an antianginal drug treatment should be capable, in particular, of antagonizing the antiadrenergic type cardiovascular reactions. To this end, agents capable of blocking the α-receptors have been proposed.

However, the clinical application of such compounds to the treatment of angina remained unsuccessful, very crobably due to the fact that α-receptor antagonists induce only a very partial neutralization of the adrenergic system, the activity of the β-receptors being unaffected.

In fact, the most undesirable haemodynamic manifestations which occur in angina pectoris patients during their painful attacks are, most of all, cardiac, and consequently involve the β-receptors.

In parallel, treatments have been proposed with drugs which are β-adrenergic receptor antagonists. These compounds, which are of genuine clinical value, decrease the attacks of angina by reducing the work of the heart by slowing the heart rate. However, there is no fall in the peripheral arterial resistance which, on the contrary, rises through release of the α-tonicity.

These drug treatments nevertheless modify some haemodynamic parameters in a direction which, at a fundamental level, detracts from the value of these drugs for angina oectoris oatients in particular and heart patients in general.

If the antiadrenergic aspect of β-blockers is considered, it becomes clear that only the tachycardia and the increase in the force and the soeed of contraction of the heart are capable of being neutralized, the arterial hyoertension involving a stimulation of the o-receptors on which β-antagonists have no action.

In fact, while the cardiovascular disturbances brought about by the stimulation of the β-receptors are the more harmful to angina patients, it is nonetheless true that arterial hycertension also plays a not insignificant part.

In addition, blocking the β-receptors involves a risk, depriving the patient suffering from cardiac insufficiency of a compensatory mechanism which he normally brings into play to limit his circulatory insufficiency.

This reflex mechanism, the main comoonent of which makes use of the pathway of the β-adrenergic system, leads, in particular, to an increase in the force and the speed of contraction of the heart. In consequence, if this system is blocked, the patient suffering from cardiac insufficiency experiences a worsening of his functional breakdown. It is hence logical to consider that the use of a β-blocker whose action is cure and complete will always involve a cardiac risk.

It hence appears to be desirable not to seek complete α- or β-antagonistic properties, given the clinical side effects that these can bring about. It seems more logical to aim to subdue rather than to eliminate the cardiovascular disturbances which characterize the hyperstimulation of the adrenergic system as a whole.

The compounds of the invention meet this objective since they show incomplete α- and β-type antiadrenergic properties. They can hence be considered, not as β-blockers but as adreno-decelerators, that is to say partial antagonists of tne α- and β-adrenergic reactions, potentially devoid of the disadvantages listed above for β-blockers.

In addition, the calcium inhibitory component demonstrated in the comoounds of the invention will act as an exceptional complement to the pharmacological spectrum of their cardiovascular action.

It is known, in effect, that the transport of calcium ions is one of the main components of the action potential in heart cells and, in consequence, this transport plays a fundamental part in the electrical conduction as well as in the disorders which may occur therein (arrhythmia). In addition, it is known that calcium ions are involved in the excitation-contraction coupling which controls the degree of vasoconstriction in smooth muscle and, in the same circumstances, plays a critical part in attacks of angina pectoris.

Compounds which are calcium antagonists act at the level of the cell membrane by selectively preventing calcium from participating in the process of contraction within the arterial cell.

In fact, it appears increasingly clear, at the present time, that the clinical results provided by the combination of calcium inhibitors and β-adrenergic inhibitors are better than when each inhibitor is used separately (J.A.M.A. 1982, 247, pages 1911–1917).

It appears, moreover, that no β-blocker which exerts, in addition, a significant inhibitory respect of calcium transport exists at the present time.

From this standpoint, the compounds of the invention possessing both an anticalcium component and an α- and β-antiadrenergic component will be of fundamental value, since they are capable of more extensive therapeutic applications than a separate β-blocker or a separate calcium inhibitor. By way of example, the following may be mentioned:

2-ethyl-1-[4-{3-[N-methyl-N-(3,4-dimethoxy-β-phenethyl)-amino]propyloxy}benzenesulphonyl]indolizine (EX. 28)

2-isoprooyl-1-{4-[3-(di-n-butylamino)cropyloxy]benzenesulphonyl}indolizine (Ex.1)

2-ethyl-1-{4-[3-(di-n-butylamino)propyloxy]benzenesulphcnyl}indolizine (Ex.8), and 2-isopropyl-1-[4-{3 -[N-methyl-N-(3,4-dimethoxy-β-phenethyl)amino]-propyloxy}benzenesulphonyl]indolizine (Ex.3O)

which possess an α- and β-antiadrenergic component reinfcrced by an oxygen-economizing effect capable of prcviding a theraoeutic effect in man in the syndrome of angina of effort, which can, moreover, be treated by traditional β-blockers. However, the major advantage of these compounds will reside in the fact that they may, as a result of their anti-calcium effect, be used in the treatment of angina at rest, a syndrome induced by the appearance of a spasm in the coronary arteries, which is combated at present by compounds such as diltiazem, verapamil or nifedipine.

In addition, compounds of the invention were also shown to be capable of inducing a substantial increase in the coronary flow.

The results of pharmacological tests performed for the purpose of determining the cardiovascular properties of the compounds of the invention are recorded below.

I. Calcium Inhibitory Properties

The properties of inhibiting calcium transport at the membrane level shown by the compounds of the invention were demonstrated by measuring their antagonistic action with respect to the contractile response to potassium-induced depolarization on isolated rat aorta. It is well established that the depolarization of a smooth muscle membrane by potassium renders the latter permeable to extracellular calcium and induces muscle contraction.

Consequently, the measurement of the inhibition of the contractile response to depolarization by potassium, or the measurement of a relaxation of the tonic contraction on potassium depolarization, can represent an evaluation of the power of a compound as an inhibitor of the membrane permeability to $Ca^{++}$ ions.

The technique used was as follows:

The aorta was removed from male Wistar rats weighing approximately 300g, and cut into strips approximately 40 mm long and 3 mm wide.

These fragments were placed in a 25-ml isolated organ trough containing a modified Krebs-bicarbonate solution (112 mM NaCl; 5 mM KCl; 25 mM $NaHCO_3$; 1 mM $KH_2PO_4$ $MgSO_4$; 2.5 mM $CaCl_2$; 11.5 mM glucose, distilled water to 1000 ml) through which a stream of 5-7% carbon dioxide in oxygen was passed, and maintained at 37° C. The preparation was connected to a force microsensor and the contractile response recorded after amplification on a recorder.

A tension of 2 g was applied to the preparation. This tension was maintained for 60 minutes in the modified Krebsbicarbonate solution, and contractions were then induced by replacing the Krebs-bicarbonate solution by a potassium-Krebs solution (17 mM NaCl; 100 mM KCl; 25 mM $NaHCO_3$; 1 mM $KH_2PO_4$; 1.2 mM $MgSO_4$; 2.5 mM $CaCl_2$; 11.5 mM glucose; distilled water to 1000 ml). When the contractile response of the preparation had become reproducible, a given amount of a compound of the invention was introduced into the bath. Sixty minutes later, a new spasm was induced by potassium depolarization.

The results obtained on the aorta used in the experiment were then expressed as a percentage of the maximum contractional effect before incubation with the test substance.

By way of examples, the results which follow were obtained, the compounds of formula I being in the form of the base, hydrochloride or oxalate.

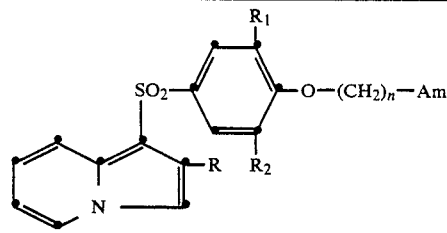

| Compound | R | $R_1$ | $R_2$ | n | Am | % of the maximum contractional effect |
|---|---|---|---|---|---|---|
| (a) At a dose of $10^{-6}$ M | | | | | | |
| Ex. 12 | $n$-$C_4H_9$ | H | H | 3 | $-N(n$-$C_3H_7)_2$ | 36.3 |
| Ex. 13 | $n$-$C_4H_9$ | H | H | 3 | $-N(n$-$C_4H_9)_2$ | 39.8 |
| Ex. 29 | $n$-$C_4H_9$ | H | H | 3 | $-NH-C(CH_3)_3$ | 30.7 |
| Ex. 18 | phenyl | H | H | 3 | $-N(n$-$C_4H_9)_2$ | 55.6 |
| Ex. 19 | phenyl | $CH_3$ | H | 3 | $-N(n$-$C_4H_9)_2$ | 77.2 |
| Ex. 24 | phenyl | H | H | 3 | $-NH-C(CH_3)_3$ | 62.1 |
| Ex. 25 | phenyl | H | $CH_3$ | 3 | $-NH-C(CH_3)_3$ | 67.7 |
| Ex. 21 | $-C_2H_5$ | H | H | 3 | $-NH(n$-$C_4H_9)$ | 8.3 |
| Ex. 20 | $-C_2H_5$ | H | H | 3 | $-N(CH_3)(n$-$C_4H_9)$ | 6.8 |
| Ex. 10 | $-C_2H_5$ | $CH_3$ | $CH_3$ | 3 | $-N(n$-$C_4H_9)_2$ | 2.9 |
| Ex. 4 | $-CH_3$ | H | H | 3 | $-N(C_2H_5)_2$ | 77.2 |
| Ex. 5 | $-CH_3$ | H | H | 3 | $-N(n$-$C_3H_7)_2$ | 48.9 |
| Ex. 6 | $-CH_3$ | H | H | 3 | $-N(n$-$C_4H_9)_2$ | 13.9 |
| Ex. 7 | $-C_2H_5$ | H | H | 3 | $-N(n$-$C_3H_7)_2$ | 8.3 |

-continued

| | | | | | | |
|---|---|---|---|---|---|---|
| Ex. 9 | —$C_2H_5$ | $CH_3$ | H | 3 | —$N(n-C_4H_9)_2$ | 17.4 |
| Ex. 3 | —$C_2H_5$ | H | H | 3 | —NH—$C(CH_3)_3$ | 30.7 |
| Ex. 2 | —$C_2H_5$ | H | H | 3 | —N⟨morpholine⟩ | 22.6 |
| Ex. 11 | —n-$C_3H_7$ | H | H | 3 | —$N(n-C_4H_9)_2$ | 8.8 |
| Ex. 14 | —$CH(CH_3)_2$ | H | H | 3 | —$N(CH_3)_2$ | 32.6 |
| Ex. 15 | —$CH(CH_3)_2$ | H | H | 3 | —$N(C_2H_5)_2$ | 18.4 |
| Ex. 17 | —$CH(CH_3)_2$ | H | H | 3 | —$N(n-C_3H_7)_2$ | 7.4 |
| Ex. 1 | —$CH(CH_3)_2$ | H | H | 3 | —$N(n-C_4H_9)_2$ | 2.0 |
| Ex. 31 | —$CH(CH_3)_2$ | H | H | 3 | —NH—$CH_2$—$CH_2$—Ph | 16.8 |
| Ex. 32 | —$CH(CH_3)_2$ | H | H | 3 | —NH—$CH_2$—Ph | 3.6 |
| Ex. 33 | —$CH(CH_3)_2$ | H | H | 3 | —N(piperazinyl)-Ph | 24.6 |
| Ex. 34 | —$CH(CH_3)_2$ | H | H | 3 | —NH—$CH_2$—$CH_2$—pyridyl | 3.3 |
| Ex. 35 | —$CH(CH_3)_2$ | H | H | 3 | —N(piperidinyl)-Ph | 8.3 |
| Ex. 36 | —$CH(CH_3)_2$ | H | H | 3 | —$N(n-C_8H_{17})_2$ | 83.3 |
| Ex. 44 | —$CH(CH_3)_2$ | H | H | 3 | —NH—(3,4-di-$OCH_3$-Ph) | 29.8 |
| Ex. 51 | ⟨phenyl⟩ | H | H | 3 | —$N(n-C_4H_9)_2$ | 58.9 |

(b) At a dose of $10^{-7}$ M

| | | | | | | |
|---|---|---|---|---|---|---|
| Ex. 21 | —$C_2H_5$ | H | H | 3 | —$NH(n-C_4H_9)$ | 74.7 |
| Ex. 20 | —$C_2H_5$ | H | H | 3 | —$N(CH_3)(n-C_4H_9)$ | 60.0 |
| Ex. 10 | —$C_2H_5$ | $CH_3$ | $CH_3$ | 3 | —$N(n-C_4H_9)_2$ | 49.0 |
| Ex. 22 | —$C_2H_5$ | H | H | 2 | —$N(n-C_4H_9)_2$ | 37.0 |
| Ex. 23 | —$C_2H_5$ | H | H | 4 | —$N(n-C_4H_9)_2$ | 24.1 |
| Ex. 26 | —$C_2H_5$ | H | H | 3 | —$N(n-C_5H_{11})_2$ | 42.9 |
| Ex. 6 | —$CH_3$ | H | H | 3 | —$N(n-C_4H_9)_2$ | 69.1 |
| Ex. 7 | —$C_2H_5$ | H | H | 3 | —$N(n-C_3H_7)_2$ | 60.0 |
| Ex. 8 | —$C_2H_5$ | H | H | 3 | —$N(n-C_4H_9)_2$ | 30.9 |
| Ex. 9 | —$C_2H_5$ | $CH_3$ | H | 3 | —$N(n-C_4H_9)_2$ | 57.2 |
| Ex. 2 | —$C_2H_5$ | H | H | 3 | —N⟨morpholine⟩ | 79.8 |
| Ex. 11 | —n-$C_3H_7$ | H | H | 3 | —$N(n-C_4H_9)_2$ | 37.7 |
| Ex. 15 | —$CH(CH_3)_2$ | H | H | 3 | —$N(C_2H_5)_2$ | 71.2 |

-continued

| | | | | | | |
|---|---|---|---|---|---|---|
| Ex. 17 | —CH(CH$_3$)$_2$ | H | H | 3 | —N(n-C$_3$H$_7$)$_2$ | 50.4 |
| Ex. 1 | —CH(CH$_3$)$_2$ | H | H | 3 | —N(n-C$_4$H$_9$)$_2$ | 18.9 |
| Ex. 16 | —C(CH$_3$)$_3$ | H | H | 3 | —N(n-C$_4$H$_9$)$_2$ | 35.8 |
| Ex. 27 | —C$_2$H$_5$ | H | H | 3 | —NH—(CH$_2$)$_2$—C$_6$H$_3$(OCH$_3$)$_2$ 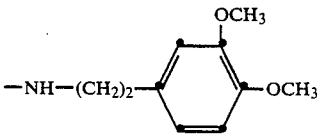 | 7.7 |
| Ex. 28 | —C$_2$H$_5$ | H | H | 3 | —N(CH$_3$)—(CH$_2$)$_2$—C$_6$H$_3$(OCH$_3$)$_2$ 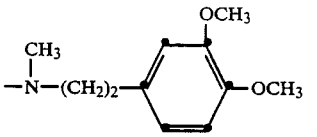 | 14.2 |
| Ex. 30 | —CH(CH$_3$)$_2$ | H | H | 3 | —N(CH$_3$)—(CH$_2$)$_2$—C$_6$H$_3$(OCH$_3$)$_2$ 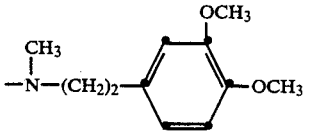 | 9.4 |
| Ex. 31 | —CH(CH$_3$)$_2$ | H | H | 3 | —NH—CH$_2$—CH$_2$—C$_6$H$_5$ 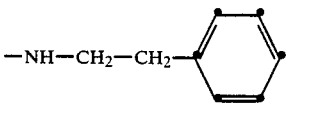 | 31.8 |
| Ex. 32 | —CH(CH$_3$)$_2$ | H | H | 3 | —NH—CH$_2$—C$_6$H$_5$ 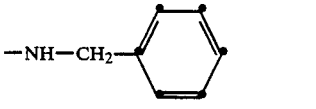 | 19.4 |
| Ex. 33 | —CH(CH$_3$)$_2$ | H | H | 3 | 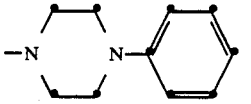 (N-phenylpiperazinyl) | 57.6 |
| Ex. 34 | —CH(CH$_3$)$_2$ | H | H | 3 | —NH—CH$_2$—CH$_2$—(2-pyridyl) 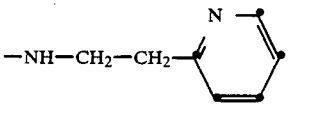 | 28.1 |
| Ex. 35 | —CH(CH$_3$)$_2$ | H | H | 3 | 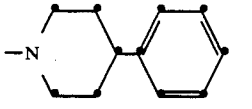 (4-phenylpiperidinyl) | 25.0 |
| Ex. 36 | —CH(CH$_3$)$_2$ | H | H | 3 | —N(n-C$_8$H$_{17}$)$_2$ | 93.7 |
| Ex. 38 | —C$_2$H$_5$ | H | H | 3 | 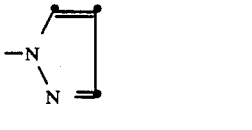 (pyrazolyl) | 85.9 |
| Ex. 37 | —CH(CH$_3$)$_2$ | H | H | 3 | —N(n-C$_5$H$_{11}$)$_2$ | 48.7 |
| Ex. 39 | —CH(CH$_3$)$_2$ | H | H | 4 | —N(n-C$_4$H$_9$)$_2$ | 17.9 |
| Ex. 40 | —C$_2$H$_5$ | H | H | 5 | —N(n-C$_4$H$_9$)$_2$ | 49.7 |
| Ex. 41 | —CH(CH$_3$)$_2$ | H | H | 3 | —N(CH$_3$)—CH$_2$—C$_6$H$_3$(OCH$_3$)$_2$ 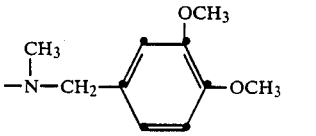 | 5.3 |

-continued

| | | | | | | |
|---|---|---|---|---|---|---|
| Ex. 46 | —CH(CH₃)₂ | H | H | 3 | —N(CH₃)—(CH₂)₂—C₆H₄(OCH₃) | 4.3 |
| Ex. 47 | —CH(CH₃)₂ | H | H | 3 | —N(CH₃)—(CH₂)₂—C₆H₄(OCH₃) | 17.9 |
| Ex. 44 | —CH(CH₃)₂ | H | H | 3 | —NH—C₆H₃(OCH₃)(OCH₃) | 78.9 |
| Ex. 43 | —CH(CH₃)₂ | H | H | 3 | —NH—CH₂—C₆H₃(OCH₃)(OCH₃) | 9.7 |
| Ex. 42 | —CH(CH₃)₂ | H | H | 4 | —N(CH₃)—(CH₂)₂—C₆H₃(OCH₃)(OCH₃) | 21.1 |
| Ex. 45 | —CH(CH₃)₂ | H | H | 3 | —N(n-C₄H₉)—(CH₂)₂—C₆H₃(OCH₃)(OCH₃) | 18.7 |
| Ex. 51 | cyclohexyl | H | H | 3 | —N(n-C₄H₉)₂ | 80.4 |
| (c) At a dose of 10⁻⁸ M | | | | | | |
| Ex. 10 | —C₂H₅ | CH₃ | CH₃ | 3 | —N(n-C₄H₉)₂ | 82.6 |
| Ex. 22 | —C₂H₅ | H | H | 2 | —N(n-C₄H₉)₂ | 90.2 |
| Ex. 23 | —C₂H₅ | H | H | 4 | —N(n-C₄H₉)₂ | 77.8 |
| Ex. 26 | —C₂H₅ | H | H | 3 | —N(n-C₅H₁₁)₂ | 82.9 |
| Ex. 1 | —CH(CH₃)₂ | H | H | 3 | —N(n-C₄H₉)₂ | 61.0 |
| Ex. 16 | —C(CH₃)₃ | H | H | 3 | —N(n-C₄H₉)₂ | 78.7 |
| Ex. 27 | —C₂H₅ | H | H | 3 | —NH—(CH₂)₂—C₆H₃(OCH₃)(OCH₃) | 58.9 |
| Ex. 28 | —C₂H₅ | H | H | 3 | —N(CH₃)—(CH₂)₂—C₆H₃(OCH₃)(OCH₃) | 60.2 |
| Ex. 30 | —CH(CH₃)₂ | H | H | 3 | —N(CH₃)—(CH₂)₂—C₆H₃(OCH₃)(OCH₃) | 40.1 |

-continued

| | | | | | | |
|---|---|---|---|---|---|---|
| Ex. 31 | —CH(CH$_3$)$_2$ | H | H | 3 | —NH—CH$_2$—CH$_2$—C$_6$H$_5$ | 73.9 |
| Ex. 32 | —CH(CH$_3$)$_2$ | H | H | 3 | —NH—CH$_2$—C$_6$H$_5$ | 65.9 |
| Ex. 33 | —CH(CH$_3$)$_2$ | H | H | 3 | piperazinyl-phenyl | 87.0 |
| Ex. 34 | —CH(CH$_3$)$_2$ | H | H | 3 | —NH—CH$_2$—CH$_2$-(2-pyridyl) | 82.6 |
| Ex. 35 | —CH(CH$_3$)$_2$ | H | H | 3 | 4-phenylpiperidinyl | 65.6 |
| Ex. 37 | —CH(CH$_3$)$_2$ | H | H | 3 | —N(n-C$_5$H$_{11}$)$_2$ | 77.8 |
| Ex. 39 | —CH(CH$_3$)$_2$ | H | H | 4 | —N(n-C$_4$H$_9$)$_2$ | 62.9 |
| Ex. 40 | —C$_2$H$_5$ | H | H | 5 | —N(n-C$_4$H$_9$)$_2$ | 87.9 |
| Ex. 41 | —CH(CH$_3$)$_2$ | H | H | 3 | —N(CH$_3$)—CH$_2$-(2,3-dimethoxyphenyl) | 26.1 |
| Ex. 46 | —CH(CH$_3$)$_2$ | H | H | 3 | —N(CH$_3$)—(CH$_2$)$_2$-(2-methoxyphenyl) | 49.5 |
| Ex. 47 | —CH(CH$_3$)$_2$ | H | H | 3 | —N(CH$_3$)—(CH$_2$)$_2$-(4-methoxyphenyl) | 69.6 |
| Ex. 44 | —CH(CH$_3$)$_2$ | H | H | 3 | —NH-(2,3-dimethoxyphenyl) | 89.5 |
| Ex. 43 | —CH(CH$_3$)$_2$ | H | H | 3 | —NH—CH$_2$-(2,3-dimethoxyphenyl) | 58.4 |
| Ex. 42 | —CH(CH$_3$)$_2$ | H | H | 4 | —N(CH$_3$)—(CH$_2$)$_2$-(2,3-dimethoxyphenyl) | 53.9 |

-continued

| | | | | | | |
|---|---|---|---|---|---|---|
| Ex. 45 | —CH(CH$_3$)$_2$ | H | H | 3 | —N(n-C$_4$H$_9$)—(CH$_2$)$_2$—C$_6$H$_3$(OCH$_3$)$_2$ | 62.3 |

(d) At a dose of $10^{-9}$ M

| | | | | | | |
|---|---|---|---|---|---|---|
| Ex. 27 | —C$_2$H$_5$ | H | H | 3 | —NH—(CH$_2$)$_2$—C$_6$H$_3$(OCH$_3$)$_2$ | 81.6 |
| Ex. 28 | —C$_2$H$_5$ | H | H | 3 | —N(CH$_3$)—(CH$_2$)$_2$—C$_6$H$_3$(OCH$_3$)$_2$ | 85.4 |
| Ex. 30 | —CH(CH$_3$)$_2$ | H | H | 3 | —N(CH$_3$)—(CH$_2$)$_2$—C$_6$H$_3$(OCH$_3$)$_2$ | 81.7 |
| Ex. 41 | —CH(CH$_3$)$_2$ | H | H | 3 | —N(CH$_3$)—CH$_2$—C$_6$H$_3$(OCH$_3$)$_2$ | 70.9 |
| Ex. 46 | —CH(CH$_3$)$_2$ | H | H | 3 | —N(CH$_3$)—(CH$_2$)$_2$—C$_6$H$_4$(OCH$_3$) | 78.1 |
| Ex. 47 | —CH(CH$_3$)$_2$ | H | H | 3 | —N(CH$_3$)—(CH$_2$)$_2$—C$_6$H$_4$(OCH$_3$) | 86.5 |
| Ex. 43 | —CH(CH$_3$)$_2$ | H | H | 3 | —NH—CH$_2$—C$_6$H$_3$(OCH$_3$)$_2$ | 88.7 |
| Ex. 42 | —CH(CH$_3$)$_2$ | H | H | 4 | —N(CH$_3$)—(CH$_2$)$_2$—C$_6$H$_3$(OCH$_3$)$_2$ | 78.8 |
| Ex. 45 | —CH(CH$_3$)$_2$ | H | H | 3 | —N(n-C$_4$H$_9$)—(CH$_2$)$_2$—C$_6$H$_3$(OCH$_3$)$_2$ | 80.7 |

-continued

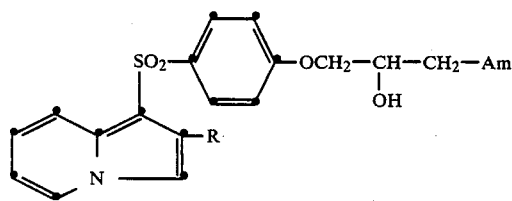

| Compound | R | Am | % of the maximum contractional effect | | | |
|---|---|---|---|---|---|---|
| | | | $10^{-6}$ M | $10^{-7}$ M | $10^{-8}$ M | $10^{-9}$ M |
| Ex. 49 | —CH(CH$_3$)$_2$ | —N—(n-C$_4$H$_9$)$_2$ | 5.4 | 12.8 | 67.6 | 80.2 |
| Ex. 50 | —CH(CH$_3$)$_2$ | (methyl-N-(CH$_2$)$_2$-3,4-dimethoxyphenyl) | 4.6 | 6.6 | 44 | 78 |

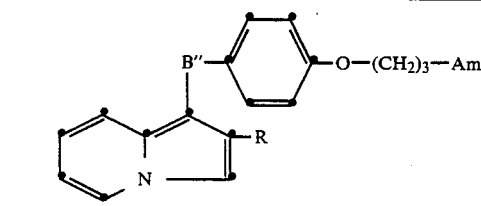

| Compound | B" | R | Am | % of the maximum contractional effect | | | |
|---|---|---|---|---|---|---|---|
| | | | | $10^{-5}$ M | $10^{-6}$ M | $10^{-7}$ M | $10^{-8}$ M |
| Ex. 52 | —S— | —CH(CH$_3$)$_2$ | —N—(n-C$_4$H$_9$)$_2$ | 69.2 | 81.2 | — | — |
| Ex. 53 | —S— | —CH(CH$_3$)$_2$ | (methyl-N-(CH$_2$)$_2$-3,4-dimethoxyphenyl) | 59.8 | 75.4 | — | — |
| Ex. 54 | —SO— | —CH(CH$_3$)$_2$ | —N—(n-C$_4$H$_9$)$_2$ | — | — | 74.3 | 82.4 |

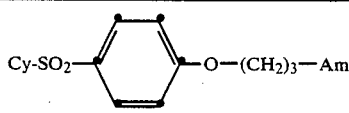

| Compound | Cy | Am | % of the maximum contractional effect | | | |
|---|---|---|---|---|---|---|
| | | | $10^{-6}$M | $10^{-7}$M | $10^{-8}$M | $10^{-9}$M |
| Ex. 74 | 2-isopropyl-quinolinyl | —N(n-C$_4$H$_9$)$_2$ | 22.4 | 67.3 | — | — |
| Ex. 75 | 2-isopropyl-quinolinyl | (methyl-N-(CH$_2$)$_2$-3,4-dimethoxyphenyl) | 3.7 | 54 | 89.7 | — |
| Ex. 70 | 3-isopropyl-pyridazinyl | —N(n-C$_4$H$_9$)$_2$ | 0 | 18.9 | 83 | — |

-continued

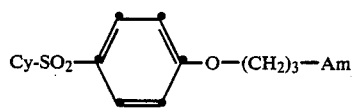

| Compound | Cy | Am | % of the maximum contractional effect | | | |
|---|---|---|---|---|---|---|
| | | | $10^{-6}$M | $10^{-7}$M | $10^{-8}$M | $10^{-9}$M |
| Ex. 71 | pyridazine-CH3, C3H7-iso | -N(CH3)-(CH2)2-(3,4-dimethoxyphenyl) | 0 | 15.1 | 67.1 | 84.9 |
| Ex. 72 | pyridazine-CH3, C3H7-iso | -NH-C(CH3)3 | 13.2 | 66.5 | 84 | — |
| Ex. 76 | pyrazole-CH3, C3H7-iso | -N(CH3)-(CH2)2-(3,4-dimethoxyphenyl) | — | 0 | 18.1 | 68.1 |
| Ex. 63 | phenyl | -N(CH3)-(CH2)2-(3,4-dimethoxyphenyl) | 21.4 | 73.7 | — | — |
| Ex. 64 | phenyl | -N(n-C4H9)2 | 32.4 | 85.3 | — | — |
| Ex. 65 | N-methylbenzimidazole-C4H9-n | -N(n-C4H9)2 | 47.5 | 64.8 | — | — |
| Ex. 55 | indolizine-CH3, C3H7-iso | -N(CH3)-(CH2)2-(3,4-dimethoxyphenyl) | — | 9.5 | 34.1 | 68.7 |
| Ex. 66 | benzofuran-CH3, C3H7-iso | -N(CH3)-(CH2)2-(3,4-dimethoxyphenyl) | 2.6 | 19.7 | 60.4 | 81.7 |
| Ex. 67 | benzofuran-C3H7-n | -N(CH3)-(CH2)2-(3,4-dimethoxyphenyl) | 9.3 | 38.3 | 80.9 | — |
| Ex. 68 | benzothiophene-C3H7-n | -N(CH3)-(CH2)2-(3,4-dimethoxyphenyl) | 9.7 | 45.3 | 68.9 | — |

-continued

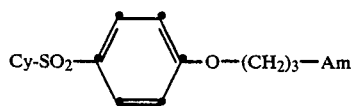

| Compound | Cy | Am | % of the maximum contractional effect | | | |
|---|---|---|---|---|---|---|
| | | | $10^{-6}$M | $10^{-7}$M | $10^{-8}$M | $10^{-9}$M |
| Ex. 69 | benzofuran-$C_4H_9$-n | $-N(CH_3)-(CH_2)_2-$(2,3-dimethoxyphenyl) | 36.8 | 59 | 76 | — |
| Ex. 73 | furan-$C_3H_7$-iso | $-N(CH_3)-(CH_2)_2-$(2,3-dimethoxyphenyl) | 8.2 | 66.7 | 78.3 | — |
| Ex. 77 | furan-$C_3H_7$-iso | $-N(CH_3)-(CH_2)_2-$(2,3-dimethoxyphenyl) | — | 43.2 | 86 | 89.8 |
| Ex. 78 | furan-$C_3H_7$-iso | $-N(n-C_4H_9)_2$ | 4.0 | 59.4 | 90.3 | — |
| Ex. 79 | furan-$C_3H_7$-iso | $-NH-C(CH_3)_3$ | 10.3 | 77.9 | 94.3 | — |

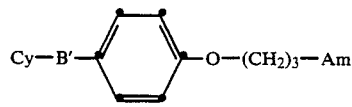

| Comp. | Cy | B' | Am | % of the maximum contractional effect | | |
|---|---|---|---|---|---|---|
| | | | | $10^{-5}$M | $10^{-6}$M | $10^{-7}$M |
| Ex. 59 | pyridin-2-yl | $-SO_2-$ | $-N(CH_3)-(CH_2)_2-$(2,3-dimethoxyphenyl) | 33.3 | 81.7 | 87.5 |
| Ex. 58 | pyridin-2-yl | $-SO_2-$ | $-N(n-C_4H_9)_N$ | 37 | 84.7 | 88.9 |
| Ex. 62 | pyridin-2-yl | $-SO_2-$ | $-NH-C(CH_3)_3$ | 70.6 | 87.1 | — |
| Ex. 60 | pyridin-3-yl | $-SO_2-$ | $-N(n-C_4H_9)_2$ | 20.2 | 75.5 | 89.7 |

-continued

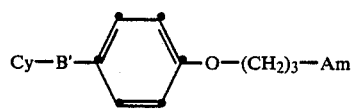

| Comp. | Cy | B' | Am | % of the maximum contractional effect | | |
|---|---|---|---|---|---|---|
| | | | | $10^{-5}M$ | $10^{-6}M$ | $10^{-7}M$ |
| Ex. 61 | pyridyl | —SO$_2$— | —N(CH$_3$)—(CH$_2$)$_2$—(3,4-dimethoxyphenyl) | 14 | 70.7 | 88 |
| Ex. 56 | pyridyl | —S— | —N(n-C$_4$H$_9$)$_2$ | 2.6 | 58 | 86.2 |
| Ex. 57 | pyridyl | —S— | —N(CH$_3$)—(CH$_2$)$_2$—(3,4-dimethoxyphenyl) | 3.1 | 59 | 85 |
| Ex. 80 | cinnolinyl | —S— | —N(CH$_3$)—(CH$_2$)$_2$—(3,4-dimethoxyphenyl) | 3.0 | 64.2 | 85.4 |
| Ex. 81 | cinnolinyl | —SO$_2$— | —N(CH$_3$)—(CH$_2$)$_2$—(3,4-dimethoxyphenyl) | 19.2 | 73.1 | 86.6 |

By ways of comparison, the following results were obtained with known compounds:

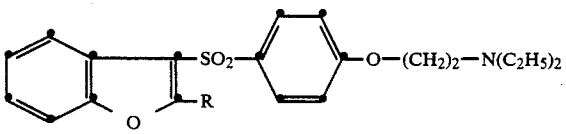

| | | % of the maximum contractional effect | | |
|---|---|---|---|---|
| Compound | R | $10^{-6}M$ | $10^{-7}M$ | $10^{-8}M$ |
| A | n-C$_4$H$_9$— | 25 | 60.3 | 84.3 |
| B | —C$_2$H$_5$ | 52.2 | 84.9 | — |

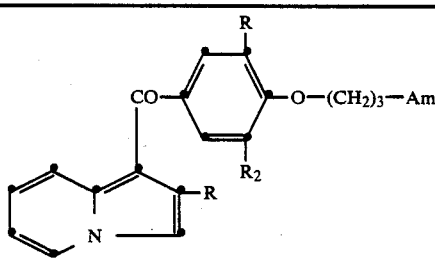

| | | | | | % of the maximum contractional effect | |
|---|---|---|---|---|---|---|
| Compound | R | R$_1$ | R$_2$ | Am | $10^{-6}M$ | $10^{-7}M$ |
| Compound C | n-C$_4$H$_9$ | H | H | —N(n-C$_4$H$_9$)$_2$ | 25.0 | 74.4 |
| Compound D | —C$_2$H$_5$ | CH$_3$ | CH$_3$ | —N(n-C$_4$H$_9$)$_2$ | 19.3 | 64.7 |

-continued

| Compound E | —C₂H₅ | H | H | —N(n-C₃H₇)₂ | 37.9 | 89.1 |

Establishing an activity ratio between the compounds of the invention and the corresponding compounds of the prior art, the following results were obtained:

| Compounds | Activity ratio |
|---|---|
| Compound (Ex. 7) Compound E | 6.0 |
| Compound (Ex. 13) Compound C | 2.0 |
| Compound (Ex. 10) Compound D | 2.2 |

These results show the superiority of the compound of the invention over the corresponding compounds of the prior art.

II. Antiadrenergic Properties

The object of this test is to determine the capacity of the compounds of the invention for reducing the increase in epinephrine-induced increase in blood-pressure (anti-α effect) and the isoprenaline-induced acceleration in heart rate (anti-β effect), in dogs previously anaesthatized with pentobarbital and atropinized.

For each dog, the dose of epinephrine (between 3 and 10 μg/kg) which induced a reproducible increase in the blood-pressure of approximately 133×10² Pa and the dose of isoprenaline (1 to 2 μg/kg) which induced a reproducible increase in the heart rate of approximately 70 beats/min. were first determined. The dose of epinephrine and of isoprenaline, determined in this manner, were injected alternately every ten minutes and, after two successive reference responses had been obtained, an amount of the test compound was administered intravenously.

Anti-α Effect

The percentage reduction in the hypertension induced by the test compound compared with the reference hypertension previously obtained (approximately 100 mm Hg) was recorded.

Anti-β Effect

The percentage reduction in the acceleration of the heart rate induced by the test compound compared with the reference tachycardia measured previously (approximately 70 beats) was recorded.

In both cases, the results of the reduction in blood-pressure or in the heart rate have been expressed as follows:

+ for a reduction < 50%
++ for a reduction ≧ 50%
+++ for a reduction sub-total (almost complete reduction).

The following results were recorded:

| Compound | Dose (mg/kg) | anti-α effect | anti-β effect |
|---|---|---|---|
| Ex. 7 | 5 | +++ | +++ |
| Ex. 8 | 0.5 | ++ | + |
| Ex. 9 | 1 | ++ | ++ |
| Ex. 26 | 0.5 | +++ | ++ |
| Ex. 20 | 5 | +++ | +++ |
| Ex. 21 | 5 | +++ | +++ |
| Ex. 2 | 5 | +++ | ++ |

-continued

| Compound | Dose (mg/kg) | anti-α effect | anti-β effect |
|---|---|---|---|
| Ex. 27 | 1 | +++ | ++ |
| Ex. 28 | 0.1 | +++ | ++ |
| Ex. 23 | 1 | +++ | +++ |
| Ex. 11 | 1 | ++ | ++ |
| Ex. 12 | 5 | ++ | +++ |
| Ex. 13 | 5 | ++ | ++ |
| Ex. 29 | 5 | +++ | ++ |
| Ex. 14 | 2.5 | +++ | +++ |
| Ex. 15 | 2.5 | +++ | +++ |
| Ex. 17 | 1.3 | +++ | ++ |
| Ex. 30 | 0.1 | +++ | +++ |
| Ex. 1 | 0.5 | ++ | ++ |
| Ex. 42 | 0.1 | +++ | +++ |
| Ex. 43 | 0.2 | +++ | +++ |
| Ex. 45 | 0.1 | ++ | ++ |
| Ex. 46 | 0.1 | +++ | +++ |
| Ex. 47 | 0.3 | ++ | + |
| Ex. 49 | 1 | +++ | ++ |
| Ex. 50 | 0.1 | +++ | +++ |
| Ex. 51 | 5.2 | +++ | ++ |
| Ex. 52 | 5.4 | +++ | ++ |
| Ex. 53 | 6.1 | +++ | + |
| Ex. 55 | 0.13 | +++ | ++ |
| Ex. 59 | 11.2 | ++ | ++ |
| Ex. 63 | 10.1 | +++ | ++ |
| Ex. 64 | 4.9 | + | ++ |
| Ex. 65 | 5.89 | ++ | ++ |
| Ex. 66 | 0.1 | +++ | + |
| Ex. 67 | 1.3 | +++ | + |
| Ex. 68 | 0.6 | +++ | ++ |
| Ex. 69 | 1.2 | +++ | ++ |
| Ex. 70 | 0.12 | ++ | + |
| Ex. 71 | 0.13 | +++ | ++ |
| Ex. 72 | 0.52 | ++ | + |
| Ex. 73 | 3 | +++ | ++ |
| Ex. 74 | 1.2 | +++ | + |
| Ex. 75 | 1.3 | +++ | + |
| Ex. 76 | 0.13 | +++ | + |
| Ex. 77 | 3 | +++ | ++ |

By way of comparison, the known compounds showed the following antiadrenergic effects:

| Compound | Dose (mg/kg) | anti-α effect | anti-β effect |
|---|---|---|---|
| Compound A | 10 | + | 0 |
| Compound B | 10 | +++ | + |
| Compound C | 10 | + | 0 |
| Compound D | 10 | + | + |
| Compound E | 10 | + | ++ |
| Compound F* | 10 | − | 0 |

*2-ethyl-1-{4-[3-(di-n-butylamino)-propyloxy]benzoyl}-indolizine.

These results demonstrate that the compounds of the invention show much greater α- and β-antiadrenergic activity than those of the compounds of the prior art.

III. Toxicity The acute toxicity of the compounds of the invention was determined intravenously in mice according o the method of Litchfield and Wilcoxon (J. Pharm. Exp. Therap. 1946, 96, 99).

The following results were obtained, expressed in the form of the LD₅₀, compared with a benzoylindolizine derivative, in this case 2-ethyl-3-{4-[3-(di-n-butylamino) propyloxy]benzoyl}indolizine or butoprozine.

| Compound | LD$_{50}$ (mg/kg) |
|---|---|
| Ex. 6 | 31 |
| Ex. 11 | 28 |
| Ex. 7 | 26 |
| Ex. 18 | 35 |
| Ex. 19 | 60 |
| Ex. 13 | 31 |
| Ex. 9 | 55 |
| Ex. 28 | 32 |
| Ex. 30 | 140 |
| Butoprozine | 23 |

The results show that the compounds of the invention compare favourably with butoprozine as regards toxicity.

The therapeutic compositions according to the invention can be presented in any form suitable for administration in human or veterinary therapy. As regards the administration unit, this can take the form of, for example, a coated- or uncoated tablet, hazd- or soft-gelatin capsule, packaged powder, susoension or syrup for oral administration, a suooository for rectal administration or a solution or suspension for parenteral administration.

The therapeutic compositions of the invention may contain, per administration unit, for example, from 50 to 500 mg as the weight of active ingredient for oral administration, from 50 to 100 mg of active ingredient for rectal administrat on and from 50 to 150 mg of active ingredient for parenteral administration.

Depending on the administration route chosen, the theraceutical veterinary compositions of the invention will be prepared by combining at least one of the compounds of formula I, or a non-toxic addition salt of his compcund, ith a suitable excipient, it being possible for the latter to consist, for example, of at least one ingredien: selected from the following substances: lactose, starches, talc, magnesium stearate, polyvinylpyrrolidone, alginic acid, colloidal silica, distilled water, benzyl alcohol or sweetening agents.

The following non-limiting examples illustrate the invention:

EXAMPLE 1

Preparation of
2-isopropyl-1-{-4-[3-(di-n-butylamino)propyloxy]benzenesulphonyl}-indolizine oxalate (SR 33513 A)

(a)
2-isopropyl-1-(4-tosyloxybenzenesulohonyl)indolizine

A mixture of 0.05 mol of 4-tosyloxyphenyl β-8picolyl sulphone, 0.15 mol of 1-bromo-3-methyl-2-butanone and 0.05 mol of potassium carbonate in 100 ml of methyl ethyl ketone wasbrought to reflux for 22 hours. After this period of time, the reaction medium was brought back to room temperature and then filtered. The filtrate was evaporated carefully under vacuum so as to drive off the excess bromo ketone. The pasty residue was- taken up in petroleum ether, ground and filtered. The last traces of bromo ketone were thereby removed.

The cake obtained was taken up in a mixture of 200 ml of acetone/water (70:30), acidified with a few drops of hydrochloric acid and then brought to boiling for a few minutes. After cooling and filtration, a white solid was isolated which could be recrystallized in an acetone/water mixture.

In this manner, 2-isopropyl-1-(4-tosyloxybenzenesulphonyl) indolizine was obtained in a 70% yield. M.p. 180–183° C.

From suitable starting substances and using the process described above, the following compounds were prepared :
2-Methyl-1-(4-tosyloxybenzenesulphonyl)indolizine M.P. 169° C. (acetone)
2-Ethyl-1-(4-tosyloxybenzenesulphonyl)indolizine M.P. 190° C. (acetone)
2-n-Propyl-1-(4-tosyloxybenzenesulphonyl)indolizine M.P. 189° C. (acetone)
2-Ethyl-1-(3-methyl-4-tosyloxybenzenesulphonyl)indolizine M.P. 164° C. (methanol/chloroform)
2-n-Butyl-1-(4-tosyloxybenzenesulphonyl)indolizine M.P. 145° C. (acetone)
2-Phenyl-1-(4-tosyloxybenzenesulphonyl)indolizine M.P. 168° C. (dichloroethane)
2-Ethyl-1-(3,5-dimethyl-4-tosyloxybenzenesulphonyl)indolizine M.P. 161° C. (acetone)
2-tert-Butyl-1-(4-tosyloxybenzenesulphonyl)indolizine Oily
2-Cyclohexyl-1-(4-tosyloxybenzenesulphonyl)indolizine M.P. 173–175° C. (acetone/water)

(b)
2-Isopropyl-1-(4-hydroxybenzenesulphonyl)indolizine 0.034 mol of 2-isopropyl-1-(4-tosyloxybenzenesulphonyl)indiolizine were poured into a mixture of 80ml of water containing 0.34 mol of sodium hydroxide and 80ml of ethanol, and the reaction mixture was then brought to reflux for 24 hours.

After being cooled, the solution was diluted with 300ml of water and then extracted with ethyl ether. After acidification of the aqueous phase, the formation of a precipitate was observed, and this was suction-filtered and dried.

In this manner, 2-isopropyl-1-(4-hydroxybenzenesulphonyl) indolizine was obtained in a 90% yield. M.P. 179–180° C. (isopropanol/water, 3:1).

From suitable starting substances and using the process described above, the following compounds were prepared:
2-Methyl-1-(4-hydroxybenzenesulphonyl)indolizine M.P. 177° C. (methanol/water)
2-Ethyl-1-(4-hydroxybenzenesulphonyl)indolizine M.P. 204° C. (ethyl acetate)
2-n-Propyl-1-(4-hyroxybenzenesulphonyl)indolizine M.P. 225° C. (isopropanol)
2-Ethyl-1-(3-methyl-4-hydroxybenzenesulphonyl)indolizine M.P. 214° C. (isopropanol)
2-n-Butyl-1-(4-hydroxybenzenesulphonyl)indolizine M.P. 190° C. (isopropanol)
2-Phenyl-1-(4-hydroxybenzenesulphonyl)indolizine M.P. 234° C. (methanol)
2-Ethyl-1-(3,5-dimethyl-4-hydroxybenzenesulphonyl)indolizine M.P. 183° C. (isopropanol)
2-tert-Butyl-1-(4-hydroxybenzenesulphonyl)indolizine M.P. 169° C. (chloroform/petroleum ether)
2-Cyclohexyl-1-(4-hydroxybenzenesulphonyl)indolizine M.P. 217° C. (isopropanol/petroleum ether)

(c)
2-Isopropyl-1-{4-[3-(di-n-butylamino)propyloxy]-benzenesulphonyl}indolizine oxalate.

0.015 mol of 1-chloro-3-(di-n-butylamino)propane and 0.018 mol of a finely ground potassium carbonate were added to 0.012 mol of 2-isopropyl-1-(4-hydroxybenzenesulphonyl)indolizine in 100 ml of methyl ethyl ketone. The mixture was brought to reflux for 24 hours and then brought back to room-temperature. The inorganic salts were filtered off and the filtrate was evaporated under the vacuum of a filter pump. An oil was obtained which was purified by chromatography on a dry alumina column.

The desired compound, in basic form, thus purified could be isolated in the crystalline state. The oxalate of the product obtained was formed by adding a stoechiometric amount of oxalic acid to a solution of the base dissolved in acetone.

In this manner, 2-isopropyl-1-{4-[3-(di-n-butylamino)propyloxy]benzenesulphonyl}indolizine oxalate was obtained in a 26% yield.

M.P. 133° C. (isopropanol)
2-Cyclohexyl-1-{4-[3(di-n-butylamino)propyloxy]-benzensulphonyl}indolizine
M.P. 130–131° C. (methanol) (SR 33641) (Example 51)

EXAMPLE 2

Preparation of 2-ethyl-1-[4-(3-piperidinopropyloxy)benzenesulphonyl]indolizine hydrochloride (SR 33528 A)

(a)
2-Ethyl-1-[4-(3-bromopropyloxybenzenesulphonly]indolizine 0.01 mol of 2-ethyl-1-(4-hydroxybenzenesulphonyl)indolizine was dissolved in 50 ml of methyl ethyl ketone. 0.02 mol of potassium carbonate was added and the mixture was brought to reflux for one hour. 0.04 mol of 1,3-dibromopropane was then added and refluxing was continued for 24 hours. After the reaction, the salts were removed by filtration and the solution was evaporated to dryness. The residue was purified by chromatography on a silica column (elution solvent:dichloroethane).

In this manner, 2-ethyl-1-[4-(3-bromopropyloxy)benzenesulphonyl]indolizine was obtained in a 70% yield. M.P. 136° C. (acetone)

From suitable starting substances and using the process described above, the following compounds were obtained:

2-n-Butyl-1-[4-(3-bromopropyloxy)benzenesulphonyl]indolizine M.P. 119° C. (acetone)
2-Isopropyl-1-[4-(3-bromopropyloxy)benzenseulphonyl]indolizine M.P. 131° C. (acetone)
2-Phenyl-1-[4-(3-bromopropyloxy)benzenesulphonyl]indolizine M.P. 199° C. (dichloroethane)
2-Ethyl-1-[4-(2-bromoethyloxy)benzenesulphonyl]indolizine Oily
2-Ethyl-1-[4-(4-bromobutyloxy)benzenesulphonyl]indolizine M.P. 111° C. (cyclohexane)
2-Isopropyl-1-[4-(4-bromobutoxy)benzenesulphonyl]indolizine M.P. 111° C. (ethyl acetate/petroleum ether)
2-Phenyl-1-[4-(3-bromopropyloxy)-3-methylbenzenesulphonyl]indolizine Oily b()
2-Ethyl-1-[4-(3-piperidinopropyloxy)benzenesulphonyl]indolizine hydrochloride 0.005 mol of 2-ethyl-1-[4-(3-bromopropyloxy)-benzenesulphonyl]indolizine was dissolved in 25ml of butanol. 0.01 mol of potassium carbonate and 0.01 mol of piperidine were added and the reaction mixture was then heated on a water bath for 20 hours.

After this period of time, the mixture was evaporated to dryness under vacuum, and an oil was thereby obtained which was taken up in ethyl ether. An insoluble material composed of salts was removed, and the ether solution was evaporated to dryness. The residue was purified by chromatography on a silica column using a chloroform/methanol (8:2) mixture as solvent, and the pure oil obtained was dissolved in a mixture of acetone and ethyl ether.

The hydrochloride was then formed by adding a solution of hydrochloric acid in ethyl ether.

In this manner, 2-ethyl-1-[4-(3-piperidinopropyloxy)benzenesulphonyl]indolizine hydrochloride was obtained. Yield : 54% M.P. 183° C. (acetone)

EXAMPLE 3

Preparation of 2-ethyl-1-{4-[3-(tert-butylamino)propyloxy]benzenesulphonyl}-indolizine hydrochloride. (SR 33511 A)

A mixture of 0.007 mol of 2-ethyl-1-[4-(3-bromopropyloxy) benzenesulphonyl]indolizine and 0.07 mol of tert-butylamine in 50ml of toluene was heated on a water bath at 100° C. for 48 hours.

After the reaction, the mixture was carefully evaporated to dryness under vacuum, and the residue taken up in aqueous sodium hydroxide solution. The mixture was extracted with dichloromethane and the organic phase was evaporated to dryness. An oily residue was obtained, which was purified by chromatography on a dry silica column, using a dichloromethane/methanol/ammonia mixture as solvent.

The purified desired compound in basic form was taken up in ethyl acetate, and the hydrochloride was formed by adding hydrochloric acid, dissolved in ethyl ether, dropwise thereto.

In this manner, 2-ethyl-1-{4-[3-(tert-butylamino) propyloxy]benzenesulphonyl}indolizine hydrochloride was obtained.

Yield: 68%
M.p. 229–231° C. (ethyl acetate/methanol)

From suitable starting substances and using the processes described in the above examples, the follo.ing compounds .ere prepared:

2-Methyl-1-{4-[3-(diethylamino)propyloxy]benzenesulphonylyl}indolizine oxalate (SR 33520 A) (Example 4) M.p. 153° C. (dichloro ethane/methanol)
2-Methyl-1-{4-[3-(di-n-propylamino)propyloxy]benzenesulphonyl}indolizine (SR 33518) (Example 5) M.p. 107–108° C. (methanol)
2-Methyl-1-{4-[3-(di-n-butylamino)propyloxy]benzenesulphonyl}indolizine oxalate (SR 33133 A) (Example 6) M.p. 131° C. (ethyl acetate)
2-Ethyl-1-{4-[3-(di-n-propylamino)propyloxy]benzenesulphonyl}indolizine hydrochloride (SR 33305 A) (Example 7) M.p. 192° C. (acetone)
2-Ethyl-1-{4-[3-(di-n-butylamino)propyloxy]benzenesulphonyl}indolizine hydrochloride (SR 33306 ) Example 8) M.p. 153° C. (acetone)
2-Ethyl-1-{4-[3-(di-n-butylamino)propyloxy]-3-methylbenzenesulphonyl}indolizine hydrochloride (SR 33508 A) (Example 9) M.p. 200–203° C. (methyl ethyl ketone/methanol)
2-Ethyl-1-{4-[3-(di-n-butylamino)propyloxy]-3,5-dimethylbenzenesulphonyl}indolizine hydrochloride (SR 33538 A) (Example 10) M.p. 136–137° C. (ethyl acetate/methanol)

2-n-Propyl-1-{4-[3-(di-n-butylamino)propyloxy]benzenesulphonyl}indolizine oxalate (SR 33220 A) (Example 11) M.p. 111° C. (isopropanol)

2-n-Butyl-1-{4-[3-(di-n-propylamino)propyloxy]benzenesulphonyl}indolizine oxalate (SR 33507 A) (Example 12) M.p. 110-113° C. (isopropanol)

2-n-Butyl-1-{4-[3-(di-n-butylamino)propyloxy]benzenesulphonyl}indolizine oxalate (SR 33504 A) (Example 13) M.p. 85-87° C. (ethyl acetate)

2-Isopropyl-1-{4-[3-dimethylamino)propyloxy]benzenesulphonyl}indolizine (SR 33517) (Example 14) M.p. 90-92° C. (diisopropyl ether/diethyl ether)

2-Isopropyl-1-{4-[3-(diethylamino)propyloxy]benzenesulphonyl}indolizine (SR 33516) (Example 15) M.p. 90-92° C. (diisopropyl ether)

2-tert-Butyl-1-{4-[3-(di-n-butylamino)propyloxy]benzeneuslphonyl}indolizine (SR 33541) (Example 16) M.p. 90-92° C. (hexane)

2-Isopropyl-1-{4-[3- (di-n-propylamino)propyloxy]benzenesulphonyl}indolizine oxalate (SR 33512 A) (Example 17 ) M.p. 164-165° C. (methyl ethyl ketone/methanol)

2-Phenyl-1{4-[3-di-n-butylamino)propyloxy]benzenesulphonyl}indolizine hydrochloride (SR 33369 A) (Example 18) M.p. 158° C. (acetone)

2-Phenyl-1-{4-[3-(di-n-butylamino)propyloxy]-3-methylbenzenesulphonyl}indolizine hydrochloride (SR 33486 A) (Example 19 ) M.p. 194° C. (methanol)

2-Ethyl-1-{4-[3-(di-n-butylamino)propyloxy]benzenesulphonyl}indolizine oxalate (SR 33533 A) (Example 20) M.p. 163° C. (acetone)

2-Ethyl-1-{4-[3-(n-butylamino)propyloxy]benzenesulphonyl}indolizine oxalate (SR 33534 A) (Example 21 ) M.p. 141° C. (acetone)

2-Ethyl-1-{4-[2-(di-n-butylamino)ethyloxy]benzenesulphonyl}indolizine hydrochloride (SR 33547 A) (Example 22) M.p. 153° C. (ethyl acetate)

2-Ethyl-1-{4-[4-(di-n-butylamino)butyloxy]benzenesulphoneyl}indolizine hemioxalate (SR 33548 A) (Example 23) M.p. 150° C. (ethyl acetate)

2-Phenyl-1-{4-[3-(tert-butylamino)propyloxy]benzenesulphonyl}indolizine hydrochloride (SR 33370 A) (Example 24) M.p. 228° C. (acetone)

2-Phenyl-1-{4-[3-(tert-butylamino)propyloxy]-3-methylbenzenesulphonyl}indolizine hydrochloride (SR 33485 A) (Example 25) M.p. b 181° C. (methanol)

2-Ethyl-1-{4-[3-(di-n-pentylamino)propyloxy]benzenesulphonyl}indolizine hydrochloride (SR 33550 A) (Example 26) M.p. 132-144° C. (ethyl acetate/methanol)

2-Ethyl-1-{4-[3-(3,4-dimethoxy-β-phenethylamino)-propyloxy]benzenesulphonyl}indolizine oxalate (SR 33544 A) (Example 27) M.p. 179-181° C. (methanol)

2-Ethyl-1-[4-{3-[N-methyl-N-(3,4-dimethoxy-β-phenethyl)amino]propyloxy}benzenesulfphonyl]-indolizine (SR 33549) (Example 28) M.p. 78-80° C. (diisopropyl ether)

2n-Butyl-1-{4-[3-(tert-butylamino)propyloxy]benzenesulphonyl}indolizine oxalate (SR 33503 A) (Example 29) M.p. 207-208° C. (methanol)

2-Isopropyl-1-[4-{3-[N-methyl-N-(3,4-dimethoxy- β-phenethyl)amino]propyloxy}benzenesulphonyl-]indolizine (SR 33557) (Example 30) M.p. 82-83° C. (diisopropyl ether/dichloromethane)

2-Isopropyl-1-{4-[3-(β-phenethylamino)propyloxy]benzenesulphonyl}indolizine hydrochloride (SR 33577 A) (Example 31) M.p. 209-210° C. (ethyl acetate/methanol)

2-Isopropyl-1-{4-[3-(benzylamino)propyloxy]benzenesulphonyl}indolizine hydrochloride (SR 33578 A) (Example 32) M.p. 193-195° C. (ethyl acetate/methanol)

2-Isopropyl-1{4-[3-(N-phenylpiperazino)propyloxy]-benzenesulphonyl}indolizine (SR 33579) (Example 33) M.p. 135-136° C. (methanol/dichloromethane)

2-Isopropyl-1-{4-[3-(2-pyridylethylamino)propyloxy]-benzenesulphonyl}indolizine dioxalate (SR 33582 A) (Example 34) M.p. 154-156° C. (methanol)

2-Isopropyl-1-{4-[3-(4-phenylpiperidino)propyloxy]-benzenesulphonyl}indolizine (SR 33583) (Example 35) M.P. 79-80° C. (methanol)

2-Isopropyl-1-{4-[3-(di-n-octylamino)propyloxy]-benzenesulphonyl}indolizine (SR 33584) (Example 36) M.P. <50° C. (pasty)

2-Isopropyl-1-{4-[3-(di-n-pentylamino)propyloxy]-benzenesulphonyl}indolizine hydrochloride (SR 33603 A)(Example 37) M.P. 138° C. (methyl ethyl ketone-/ethyl ether, 2:1)

2-Ethyl-1-{4-[3-(1-imidazolyl)propyloxy]benzenesulphonyl}indolizine (SR 33590) (Example 38) M.P. 130-131° C. (ethyl acetate/methanol/ethyl ether)

2-Isopropyl-1-{4-[4-(di-n-butylamino)butyloxy]benzenesulphonyl}indolizine (SR 33606)(Example 39) M.P. 96° C. (n-hexane)

2-Ethyl-1-{4-[5-(di-n-butylamino)pentyloxy]benzenesulphonyl}indolizine (SR 33607)(Example 40) M.P. 89-90° C. (n-hexane)

2-Isopropyl-1-[4-{3-[N-methyl-N-(3,4-dimethoxybenzyl)-amino]propyloxy-}benzenesulphonyl]indolizine (SR 33611)(Example 41) M.P. 96-100° C. (diisopropyl ether/dichloromethane)

2Isopropyl-1-[4-{4-[N-methyl-N-(3,4-dimethoxy-β-phenethyl) amino]butyloxy}benzenesulphonyl]indolizine (SR 33620)(Example 42) M.P 84-86° C. (hexane)

2-Isopropyl-1-{4-[3-(3,4-dimethoxybenzyl amino)-propyloxy]benzenesulphonyl}indolizine (SR 33621)(Example 43) M.P. 109-11120 C. (diisopropyl ether/dichloroethane)

2-Isopropyl-1-{4-[3-(3,4-dimethoxyanilino)propyloxy]-benzenesulphonyl}indolizine hydrochloride (SR 33624 A) (Example 44) M.P. 200-203° C. (methylene chloride)

2-Isopropyl-1-[4-{3-[N-n-butyl-N-(3,4-dimethoxy-β-phenethyl) amino]propyloxy}benzenesulphonyl]indolizine acid oxalate (SR 33629 A) (Example 45) M.P. 108-110° C. (ethyl acetate/methanol)

2-Isopropyl-1-[4-{3-[N-methyl-N-(3-methoxy-β-phenethyl)amino]propyloxy}benzenesulphonyl]indolizine acid oxalate (SR 33632 A) (Example 46) M.P. 111-113° C. (ethyl acetate/methanol)

2-Isopropyl-1-[4-{3-[N-methyl-N-(4-methoxy-β-phenethyl)amino]propyloxy}benzenesulphonyl]indolizine acid oxalate (SR 33638 A) (Example 47) M.P.140-144° C. (ethyl acetate/methanol)

2-Isopropyl-1-{4-[3-(4-diphenylmethylpiperazino)-propyloxy]benzenesulphonyl}indolizine (SR 33663 A)(Example 48) M.P. 170° C. (methanol/dichloromethane)

EXAMPLE 49

Preparation of
2-isopropyl-1-4-[3-(di-n-butylamino)2-hydroxy-propyloxy]-benzenesulphonyl}indolizine hydrochloride (SR 33644 A)

a()
2-Isopropyl-1-[4-(2,3-epoxypropyloxy)benzenesulphonyl]indolizine

While stirring, a mixture of 0.02 mol of 2-isopropyl-1-(4-hydroxybenzenesulphonyl)indolizine, 0.02 mol of potassium carbonate and 40ml of epichlorohydrin was heated at 90° C. for 20 hours. After this period of time the epichlorohydrin in excess was eliminated under vacuum and the residue was taken up in toluene. The solution was washed with a dilute sodium hydroxide solution then with water. The organic phase was evaporated to dryness under vacuum to obtain an oil which was purified on a silica column (eluent:dichloromethane/ethyl acetate 95/5). The desired product slowly crystallized.

In this manner, 2-isopropyl-1-[4-(2,3-epoxypropyloxy) benzenesulphonyl]indolizine was obtained in a yield of 68%. M.P. 110–111° C.(methanol)

(b)
2-Isopropyl-1-{4-[3-(di-n-butylamino)-2-hydroxy-propyloxy]benzenesulphonyl}indolizine hydrochloride.

A solution of 0.0027 mol of 2-isopropyl-1-[4-(2,3epoxypropyloxy)benzenesulphonyl]indolizine and 0.015 mol of di-n-butylamine in 10 ml of methanol was refluxed for 1 hour. The solution was brought to room-temperature and the di-nbutylamine in excess was eliminated under vacuum together with the solvent. The residue obtained was taken up in anhydrous ethyl ether and the hydrochloride of the desired compound was formed by adding hydrogen chloride in ethyl ether.

In this manner, 2-isopropyl-1-{4-[3-(di-n-hydroxy-propyloxy]-benzenesulphonyl}indolizine hydrochloride was obtained which was recrystallized from an acetone/ethyl ether mixture.

Yield : 68.9%
M.P. 155–156° C.

EXAMPLE 50

Preparation of
2-isopropyl-1-[4-{3-[N-methyl-N-(3,4-dimethoxy-β-phenethyl)amino]-propyloxy}benzenesulphonyl]indolizine hydrochloride (SR 33656 A)

To a solution of 0.075 mol of 2-isopropyl-1-[4-(2,3epoxypropyloxy)benzenesulphonyl]indolizine dissolved in 25 ml of methanol,there were added 0.01 mol of N-methyl-3,4-dimethoxy-β-phenethylamine hydrochloride and 0.01 mol of triethylamine. The mixture was brought to reflux for 5 hours. After cooling the reaction medium was evaporated off to dryness and the oily residue was taken up in dichloromethane and slightly alkaline water.

The organic phase was washed, dried and evaporated off under vacuum. The crude compound so obtained was purified by chromatography on a silica column rendered inactive by means of diethylamine (eluent : dichloromethane). The purified product was dissolved in anhydrous ethyl ether and the hydrochloride of the desired compound was formed by adding hydrogen chloride in ethyl ether. The hydrochloride in question precipitated.

In this manner, 2-isopropyl-1-[4-{3-[N-methyl-N-(3,4-dimethoxy-βphenethyl)amino]propyloxy}-benzenesulphonyl]indolizine hydrochloride was obtained.
M.P. 110° C.

EXAMPLE 52

Preparation of
1-{4-[3-(di-n-butylamino)propyloxy]phenylthio}-2-isopropylindolizine oxalate (SR 33650 A)

(a)
1-(3-Methyl-2-oxobutyl)-2-{[(4-hydroxyphenyl)thio]-methyl}pyridinium bromide A mixture of 0.02 mol of 2-{[(4-hydroxyphenyl)thio]-methyl}pyridine and 0.03 mol of bromomethylisopropylketone in 160ml of acetone was heated to boiling for 24 hours. After this period of time, the reaction medium was brought to room-temperature. A precipitate was observed which increased by adding pure diethyl ether. This precipitate was filtered out washed with dry diethyl ether and dried under vacuum.

In this manner, 1-(3-methyl-2-oxobutyl)-2-{[(4-hydroxyphenyl)thio]methyl}pyridinium bromide was obtained in crude form and used as such.

Yield : 65%
M.P. 175° C.

1-[(4-Hydroxyphenyl)thio]-2-isopropylindolizine

The pyridinium bromide obtained in paragraph (a) above was dissolved in water and sodium bicarbonate in excess was added to this solution. The mixture was heated at 90° C. for 25 minutes and then brought to room-temperature.

An oil was so obtained which was washed with water by decantation. This oil was then dissolved in methanol, the methanolic solution was filtered and evaporated to dryness. The crude product so obtained was purified by chromatography on a silica column (eluent : dichloroethane/hexane 1/1).

In this manner, 1-[(4-hydroxyphenyl)thio]-2-isopropylindolizine was obtained.

Yield : 90%
M.P 100° C.

1-{4-[3-Di-n-butylamino)propyloxy]phenylthio}-2-isopropylindolizine oxalate

Into a solution of 0.01 mol of 1-[(4-hydroxyphenyl)-thio]- (). 2-isopropylindolizine in 80ml of dimethylsulphoxide, there were added 5g of anhydrous potassium carbonate and 0.015 mol of 1-chloro-di-n-butylamino-propane. The reaction medium was maintained under stirring for 24 hours and then poured into 500 ml of water. The solution was extracted with diethyl ether and the organic phase was washed with water, dried on sodium sulphate, filtered and evaporated to dryness to obtain the desired product in basic form. This crude compound was dissolved in dry diethyl ether and a solution of oxalic acid in diethyl ether was added.

In this manner, 1-{4-[3-(di-n-butylamino)propyloxy]-phenylthio}-2-isopropylindolizine oxalate was obtained in a yield of 65%.
M.P. 118° C. (ethanol/diisopropyl ether).

Using the same method as that described above but starting from the appropriate product, the following compound was prepared:

1-[4-{3-[N-methyl-N-(3,4-dimethoxy-β-phenethyl-
)amino]propyloxy}phenylthio]-2-isopropyl-indoli-
zine oxalate (SR 33651) (Example 53) M.P. 1110° C.

EXAMPLE 54

Preparation of 4-[3-(di-n-butylamino)propyl]oxypheny
(2-isopropyl-1-indolizinyl)sulphoxide oxalate (SR
33644).

Into a solution of 0.0017 mol of 1-{4-[3-(di-n-butylamino) propyloxy]phenylthio}-2-isopropylindolizine oxalate, obtained in Example 52, in 10 ml of methylene chloride, was added, drop-by-drop at the temperature of 0° C., a solution of 0.0019 mol of 3-chloroperbenzoic acid in 10 ml of methylene chloride. The reaction medium was allowed to return to room-temperature and the reaction was maintained for 15 minutes.

The medium was twice washed with an aqueous solution of sodium bicarbonate then with water. The organic phase was dried on sodium sulphate! filtered and evaporated to dryness to obtain the desired product in basic form.

This crude compound was dissolved in dry diethyl ether and a solution of oxalic acid in diethyl ether was added.

In this manner, 4-[3-(di-n-butylamino)propyl]oxyphenyl (2-isopropyl-1-indolizinyl)sulphoxide oxalate was obtained in a yield of 20%. M.P. 70° C.

EXAMPLE 55

Preparation of
2-isopropyl-3-[4-{3-[N-methyl-N-(3,4-dimethoxy-β-phenethyl) amino]propyloxy}benzenesulphonyl]
indolizine oxalate (SR 33700 A) a)
1-Ethoxycarbonyl-2-isopropyl-3-(4-methoxybenzenesulphonyl) indolizine Into 114 ml of 1,2-dichloroethane were dissolved 13.4 g (0.058 mol) of 1-carboethoxy-2-isopropylindolizine and 12.7 g (0.061 mol) of 4-methoxybenzenesulphonyl chloride. The solution was stirred and cooled to 0° C. while 23 g (0.174 mol) of aluminium chloride were added by small fractions.

The addition was terminated after 30 min and the medium was allowed to return to room-temperature for 4 hours. After that, the mixture was poured onto ice and 20 ml of concentrated hydrochloric acid were added. The medium was stirred for 30 min and the organic layer was decanted and washed with 3 fractions of water. The extract was dried on sodium sulphate and isolated under vacuum to obtain 24.8 g of a black oil (theory : 23.28 g). This oil was purified on a silica column using first n-hexane/10%-ethyl acetate and then n-hexane/20%-ethyl acetate as eluents.

In this manner 3.25 g of 1-ethoxycarbonyl 2-isopropyl-3-(4-methoxybenzenesulphonyl) indolizine were obtained in a form of a white solid.

Yield : 13.95%.

M.P. 103–104° C.(hexane/methylene chloride).

(b)
1-Carboxy-2-isopropyl-3-(4-hydroxybenzenesulphonyl) indolizine Into 100 ml of methylene chloride and 25 ml of ethanethiol, were suspended 6.7 g (0.050 mol) of aluminium chloride. The suspension was stirred and cooled to 0° C. while 2.5 g of
1-ethoxycarbonyl-2-isopropyl-3(4-methoxybenzenesulphonyl) indolizine in methylene chloride were added. The addition took about 15 min . The reaction medium was allowed to return to room-temperature and maintained, at this temperature, for 5 min . After pouring onto ice, 5 ml of concentrated hydrochloric acid were added while stirring and the medium was extracted with 2 fractions of ethyl ether. The ethereal extracts were collected and washed with 3 fractions of 30 ml of a 10%-aqueous solution of sodium carbonate. The aqueous phase was acidified and a precipitate was observed.

In this manner 1 g of crude 1-carboxy-2 isopropyl-3-(4-hydroxybenzenesulphonyl) indolizine was obtained in the form of a beige solid.

Yield: 44.6%

(c) 2-Isopropyl-3-(4-hydroxybenzenesulphonyl)
indolizine

For 2 min, 1 g (2.78 x 10-3 mol) of 1-carboxy-2-isopropyl-3-(4-hydroxy-benzenesulphonyl) indolizine was heated at 200° C. The black residue so obtained was taken up in methylene chloride and a slight precipitate was eliminated by filtration. The filtrate was evaporated to provide 0.8 g of a brown oil (theory:0.877 g). This oil was purified on a silica column using a methylene chloride/ethyl acetate 95/5 mixture as eluent and 0.6 g of a green oil was isolated.

In this manner 2-isopropyl-3-(4-hydroxybenzenesulphonyl) indolizine was obtained.

Yield: 68.4%.

Purity : 97.5%.

(d)
2-Isopropyl-3-[4-{3-[N-methyl-N-(3,4-dimethoxy-β-phenethyl)amino]propyloxy}benzene-sulphonyl]
indolizine oxalate At room-temperature, 0.510 g (1.57×10$^{-3}$ mol) of 2-isopropyl-3-hydroxybenzenesulphonyl) indolizine, 0.5 g of potassium carbonate and 5 ml of dimethylsulphoxide were stirred for 30 min. To this mixture 0.524 g (1.45×10$^{-3}$ mol) of 1-chloro-3-[N-methyl-N-(3,4-dimethoxy-β-phenethyl)amino] propane acid oxalate was added. The stirring was maintained for 16 h at room-temperature then for 2 h at 50° C. The dimethylsulphoxide was eliminated under vacuum and the residue was taken up in water. The medium was then twice extracted with ethyl acetate. After that theextracts were twice washed with water and dried on sodium sulphate. After filtration, the filtrate was evaporated under vacuum to obtain 0.845 g of an amber-colouredoil. This oil was purified on a silica column using as eluents, ethyl acetate containing 5%, then 10%, then 20%-methanol to provide 0.583 g of desired product in free base form (yield : 73%; purity : 99.4%).

The oxalate was formed using 0.530 g of base so obtained and an ethereal solution of oxalic acid. The oxalate was recrystallized from ethyl acetate/methanol/ethyl ether.

In this manner 0.473 g of 2-isopropyl-3-[4-{3-[N-methyl-N-(3,4-di- methoxy-β-phenethyl)-amino]- propyloxy}benzenesulphonyl] indolizine oxalate was obtained in the form of a white solid.

M.P.: 135–137° C.

EXAMPLE 56

Preparation of
4-{4-[3-(di-n-butylamino)propyloxy]phenylthio)}pyridine dioxalate (SR 33683 A)

(a) 4-(4-Hydroxy-phenylthio)pyridine

A mixture of 0.0386 mol of 4-(4-methoxy-phenylthio)pyridine hydrochloride in 100 ml of 47% - hydrobromic acid was heated to boiling for 6 hours. The hydrobromic acid in excess was then distilled off using a rotatory evaporator and the residue was taken up in water. The solution was twice washed with ethyl ether and neutralized with a sodium hydroxide aqueous solution. The precipitate which formed was filtered out, washed with water and dried under vacuum at the temperature of 60° C.

In this manner 4-(4-hydroxy-phenylthio) pyridine was obtained in a yield of 96%.

M.P.: 240° C.(heptane/isopropanol 6/4).

(b) 4-{4-[3-(Di-n-butylamino)propyloxy]phenylthio}pyridine dioxalate

A solution of 0.014 mol of 4-(4-hydroxy-phenylthio) pyridine and 3 g of finely crushed anhydrous potassium carbonate in 50 ml of dimethylsulphoxide was placed under stirring for 30 min. To this medium 0.016 mol of 1-chloro-3-(di-n-butylamino) propane was added and the stirring was maintained at room-temperature for 24 hours. The reaction medium was poured into water and extracted with ethyl ether. The organic phase was washed with water, dried on sodium sulphate and filtered. After the solvent was evaporated off, an oil was provided which was purified by chromatography on a silica column (eluent:methanol). The required compound in free base form so obtained was then transformed into an oxalate by adding an ethereal solution of oxalic acid.

In this manner 4-{4-[3-(di-n-butylamino) propyloxy]-phenylthio}pyridine dioxalate was obtained in a yield of 80%.

M.P.:153° C. (ethanol)

Using the same procedure as that described above, 4-[4-{3-[N-methyl N-(3,4-dimethoxy-β-phenethyl)amino]propyloxy)}phenylthio]pyridine oxalate (SR 33682A) (Example 57) was obtained.

M.P. : 150° C. (ethanol).

EXAMPLE 58

Preparation of
2-{4-[3-(di-n-butylamino)propyloxybenzenesulphonyl} pyridine oxalate (SR 33692 A)

(a) 2-(4-Methoxy-benzenesulphonyl)pyridine

Into 200 ml of dichloromethane was dissolved 0.052 mol of 2-[(4-methoxy phenyl)thio ]pyridine hydrochloride. To this solution, previously cooled to 0° C., a solution of 0.156 mol of 3-chloro-perbenzoic acid in 200 ml of dichloromethane was added drop-by-drop and under stirring. The reaction medium was still maintained under stirring for 15 min at 0° C. and then the temperature was brought to 25° C. The mixture was washed with an aqueous solution of sodium carbonate then with water. The organic phase was dried on anhydrous sodium sulphate, filtered and distilled using a rotatory evaporator. The residue so obtained was purified by chromatography on a silica column using a 1,2-dichloroethane/ethyl acetate 95/5 mixture as eluent.

In this manner 2-(4-methoxy-benzenesulphonyl)pyridine was obtained in a yield of 78%.

M.P. : 112° C.(isopropanol).

Using the same procedure as that described above 4-(4-methoxy-benzenesulphonyl)pyridine was prepared.

M.P. : 104° C.(heptane).

(b) 2-(4-Hydroxy-benzenesulphnyl)pyridine

A mixture of 0.028 mol of 2-(4-methoxy-benzenesulphonyl)pyridine in 70 ml of 47% - hydrobromic acid was heated to reflux for 6 hours. After this period of time, the hydrobromic acid in excess was distilled off. The residue so obtained was taken up in water, washed with ethyl ether, treated with active charcoal and filtered. The aqueous solution was then neutralized with a sodium hydroxide solution and the precipitate which formed, was filtered out and washed with water. The desired product was dried under vacuum at 60° C.and recrystallized from a heptane/ isopropanol 8/2 mixture.

In this manner 2-(4-hydroxy-benzenesulphonyl)pyridine was obtained in a yield of 88%.

M.P. : 148° C.

Using the same method as that described above, 4-(4-hydroxy-benzenesulphonyl)pyridine was prepared.

M.P. : 215° C. (heptane/isopropanol 7/3).

(c) 2-{4-[3-(di-n-butylamino) propyloxy]benzenesulphonyl)}pyridine oxalate

To a solution of 0.0085 mol of 2-(4-hydroxy-benzenesulphonyl)pyridine in 50 ml of dimethylsulphoxide, were added 3 g of finely crushed anhydrous potassium carbonate. The mixture was then maintained under stirring for 30 min and 0.015 mol of 1-chloro-3-( di-n-butylamino)propane was added. Stirring was still maintained for 24 hours and the reaction mixture was then poured into water and extracted with ethyl ether. The organic layer was washed with water, dried on sodium sulphate and filtered. After the filtrate was evaporated, the desired product so obtained was purified by chromatography on a silica column using methanol as eluent. The pure base so obtained was then transformed into an oxalate by addition of oxalic acid in ethyl ether.

In this manner 2-{4-[3-(di-n-butylamino)propyloxy]-benzenesulphonyl} pyridine oxalate was obtained in a yield of 50%.

M.P. : 70° C.(ethyl acetate).

Using the same method as that described above, the following compounds were prepared:

2-[4-{3-[N-methyl-N-(3,4-dimethoxy-β-phenethy)amino]propyloxy}benzenesulphonyl pyridine oxalate (SR 33691 A) (Example 59) M.P. 161.9° C. (ethanol)

4-{4-[3-(di-n-butylamino)propyloxy]benzenesulphonyl)}pyridine dioxalate (SR 33685 A) (Example 60) M.P. : 122° C. (ethyl acetate/ethanol 1/1)

4-[4{3-[N-methyl-N-(3,4-dimethoxy-β-phenethyl)amino]propyloxy}benzenesulphonyl]pyridine oxalate (SR 33680 A) (Example 61) M.P. : 160° C.(ethanol)

EXAMPLE 62

Preparation of 2-{4-[3-(tertiobutylamino)propyloxy]benzenesulphonyl} pyridine oxalate (SR 33693 A)

To a solution of 0.0042 mol of 2-[4-hydroxy-benzenesulphonyl)pyridine in 25 ml of dimethylsulphoxide, was added 1.5 g of finely crushed anhydrous potassium carbonate. The mixture was stirred for 30 min and 0.0075 mol of l-chloro-3-(N-BOC-tertiobutylamino)propane was added. Stirring was maintained for 24 hours and the reaction mixture was then poured into water. After extraction with ethyl ether the organic phase was washed with water, dried on sodium sulphate, filtered and evaporated to dryness. The oily residue so obtained was stirred at the temperature of 185° C. for 20 min and the reaction medium was taken up in water. The mixture was msde alkaline with an aqueous solution of sodium hydroxide and extracted with ethyl ether. The ethereal solution was washed with water, dried on sodium sulphate and filtered. After the solvent was eliminated, a crude product was obtained which was purified by chromatography on a silica column using methanol as eluent. The base so purified was then transformed into an oxalate by adding an ethereal solution of oxalic acid.

In this manner 2-{4-[3-(tertiobutylamino)propyloxy]benzenesulphonyl} pyridine oxalate was obtained in a yield of 23%. M.P. : 147° C.

EXAMPLE 63

Preparation of 4-{3-[N-methyl-N-(3,4-dimethoxy-β-phenethyl)amino]-propyloxy}benzenesulphonylbenzene hydrochloride (SR 33652 A)

(a) (4-Hydroxybenzenesulphonyl) benzene

To a solution of 0.05 mol of (4-methoxybenzenesulphonyl)benzene in 150 ml of anhydrous benzene, was added 0.02 mol of aluminium chloride and the reaction medium was maintained for about 15 hours under stirring at room-temperature. After this period of time, the mixture was poured onto crushed ice. The organic phase was collected, dried on sodium sulphate and evaporated to dryness.

In this manner (4-hydroxybenzenesulphonyl) benzene was obtained in a yield of 68%. M.P. : 135° C.

(b) 4{3-[N-Methyl-N-(3,4-dimethoxy-β-phenethyl)amino]-propyloxy}benzenesulphonyl hydrochloride To a solution of 0.0147 mol of (4-hydroxybenzenesulphonyl) benzene in 25 ml of dimethylsulphoxide, was added 0.0294 mol of potassium carbonate and 0.0147 mol of 1-chloro-3-[N-methyl-N-(3,4.dimethoxy-β-phenethyl)amino] propane. The mixture was maintained under stirring for 24 hours at room-temperature and 60 ml of water were added. After extraction with ethyl ether, the organic phase was dried and evaporated to dryness to obtain an oily product. The hydrochloride was formed by adding hydrogen chloride in ethyl ether to an ethereal solution of the base so provided.

In this manner, 4-{3-[N-methyl-N-(3,4-dimethoxy-β-phenethyl)amino]propyloxy}benzenesulphonylbenzene hydrochloride was obtained in a yield of 30%.

M.P. 114° C. (ethanol).

Using the same procedure as that described above, 4-[3-(di-n-butylamino) propyloxy]benzenesulphonyl-benzene oxalate was obtained (SR 31810 A).(Example 64)

Yield : 48%.

M.P. 78–81° C. (isopropanol).

EXAMPLE 65

Preparation of 2-n-butyl-1-{4-[3-(di-n-butylamino)-propyloxy]benzenesulphonyl}benzimidazole acid oxalate (SR 33631A)

(a) 2-n-Butyl-1-(4-bromopropoxy-benzenesulphonyl)benzimidazole

A solution of 0.0035 mol of 4-bromopropoxy-benzimidazole, 0.0035 mol of 2.n-butyl-benzimidazole and 0.0035 mol of triethylamine in 15 ml of dioxan was maintained for 7-8 hours under stirring and at roomtemperature. The solvent was eliminated under vacuum to obtain a residue which was purified by chromatography on a silica column (eluent: dichloromethane/ethyl acetate 9/1).

In this manner 2-n-butyl-1-(4-bromopropoxy-benzenesulphonyl) benzimidazole was obtained and was used as such.

Yield : 50%.

(b) 2-n-Butyl-1-{4-[3-(di-n-butylamino) propyloxy]benzenesulphonyl}benzimidazole acid oxalate To a solution of 0.0017 mol of 2-n-butyl-1-(4-bromopropoxy-benzenesulphonyl) benzimidazole in 15 ml of dimethylsulphoxide was added 0.0034 mol of n-butylamine. The reaction medium was allowed to stand for 17 hours at room-temperature and then poured into 50 ml of water. After extraction, the ethereal phase was dried and evaporated to dryness. The residue so obtained was purified by chromatography on a silica column (eluent : dichloromethane/ethyl acetate) to obtain an oil which was the desired product in the form of the free base (yield : 50%). The oxalate of the base so provided was formed by dissolving the base in question into ethyl ether and adding an ethereal solution of oxalic acid.

In this manner 2-n-butyl-1-{4-[3-(di-n-butylamino) propyloxy]benzenesulphonyl}benzimidazole acid oxalate was obtained after recrystallization from ethanol.

EXAMPLE 66

Preparation of 2-isopropyl-3-[4-{3-[N-methyl-N-(3,4-dimethoxy-β-phenethyl amino]propyloxy}benzenesulphonyl benzofuran oxalate (SR 33670 A)

A mixture of 0.0021 mol of 2-isopropyl-3-(4-hydroxybenzenesulphonyl) benzofuran, 0.002 mol of 1-chloro-3-[N-methyl-N-(3,4-dimethoxy-βphenethyl)amino] propane and 0.0002 mol of potassium carbonate in 2 ml of N,N-dimethylformamide was stirred at 100° C. for 1 hour. The medium was then poured into water and distilled in the presence of ethyl acetate. After that the mixture was dried on sodium sulphate, filtered and concentrated. The residue was taken up in ethyl acetate and the solution was purified by chromatography on a silica column using methanol as eluent. The oily product so obtained in free base form was taken up in ethyl acetate and one equivalent of oxalic acid in ethyl ether was added. The precipitate so formed was filtered out and recrystallized.

In this manner 2-isopropyl-3-[4-{3-[N-methyl-N-(3,4-dimethoxy-β-phenethyl)amino] propyloxy) benzenesulphonyl]benzofuran oxalate was obtained in a yield of 90%.

M.P. : 151–158° C. (methanol/ethyl acetate).

Using the same method as that described above, the following compounds were prepared:

Compounds :

2-n-Propyl-3-[4-{3-[N-methyl-N-(3,4-dimethoxy-β-phenethyl)amino]propyloxy)oxy}-benzenesulphonyl]benzofuran oxalate (SR 33689 A) (Example 67).

M.P. : 143–144° C. (methanol/ethyl acetate)

2-n-Propyl-3-[4-{3-[N-methyl-N-(3,4-dimethoxy-β-phenethyl)amino]propyloxy}-benzenesulphonyl]benzothiophene hemioxalate (SR 33688A)(Example 68).

M.P 148–149° C. (methanol/ethyl acetate).

EXAMPLE 69

Preparation of
2-n-butyl-3-[4-{3-[N-methyl-N-(3,4-dimethoxy-β-phenethyl)
amino]propyloxy}benzenesulphonyl]benzofuran hydrochloride (SR 33646A)

(a)

2-n-Butyl-3-[4-(3-bromopropyloxy)benzenesulphonyl]-benzofuran

To a solution of 0.02 mol of 2-n-butyl-3-(4-hydroxybenzenesul-phonyl)-benzofuran in 150 ml of dimethylsulphoxide, was added 0.06 mol of finely crushed anhydrous potassium carbonate. The mixture was stirred for 1 hour. After that 0.1 mol of 1,3-dibromo-propane was added and the reaction medium was heated to 50° C. for 6 hours. After the reaction was terminated, the mixture was filtered and evaporated to dryness under vacuum. The residue so obtained was then taken up in dichloroethane, washed with water, then with a dilute solution of sodium hydroxide and finally with water. The organic phase was evaporated to dryness under vacuum to obtain a residual oil which was purified by chromatography on a silica column (eluent : hexane/ethyl acetate 9/1).

In this manner, 2-n-butyl-3-[4-(3-bromopropyloxy) benzenesulphonyl]benzofuran was obtained in a yield of 43%.

(b)

2-n-Butyl-3-[4-{3-[N-methyl-N-(3,4-dimethoxy-β-phenethyl)amino]propyl-oxy)}benzenesulphonyl]benzofuran hydrochloride A mixture of 0.0086 mol of 2-n-butyl-3-[4-(3-bromopropyloxy) benzenesulphonyl]benzofuran, 4 g of anhydrous potassium carbonate and 0.015 mol of N-methyl-3,4-dimethoxy-β-phenethylamine in 50 ml of dimethylsulphoxide was maintained under stirring for 24 hours. The reaction medium was poured into water and extracted with ethyl ether. The organic solution was washed with water, dried on sodium sulphate, filtered and evaporated to dryness under vacuum. The oily residue was purified by chromatography on a silica column using, as eluent, a dichlorethane/ methanol 9/1 mixture. The hydrochloride of the base so provided was formed by adding an ethereal solution of hydrogen chloride.

In this manner, 2-n-butyl-3-[4-{3-[N-methyl-N-(3,4-dimethoxy-β- phenethyl)amino]propyloxy}benzenesulphonyl]benzofuran hydrochloride was obtained in a yield of 38%.

M.P. : 60° C. (diisopropyl ether).

EXAMPLE 70

Preparation of
2-isopropyl-3-{4-[3-(di-n-butylamino)propyloxy]benzenesulphonyl}pyrazolo[-1,5-a]pyridine oxalate (SR 36684A)

(a)

2-Isopropyl-3-(4-methoxybenzenesulphonyl)-pyrazolo[1,5-a]pyridine

A solution of 0.03 mol of 2-isopropyl-pyrazolo[1,5-a]pyridine and 0.03 mol of 4-methoxybenzenesulphonyl chloride in 60 ml of dichloroethane was cooled to -24° C. After that 0.068 mol of aluminium chloride was added in one fraction and the reaction medium was allowed to return to roomtemperature for 3 hours. The mixture was then poured into ice water and distilled in the presence of ethyl acetate. After drying on sodium sulphate, the medium was filtered and concentrated. The solid so obtained was then recrystallized from an ethyl acetate/hexane mixture to provide a product in the form of a white crystalline solid.

In this manner, 0.0!8 mol of 2-isopropyl-3-(4-methoxybenzenesulphonyl) pyrazolo[1,5-a]pyridine was obtained. Yield : 60%. M.P. : 38–139° C.

(b)

2-Isopropyl-3-(4-hydroxybenzenesulphonyl)-pyrazolo[1,5-a]pyridine

A mixture of 0.012 mol of 2-isopropyl-3-(4-methoxybenzenesulphonyl) pyrazolo[1,5-a]pyridine and 0.054 mol of pyridine hydrochloride was heated at 220° C. for & hour. Water was then added and the mixture was distilled in the presence of ethyl acetate. The medium was dried on sodium sulphate, filtered and concentrated. The solid so obtained was then recrystallized from isopropyl ether to provide a white crystalline product.

In this manner, 0.012 mol of 2-isopropyl-3-(4-hydroxybenzesulphonyl) pyrazolo[1,5-a]pyridine was obtained.

Yield : 99%.

M.P. : 146.2° C.

(c)

2-Isopropyl-3-{4-[3-(di-n-butylamino)propyloxy]benzenesulohonyl}pyrazolo]-1,5-a]pyridine oxalate A mixture of 0.003 mol of 2-isopropyl-3-(4-hydroxybenzenesulphonyl) pyrazolo[1,5-a]pyridine, 0.003 mol of 1-chloro-3-(di-n-butylamino)propane and 0.004 mol of potassium carbonate in 6 ml of N,N-dimethylformamide was stirred for 40 min. at 100° C. The reaction medium was then poured into water and distilled in the presence of ethyl acetate. After drying on sodium sulphate, the mixture was filtered and concentrated. The residue was then purified on a silica column using an ethyl acetate/hexane 3/7 mixture as eluent. The base so obtained, in oily form, was then treated with an ethereal solution of one equivalent of oxalic acid and the precipitate which formed was filtered out and recrystallized from an ethyl ether/isopropanol mixture.

In this manner, 0.0028 mol of 2-isopropyl-3-{4-[3-(di-n-butylamino) propyloxy]benzenesulphonyl} pyrazolo[1,5-a]pyridine oxalate was obtained.

Yield : 92%.

M.P. : 72° C.

Using the same procedure as that described above, 2-isopropyl-3-[4-}3-[N-methyl-N-(3,4-dimethoxy--β-phenethyl)amino]propyloxy}benzenesulphonyl]-pyrazolo(1,5-a]pyridine oxalate was obtained (SR 33679A)(Example 71).

M.P. : 144–147° C. (isopropanol).

EXAMPLE 72

Preparation of 2-isopropyl-3-{4-[3-(tertiobutylamino)propyloxy]benzene sulphonyl}pyrazolo[1,5 -a]pyridine oxalate (SR 33686A)

(a)

2-Isopropyl-3-[4-(3-bromopropyloxy)benzenesulphonyl]pyrazolo[1,5-a]pyridine

A mixture of 0.003 mol of 2-isopropyl-3-(4-hydroxybenzenesulphonyl) pyrazolo[1,5-a]pyridine, 0.064 mol of 1,3-dibromopropane and 0.004 mol of potassium carbonate in 6 ml of N,N-dimethylformamide was stirred at 100° C. for one hour. The medium was then poured into water and distilled in the presence of ethyl acetate. After drying on sodium sulphate, the mixture was filtered and concentrated to obtain a residue which was purified on a silica column using an ethyl acetate/hexane 1/1 mixture.

In this manner, 0.0021 mol of 2-isopropyl-3-[4-(3-bromopropyloxy) benzenesulphonyl]pyrazolo[1,5-a]pyridine was obtained in the form of a viscous oil. Yield : 69%.

(b)

2-Isopropyl-3-{4-[3-(tertiobutylamino)propyloxy]benzenesulphonyl}pyrazolo[1,5-a9 pyridine oxalate In a flask, a solution of 0.002 mol of 2-isopropyl-3-[4-(bromopropyloxy)benzenesulphonyl]pyrazolo[1,5-a]pyridine and 0.008 mol of tertiobutylamine in 4 ml of N,N-dimethylsulphoxide was stirred at room-temperature for 24 hours. The mixture was poured into water and then distilled in the presence of ethyl acetate. After drying on sodium sulphate, the medium was filtered and concentrated to obtain a base in oily form. A solution of this base in an ethyl ether/ethyl acetate mixture was then treated with one equivalent of oxalic acid and the white precipitate so obtained was recrystallized from an ethyl ether/isopropanol mixture.

In this manner, 0.002 mol of 2-isopropyl-3-{4-[3-(tertiobutylamino) propyloxy]benzenesulphonyl} pyrazolo[1,5-a]pyridine oxalate was obtained. Yield : 99%. M.P. : 208° C.

EXAMPLE 73

Preparation of 2-isopropyl-3-[4-{3-[N-methyl-N-(3,4-dimethoxy-β-phenethyl) amino]propyloxy}benzenesulphonyl]-4,5-dihydro-furan oxalate (SR 33681A)

(a)

1-(4-Tosyloxybenzenesulphonyl)-3-methyl-butan-2-one

A mixture of 0.1 mol of sodium 4-tosyloxysulphinate and 0.1 mol of bromomethyl isopropyl ketone in 400 ml of N,N-dimethylformamide was stirred at 85° C. for 90 min. The mixture was then poured onto ice and filtered on fritted glass. The pasty residue so obtained was successively washed twice with water, once with 200 ml of ethanol and finally with ethyl ether. After drying under vacuum for 2 hours the desired product was provided after recrystallization from ethyl acetate.

In this manner, 0.074 mol of 1-(4-tosyloxybenzenesulphonyl)-3-methyl-butan-2-one was obtained in the form of a white solid.

Yield : 74%.

M.P. : 160° C.

(b)

1-Isobutyryl-1-(4-tosyloxybenzenesulphonyl)cyclopropane

A mixture of 0.05 mol of 1-(4-tosyloxybenzenesulphonyl)-3-methylbutan-2-one, (0.05 mol) of 1,2-dibromo-ethane and 0.12 mol of potassium carbonate in 100 ml of N,N-dimethylformamide was stirred at room-temperature for 60 hours. The reaction mixture was poured into water, acidified with dilute hydrochloric acid and extracted with ethyl acetate. After drying on sodium sulphate, the medium was filtered and concentrated. The residue so obtained was then purified by chromatography on a silica column using an ethyl acetate/hexane 3/7 mixture as eluent.

In this manner, 0.026 mol of 1-isobutyryl-1-(4-tosyloxybenzenesulphonyl)cyclopropane was obtained in a yield of 53%.

M.P. : 106–107° C.

(c)

1-Isobutyryl-1-(4-hydroxybenzenesulphonyl)cyclopropane

Into 85 ml of ethanol heated to 80° C., was dissolved 0.026 mol of 1-isobutyryl-1-(4--tosyloxybenzenesulphonyl)cyclopropane. A solution of 0.05 mol of sodium hydroxide in 30 ml of water was then added and the medium was maintained at 80° C. for 10 min. The ethanol was eliminated under reduced pressure and the residue was taken up in dilute hydrochloric acid and distilled in the presence of ethyl acetate. After drying on sodium sulphate, the medium was filtered and concentrated. The residue so obtained was then purified by chromatography on a silica column using an ethyl acetate/hexane 1/1 mixture.

In this manner, 0.016 mol of 1-isobutyryl-1-(4-hydroxybenzenesulphonryl) cyclopropane was obtained in the form of a white solid.

Yield : 60%.

: M.P. 111–112° C. (ethyl acetate).

(d) 1-Isobutyryl-1-[4-{3-[N methyl-N-(3,4-dimethoxy-β-phenethyl)amino]-propyloxy}-benzenesulphonyl]cyclopropane A mixture of 0.005 mol of 1-isobutyryl-1-(4-hydroxybenzenesulphonyl) cyclopropane, 0.0048 mol of 1-chloro-3-[N methyl-N-(3,4-dimethoxy-β-phenethyl-)amino]propane and 0.005 mol of potassium carbonate in 5 ml of N,N-dimethylformamide was heated at 140° C. for 15 min. The reaction mixture was then poured into water and distilled in the presence of ethyl acetate. After drying on sodium sulphate, the medium was filtered and concentrated. The residue was then purified by chromatography on a silica column using an ethyl acetate/hexane 1/1 mixture.

In this manner, 0.0033 mol of 1-isobutyryl-1-[4{3-[N-methyl-N-(3,4-dimethoxy-β-phenethyl)-amino]-propyloxy}benzenesulphonyl]cyclopropane was obtained in oily form.

Yield : 66%.

(e)
2-Isopropyl-3-[4-{3-[N-methyl-N-(3,4-dimethoxy-β-phenethyl)amino]propyloxy}-benzenesulphonyl]-4,5-dihydro-furan oxalate A mixture of 0.002 mol of 1-isobutyryl-1-[4-{3-[N-methyl-N-(3,4-dimethoxy-β-phenethyl)-amino]-propyloxy}benzenesulphonyl]cyclopropane and 0.003 mol of tricaprylylmethyl ammonium chloride was heated at 115° C. for 30 min. The reaction medium was then purified by chromatography on a silica column using an ethyl acetate/hexane 1/1 mixture to obtain a base in oily form. An ethereal solution of the base so provided was then treated with one equivalent of oxalic acid in ethyl ether.

In this manner, 0.0013 mol of 2-isopropyl-3-[4-{3-[N-methyl-N-(3,4-dimethoxy-β-phenethyl)-amino]-propyloxy}benzenesulphonyl]-4,5-dihydro-furan oxalate was obtained in the form of a white solid.
Yield : 65%.
M.P. : 147.2° C. (methanol).

EXAMPLE 74

Preparation of 2-isopropyl-3-{4-[3-(di-n-butylamino)propyloxy]benzenesulphonyl}-quinoline oxalate (SR 33695 A)

(a)
2-Isopropyl-3-(4-tosyloxybenzenesulphonyl)quinoline

In a sealed the a mixture of 0.02 mol of 2-aminobenzaldehyde and 0.02 mol of 1-(4-tosyloxybenzenesulphonyl)-3-methyl-butan-2-one was heated at 185° C. for 2 hours. The mixture was then taken up in dry ethyl ether and filtered.
M.P. of the hydrochloride : about 90° C.

(b)
2-Isopropyl-3-(4-hydroxybenzenesulphonyl)quinoline

To a solution of 0.017 mol of 2-isopropyl-3-(4-tosyloxybenzenesulphonyl) quinoline in 250 ml of ethanol, was added a solution of 0.068 mol of sodium hydroxide in 5 ml of water. The mixture was heated to reflux for 2 hours and then the solvent was eliminated. The residue so obtained was taken up in water and neutralized with acetic acid. The precipitate which formed was then filtered out, dried and recrystallized from a dichlorethane/heptane 1/1 mixture.

In this manner, 2-isopropyl-3-(4-hydroxybenzenesulphonyl) quinoline was obtained in a yield of 58%.
M.P. : 185° C.

(c)
2-Isopropyl-3-{4-[3-(di-n-butylamiho)propyloxy]benzenesulphonyl}quinoline oxalate To a solution of 0.005 mol of 2-isopropyl-3-(4-hydroxybenzenesulphonyl)quinoline in 25 ml of dimethylsulphoxide, was added 0.015 mol of anhydrous potassium carbonate. The mixture was stirred for 30 min. and 0.0075 mol of 1-chloro-3-(di-n-butylamino)-propane was added. The reaction medium was maintained under stirring for 24 hours. After this period of time, the mixture was poured into water and extracted with ethyl ether. The organic phase was washed with water, dried on sodium sulphate, filtered and evaporated to dryness. An oily base was so provided which was purified by chromatography on a silica column (eluent : isopropanol) and transformed into an oxalate by adding oxalic acid in ethyl ether.

In this manner 2-isopropyl-3-{4-[3-(di-n-butylamino)propyloxy}benzenesulphonyl]quinoline oxalate was obtained in a yield of 55%.
M.P. : 130° C. (ethanol).

Using the same method as that described above, 2-isopropyl-3-[4-{3-[N-methyl-N-(3,4-dimethoxy--β-phenethyl)amino]propyloxy}benzenesulphonyl]-quinoline oxalate (SR 33694 A) (Example 75).
M.P. : 162° C. (ethanol).

EXAMPLE 76

Preparation of 5-[4-{3-[N-methyl-N-(3,4-dimethoxy-β-phenethyl)amino]propyloxy}benzenesulphonyl]--6-isopropyl-pyrrolo[1,2-b]pyridazine oxalate (SR 33687A)

(a)3-(4-Tosyloxybenzenesulphonyl)methyl-pyridazine

To a solution of 0.13 mol of 3-chloromethyl-pyridazine hydrochloride in 400 ml of dimethylsulphoxide was added 0.13 mol of sodium bicarbonate. The mixture was stirred for 30 min. and 0.195 mol of sodium 4-tosyloxybenzenesulphonate was introduced. The reaction medium was maintained under stirring for 2 hours at room-temperature then for 2 hours at 50° C. The mixture was poured into 3lof water and the precipitate so formed was filtered, washed with water and dried under vacuum.

In this manner, 3-(4-tosyloxybenzenesulphonyl)methyl-pyridazine was obtained in a yield of 82%.
M.P. : 161° C. (ethanol).

(b)
5-(4-Tosyloxybenzenesulphonyl)-6-isopropyl-pyrrolo[1,2-b]pyridazine.

A mixture of 0.011 mol of 3-(4-tosyloxybenzenesulphonyl)methylyl-pyridazine and 0.011 mol of 1,8-diazabicyclo[5,4,0]undec-7-ene in 40 ml of hexamethylphosphoramide was heated at 75° C. for 30 min. After that 4 g of bromomethyl isopropyl ketone were added while maintaining the same temperature for 6 hours. The mixture was poured into 200ml of water and extracted with dichloroethane. The organic solution was washed with water, dried on sodium sulphate and filtered. The solvent was eliminated under vacuum to provide an oily residue which was purified by chromatography on a silica 9olumn (eluent : dichloroethane).

In this manner, 5-(4-tosyloxybenzenesulphonyl)-6-isopropyl-pyrrolo [1,2-b]pyridazine was obtained in crystalline form.
Yield : 7%
M.P. : 149° C. (isopropanol).

(c)
5-(4-Hydroxybenzenesulphonyl)-6-isopropyl-pyrrolo[1,2-b]pyridazine.

A solution of 0.0034 mol of 5-(4-tosyloxybenzenesulphonyl)-6-isopropylpyrrolo[1,2-b]pyridazine in 75ml of ethanol was heated to boiling and a solution of 0.0034 mol of sodium hydroxide in 3ml of water was added. Boiling was maintained for 6 hours. The solvent was eliminated and the residue was taken up in water and neutralized with acetic acid. The precipitate so formed was taken up in dichloroethane and the solution was washed with water, dried on sodium sulphate and filtered. The solvent was finally evaporated off.

In this manner, 5-(4-hydroxybenzenesulphonyl)-6-isopropyl-pyrrolo [1,2-b]pyridazine was isolated in a yield of 75%.

(c) 5-[4-{3-[N-Methyl-N-(3,4-dimethoxy-β-phenethyl)amino]propyloxy}benzenesulphonyl]--6-isopropyl-pyrrolo[1,2-b]pyridazine oxalate A mixture of 0.0022 mol of 5-(4-hydroxybenzenesulphonyl)-6-isopropylpyrrolo-[1,2-b]pyridazine and 1.5 g of anhydrous potassium carbonate in 25 ml of dimethylsulphoxide was stirred for 30 min. After that, 0.0027 mol of 1-chloro-3-[N-methyl-N-(3,4-dimethoxy-β-phenethyl)amino]propane oxalate was added and stirring was maintained at room-temperature for 18 hours. The reaction medium was then heated at 50° C. for 5 hours, poured into water and extracted with ethyl ether. The ethereal phase was washed with water, dried on sodium sulphate and filtered. After evaporating the solvent, an oily residue was obtained which was purified by chromatography and a silica column using methanol as eluent. The oxalate was formed by adding oxalic acid in ethyl ether to an ethereal solution of the base so provided.

In this manner, 5-[4-{3-[N methyl-N-(3,4-dimethoxy-β-phenethyl)amino]propyloxy)}benzenesulphonyl]-6-isopropyl-pyrrolo[1,2-b]pyridazine oxalate was obtained in a yield of 57%.

M.P. : 88° C. (ethyl acetate/isopropanol).

EXAMPLE 77

Preparation of 2-isopropyl-3-[4-{3[-N-methyl-N-(3,4-dimethoxy-β-phenethyl) amino]propyloxy}benzenesulphonyl]furan oxalate (SR 33697A)

(a) 2-Isopropyl-3-(4-tosyloxybenzenesulphonyl)-4,5-dihydro-furan

A mixture of 0.008 mol of 1-isobutyryl-1-(4-tosyloxybenzenesulphonyl) cyclopropane and 0.022 mol of tricaprylylmethyl ammonium chloride was heated at 130° C. for 30 min. The reaction mixture was then chromatographed on a silica column using an ethyl acetate/hexane 25/75 mixture as eluent.

In this manner, 0.0145 mol of 2-isopropyl-3-(4-tosyloxybenzenesul- phonyl)-4,5-dihydro-furan was obtained in the form of a white solid.

Yield : 66 %.

M.P. : 103° C. (ethyl acetate/hexane).

(b) 2-Isopropyl-3-(4-tosyloxybenzenesulphonyl) furan

A mixture of 0.035 mol of 2-isopropyl-3-(4-tosyloxybenzenesulphonyl)-4,5-dihydro-furan, 1 mol of manganese dioxide and 3 Å-molecular screen in powder (previously dried at 140° C. under 0.01 mm Hg for 5 h) in 400 ml of dry ethyl ether was stirred for 66 hours at room-temperature. The mixture was then filtered and the solid was rinsed with dichloromethane. After concentration the medium was chromatographed on a silica column using an ethyl acetate/hexane 2/8 mixture.

In this manner, 0.009 mol of 2-isopropyl-3-(4-tosyloxybenzenesulphonyl)furan was obtained in a yield of 25%.

M.P. : 94° C. (ethyl acetate/hexane).

(c) 2-Isopropyl-3-(4-hydroxybenzenesulphonyl)furan

To a solution of 0.008 mol of 2-isopropyl-3-(4-tosyloxybenzenesulphonyl)furan in 1.8 ml of ethanol were added 18 ml of 1N-sodium hydroxide. The milky solution was stirred under reflux to complete dissolution (2 minutes) and the reaction medium was cooled and neutralized with dilute hydrochloric acid. After that, the mixture was distilled in the presence of ethyl acetate. The organic phase was dried on sodium sulphate, filtered and concentrated. The residue so obtained was then purified on a silica column and eluted using an ethyl acetate/hexane 4/6 mixture.

In this manner, 0.0073 mol of 2-isopropyl-3-(4-hydroxybenzenesulphonyl) furan was obtained in a yield of 91%.

M.P. : 131° C. (ethyl acetate/hexane).

(d) 2-Isopropyl-3-[4{3-[N-methyl-N-(3,4-dimethoxy-β-phenethyl)amino]--propyloxy}benzenesulphonyl-]furan oxalate A mixture of 0.003 mol of 2-isopropyl-3-(4-hydroxybenzenesulphonyl) furan, 0.003 mol of 1-chloro-3-[N-methyl-N-(3,4-dimethoxy-8-phenethyl)amino]propane and $3.23 \times 10^{-3}$ mols of crushed potassium carbonate in 3 ml of N,N-dimethylformamide was heated at 100° C. for 30 minutes. The mixture was then poured into water and distilled in the presence of ethyl acetate. After drying on sodium sulphate, the medium was filtered and concentrated. The residue so obtained was then purified by chromatography on a silica column using methanol as eluent. After that, the base so provided was transformed into oxalate by adding oxalic acid in ethyl ether.

In this manner, 0.00288 mol of 2-isopropyl-3- [4-{3-[N-methyl-N-(3,4-dimethoxy-⊖-phenethyl) amino]-propyloxy}benzenesulphonyl]furan oxalate was obtained.

Yield : 96%.

M.P. : 102° C. (chloroform/ethyl acetate).

Using the same method as described above, 2-isopropyl-3-{4-[3-(di-n-butylamino)propyloxy]benzenesulphonyl-}furan oxalate (SR 33701 A) (Example 78) was obtained in a yield of 92%.

M.P. : 98° C. (ethanol/ethyl ether).

EXAMPLE 79

Preparation of 2-isopropyl-3-{4-[3-(tert-butylamino)propyloxy]benzenesulphonyl}-furan oxalate (SR 33701 A)

(a) 2-Isopropyl-3-[4-(3-bromopropyloxy)benzenesulphonyl]furan

A mixture of 0.003 mol of 2-isopropyl-3-(4-hydroxylbenzenesulphonyl) furan, 0.06 mol of 1,3-dibromopropane and 0.005 mol of crushed potassium carbonate in 8 ml of N,N-dimethylformamide was heated at 100° C. for 1 hour. The mixture was poured into water and distilled in the presence of ethyl acetate. After drying on sodium sulphate, the medium was filtered and concentrated. The residue so obtained was then purified by chromatography on a silica column using an ethyl acetate/hexane 2/8 mixture.

In this manner, 0.00282 mol of 2-isopropyl-3-[4-(3-bromopropyloxy) benzenesulphonyl]furan was obtained in oily form.

Yield : 94%.

(b) 2-Isopropyl-3-{4-[3-(tert-butylamino)propyloxy]benzenesulphonyl}furan oxalate A mixture of 0.00282 mol of 2-isopropyl-3-[4-(3-bromopropyloxy)benzenesulphonyl]furan and 0.013 mol of tert-butylamine in 7 ml of dimethylsulphoxide was stirred at room-temperature for 24 hours. After that, the mixture was poured into water, distilled in the presence of ethyl acetate, dried on sodium sulphate, filtered and concentrated. The residue so obtained was purified on a silica column using a methanol/ethyl acetate 2/8 mixture as eluent. The oily base so provided was then treated with an ethereal solution of oxalic acid and the precipitate was recrystallized from ethanol.

In this manner, 0.0023 mol of 2-isopropyl-3{4-[3-(tert-butylamino) propyloxy]benzenesulphonyl)}furan oxalate was obtained in a yield of 82%.

M.P. : 143.6° C.

Preparation of 4-[4-{3-[N-methyl-N-(3,4-dimethoxy-β-phenethyl)amino]propyloxy}phenylthio]cinnoline oxalate (SR 33699A)

(a) 4-(4-Methoxyphenylthio)cinnoline

To a solution of sodium methylate prepared from 0.7 g (0.03 at.g.) of sodium in 25 ml of methanol, there were added 4.2 g (0.03 mol) of 4-methoxyphenylthiol. The methanol in excess was eliminated using a rotatory evaporator and the sodium salt so obtained was dried under high vacuum and then dissolved into 100 ml of N,N-dimethylformamide. After that, 4.38 g (0.03 mol) of 4-chlorocinnoline were added. The medium was stirred at room-temperature for 24 hours and then poured into water. After filtration, the product was washed on the filter with water and then dried under vacuum at the temperature of 60° C.

In this manner 6.4g of 4-(4-methoxyphenylthio)cinnoline were obtained in a yield of 80%.

M.P. : 163° C. (7/3 isopropanol/heptane)

Using the same procedure as that described above but from 3-bromocinnoline there was obtained 3-(4-methoxyphenylthio)cinnoline Yield : 74.6%

M.P. : 108° C. (isopropanol)

(b) 4-(4-Hydroxyphenylthio)cinnoline

To a solution of 3.6g (0.0134 mol) of 4-(4-methoxyphenylthio)cinnoline, there were added 30 ml of 47%-hydrobromic acid. The mixture was stirred and heated at 125° C. for 4 hours. The hydrobromic acid in excess was then eliminated with a rotatory evaporator and the residue obtained was taken up with water. The solution was neutralized with sodium bicarbonate and filtered. The product so isolated was washed on the filter with water and dried under vacuum at the temperature of 60° C.

In this manner, 2.9g of 4-(4-hydroxyphenylthio)cinnoline were obtained after recrystallization from a 7/3 isopropanol/heptane mixture.

Yield : 85%

M.P. : 238° C.

Using the same procedure described above but from 3-(4-methoxyphenylthio)cinnoline, there was obtained 3-(4-hydroxyphenylthio)cinnoline in a yield of 90%.

(c) 4-[4-{3-[N-methyl-N-(3,4-dimethoxy-β-phenethyl)amino]propyloxy}phenylthio]cinnoline oxalate A mixture of 2.5g (0.01 mol) of 4-(4-hydroxyphenylthio)cinnoline and 7 g of crushed anhydrous potassium carbonate in 50 ml of dimethylsulphoxide was stirred for 30 min. After that 4.4 g (0.012 mol) of 1-chloro-3-[N-methyl-N-(3,4-dimethoxy-β- phenethyl)amino]propane oxalate were added while stirring was maintained for 24 hours at room-temperature. The medium was poured into water and extracted with ethyl ether. The ethereal solution was washed with water, dried on anhydrous-sodium sulphate and filtered. The ethyl ether was eliminated with a rotatory evaporator to obtain 5.3 g of an oil which was purified by chromatography on a silica column using methanol as eluent. The base so provided (4.7 g) was then transformed into an oxalate in ethyl ether medium and the salt was recrystallized from ethanol.

In this manner 4.1 g of 4-[4-{3-[N-methyl-N-(3,4-dimethoxy-β-phenethyl) amino]propyloxy}phenylthio]cinnoline oxalate were obtained.

Yield : 70.8%

M.P. : 138 and 160° C.

Using the same procedure as that described above but from 3-(4hydroxyphenylthio)cinnoline there was prepared 3-[4-}3-[N-methyl-N-(3,4-dimethoxy-β-phenethyl)amino]propyloxy}phenylthio-]cinnoline oxalate (Example 82) (SR 33704 A)

Yield : 67.6%

M.P. : 166° C.

EXAMPLE 81

Preparation of 3-[4-{3-[N-methyl-N-(3,4-dimethoxy-β-phenethyl)amino]propyloxy}benzenesulphonyl]cinnoline oxalate (SR 33703A)

(a) 3-(4-Hydroxybenzenesulphonyl)cinnoline

A mixture of 2.1 g (0.01 mol) of 3-bromocinnoline, 6.6 g (0.02 mol) of sodium 4-tosyloxybenzenesulphinate and 50ml of dimethylsulphoxide was stirred and heated at !20° C. for 24 hours. The mixture was poured into water and extracted with dichloroethane. The dichloroethane solution was washed with water, dried on anhydrous sodium sulphate and filtered. The solvent was then evaporated with a rotatory evaporator to provide 2.5 g of an oily residue. The desired product was then isolated by chromatography on a silica column using dichlorethane/methanol 98/2.

In this manner, 0.45 g of 3-(4-hydroxybenzenesulphonyl)cinnoline was obtained.

Yield 10.2%

(b) 3-[4-{3-[N-Methyl-N-(3,4-dimethoxy-β-phenethyl)amino]propyloxy}benzene-sulphonyl]cinnoline oxalate.

A mixture of 0.2 g (0.0007 mol) of 3-(4-hydroxvbenzenesulphonyl)cinnoline and 0.4 g of potassium carbonate in 100 ml of dimethylsulphoxide was stirred for 30 min. After that, 0.3 g (0.0008 mol) of 1-chloro-3-[N-mcthyl-N-(3,4-dimethoxy-β-phenethyl)amino-]propane oxalate was added and the stirring was maintained for 24 hours at room-temperature. The medium was poured into water and extracted with ethyl ether. The ethereal solution was washed with water, dried on anhydrous sodium sulphate and filtered. The ethyl ether was then eliminated using a rotatory evaporator and the residue was purified by chromatography on a silica column using methanol as solvent to provide 0.100 g (30%) of a base. This base was then transformed into an oxalate in ethyl ether by adding an ethereal solution of oxalic acid and the salt so formed was recrystallized from ethanol.

In this manner, 0.100g of 3-[4-{3-[N-methyl-N-(3,4-dimethoxy-β-phenethyl)-amino]propyloxy:benzenesulphonyl] cinnoline oxalate was obtained.

M.P. : 158° C.

EXAMPLE 83

Preparation of 2-isopropyl-1-[4{3-[N-methyl-N-oxide-N-(3,4-dimethoxy-β--phenethyl)amino]propyloxy}benzenesulphonyl] indolizine acid oxalate.

A solution of 2.75 g (0.005 mol) of 2-isopropyl-1-[4-{3-[N-methyl-N(3,4-dimethoxy-β-phenethyl)amino]-propyloxy}benzenesulphonyl]indolizine in 40 ml of dichloromethane was cooled to −10° C. Under stirring, 1 g(0.005 mol) of 3-chloro-perbenzoic acid in 40 ml of dichloromethane was added to the reaction medium which was then allowed to return to room-temperature. The mixture was washed with a sodium carbonate solution and then with water. After drying on sodium sulphate and filtering, the solvent was evaporated off using a rotatory evaporator. The residue so obtained (3.1 g) was then purified by chromatography on a silica column using methanol as solvent to obtain the required N-oxide derivative in free base form. The oxalate was then formed by adding an ethereal solution of oxalic acid to a solution, of the base so provided, in tetrahydrofuran/ethyl ether.

In this manner, 2-isopropyl-1-[4-{3-[N-methyl-N-oxide-N-(3,4-dimethoxy-β-phenethyl)-amino]propyloxy}benzenesulphonyl]indolizine acid oxalate was obtained. The N.M.R. spectrum was found to be correct.

EXAMPLE 84

Preparation of 1-benzyl-2-[4-{3-[N-methyl-N-(3,4-dimethoxy-β-phenethyl)-amino]propyloxy}benzenesulphonyl]imidazole.

(a) N-Benzylimidazole

To a solution of 24 g (1 mol) of sodium hydride in 500 ml of N,N-dimethylformamide, there was added, drop-by-drop, a solution of 68 g (1mol) of imidazole in 150 ml of N,N-dimethylformamide. The medium was stirred for 2 hours and then 126.6 g (1mol) of benzyl chloride were added. The solvent was eliminated and the residue was taken up with ethyl acetate and washed with water. The organic phase was dried and concentrated to provide an oil which crystallized when cold.

In this manner, N-benzylimidazole was obtained in a yield of 70%.

(b) 1-Benzyl-2-(4-methoxybenzenesulphonyl)imidazole

To a solution of 44 g (0.28 mol) of 1-benzylimidazole in 200 ml of acetonitrile, there were added, drop-by-drop, 57.5 g (0.28 mol) of 4-methoxybenzenesulphonyl chloride dissolved into 50 ml of acetonitrile. After one hour, 41.5 ml (0.31 mol) of triethylamine were added and the medium was maintained under stirring for 12 hours. The precipitate was isolated and the solution was purified by high pressure liquid chromatography using dichloromethane as eluent.

In this manner, 1-benzyl-2-(4-methoxybenzenesulphonyl)imidazole was obtained in a yield of 5%.

(c) 1-Benzyl-2-(4-hydroxybenzenesulphonyl)imidazole

A mixture of 2.6 g ($8 \times 10^{-3}$ mol) of 1-benzyl-2-(4-methoxybenzenesulphonyl)imidazole in 10 ml of iodhydric acid was heated for 5 hours at 170° C. The reaction medium was then poured into ice water and extracted with ethyl acetate. The organic phase was dried and concentrated and the residue obtained was purified by high pressure liquid chromatography using dichloromethane as eluent.

In this manner, 1-benzyl-2-(4-hydroxybenzenesulphonyl)imidazole was obtained in a yield of 20%.

1-Benzyl -2-[4-{3-[N-methyl-N-(3,4-dimethoxy-β-phenethyl)amino]propyloxy}benzenesulphonyl- imidazole A mixture of 0.5 g ($1.6 \times 10^{-3}$ mol) of 1-benzyl-2-(4-hydroxybenzenesulphonyl)imidazole, 0.86g ($2.4 \times 10^{-3}$ mol) of 1-chloro-3-[N-methyl-N-(3,4-dimethoxy- β-phenethyl)amino]propane oxalate and 1.1 g ($7.9 \times 10^{-3}$ mol) of potassium carbonate in of dimethylsulphoxide was maintained at 35° C. for 3 days. The reaction medium was then poured into ice water and the oil so obtained was purified by high pressure liquid chromatography using ethyl acetate as eluent.

Yield : 78%.

EXAMPLE 85

Preparation of 1-isopropyl-2-[4-{3-[N-methyl-N-(3,4-dimethoxy-B-phenethyl)amino]propyloxy}benzenesulphonyl]benzimidazole oxalate.

(a) 1-Isopropyl-2(4-benzyloxybenzenesulphonyl)benzimidazole

To a solution of $7.08 \times 10^{-4}$ mol of 4-benzyloxybenzenesulphonyl chloride in 10 ml of acetonitrile cooled to 0° C, there was added $7.08 \times 10^{-4}$ mol of 1-isopropyl-benzimidazole prepared in N,N-dimethylformamide from benzimidazole and isopropyl bromide in the presence of sodium hydride. After that one equivalent of triethylamine was added. The medium was stirred at room-temperature for 12 hours and the acetonitrile was then evaporated off. The residue so obtained was then taken up wi.ht water and extracted several times with dichloromethane. The organic extracts were collected, dried and evaporated. The residue so provided was purified by chromatography on a silica column using a dichloromethane/ethyl acetate 99/1 mixture as eluent.

In this manner, 1-isopropyl-2-(4-benzyloxybenzenesulphonyl)benzimidazole was obtained in a yield of 52%.

M.P. : 94–96° C.

(b) 1-Isopropyl-2-(4-hydroxybenzenesulphonyl)benzimidazole.

To 20 ml of ethanol, there were added $2.95 \times 10^{-4}$ mol of 1-isopropyl-2(4-benzyloxybenzenesulphonyl)-benzimidazole and 0.15 g of 10%-palladium charcoal and the mixture so obtained was maintained under hydrogen atmosphere. When the required quantity of hydrogen was absorbed namely after about 2 hours, the catalyst was filtered out and washed with ethanol. The alcoolic extracts were collected and evaporated under vacuum.

In this manner 1-isopropyl-2-(4-hydroxybenzenesulphonyl)benzimidazole was obtained in the form of a white crystalline product.

Yield : 64%
M.P. : 198° C.

(c) 1-Isopropyl-2-[4-{3-[N-methyl-N-3,4-dimethoxy-$\beta$-phenethyl)amino]propyloxy}-benzenesulphonyl]benzimidazole oxalate To a mixture of $1.42 \times 10^{-4}$ mol of 1-isopropyl-2-(4-hydroxybenzenesulphonyl)benzimidazole and 5 equivalents of potassium carbonate in 5 ml of dimethylsulphoxide, there was added 1.5 equivalent of 1-chloro-3-[N-methyl-N-(3,4-dimethoxy-$\beta$-phenethyl)-amino]propane oxalate. The medium was stirred for about 15 hours at 35° C. and the residue was poured on ice and extracted with ethyl acetate. The organic phase was then dried and evaporated and the base so provided was purified by chromatography on a silica column using an ethyl acetate/ methanol 95/5 mixture. The oxalate was then formed using an ethereal solution of oxalic acid.

In this manner, 1-isopropyl-2-[4-{3-[N-methyl-N-(3,4-dimethoxy-$\beta$-phenethyl)amino]-propyloxy}benzenesulphonyl]benzimidazole oxalate was obtained.

EXAMPLE 86

Preparation of 2-[4-{3-[N-methyl-N-(3,4-dimethoxy-$\beta$-phenethyl)amino]propyloxy}-benzenesulphonyl]pyrimidine oxalate (a 2-(4-Methoxybenzenesulphonyl)pyrimidine To $8.7-10^{-2}$ mol of 50%-sodium hydride in 20 ml of N,N-dimethylformamide, there were added 12.3 g ($8.7 \times 10^{-2}$ mol) of 4-methoxyphenylthiol. After the gaseous evolution was terminated namely after about 2 hours, 10 g ($8.7 \times 10^{-2}$ mol) of 2-chloropyrimidine in 100 ml of N,N-dimethylformamide were added. The medium was stirred at room-temperature for 3 hours and the slight precipitate was filtered out. After evaporation of the solvent, the oily residue was taken up in 100 ml of water and the mixture was stirred. The product which crystallized was then filtered out and washed with water.

In this manner 2-(4-methoxybenzenesulphonyl)-pyrimidine was obtained in a yield of 89%.
M.P. : 72° C.

(b) 2-(4-Hydroxybenzenesulphonyl)pyrimidine

A mixture of $4.6 \times 10^{-3}$ mol of 2-(4-methoxybenzenesulphonyl)pyrimidine and 10 of 47%-hydrobromic acid was heated for ! hour at 90° C. The reaction medium was neutralized to a pH of 7 with an ammonia solution and the pasty residue was extracted with dichloromethane. The organic phase was then dried and evaporated and the residue so provided was purified by chromatography on a silica column using dichloromethane as eluent.

(c) 2-[4-{3-[N-methyl-N-(3 4-dimethoxy-$\beta$-phenethyl)amino]propyloxy}-benzenesulphonyl]-pyrimidine oxalate To a mixture of $1.6 \times 10^{-3}$ mol of 2-(4-hydroxybenzenesulphonyl) pyrimidine, $2.4 \times 10^{-3}$ mol of 1-chloro-3-[N-methyl-N-(3,4-dimethoxy-$\beta$- phenyl)amino]propane oxalate and 1.1 g of potassium carbonate was maintained at 35° C. for several hours and the residue was poured on ice and extracted with ethyl acetate. The organic phase was then dried and evaporated and the base so provided was purified by chromatography on a silica column. The oxalate was then formed using an ethereal solution of oxalic acid.

In this manner 2-[4-{3-[N-methyl-N-(3,4-dimethoxy-$\beta$-phenethyl)amino]propyloxy}-benzenesulphonyl]-pyrimidine oxalate was obtained.

EXAMPLE 87

Preparation of 2-[4-{3-[N-methyl-N-(3,4-dimethoxy-$\beta$-phenethyl)amino]propyloxy}-benzenesulphonyl]indene oxalate (a) 3-Chloro-2-(4-tosyloxybenzenesulphonyl)indane.

Under nitrogen atmosphere, a mixture of 0.05 mol of indene, 0.05 mol of sulphonyl chloride, 0.0005 mol of cupric chloride and 0.0005 mol of triethylamine hydrochloride in 3 ml of acetonitrile was heated at 115 ° C. for 2 hours. The medium was then poured into methanol and the precipitate which formed was filtered and recrystallized from an ethyl acetate/chloroform mixture.

In this manner, 0.042 mol of 3-chloro-2-(4-tosyloxybenzenesulphonyl) indane was obtained in a yield of 84%.

M.P. : 176° C.

(b) 2-(4-Tosyloxybenzenesulphonyl)indene

A mixture of 0.025 mol of 3-chloro-2-(4-tosyloxybenzenesulphonl) indane and 0.04 mol of triethylamine in 125 ml of chloroform was stirred for 4 hours at room-temperature. The medium was poured into water and distilled in the presence of chloroform. The organic phase was dried on sodium sulphate, filtered and concentrated. The green solid so obtained was recrystallized first from tetrahydrofuran and then from ethyl acetate In this manner, 0.024 mol of 2-(4-tosyloxybenzenesulphonyl)indene was obtained in the form of a white solid.

Yield : 82%
M.P. : 174° C.

(c) 2-(4-Hydroxybenzenesulphonyl)indene.

A suspension of 0.01 mol of 2-(4-tosyloxybenzenesulphonyl)indene in 100 ml of 2N-sodium hydroxide and 160ml of ethanol was heated to 80° C. After complete dissolution, the reaction medium was poured into water, acidified with dilute hydrochloric acid and distilled in the presence of dichloromethane. The residue was stirred in the presence of animal charcoal and sodium sulphate and then filtered and concentrated.

In this manner 0.005 mol of 2-(4-hydroxybenzenesulphonyl)indene was obtained in a yield of 52%.

5 M.P. : 209–210° C. (ethyl acetate/hexane).

(d) 2-[4-{3-[N-methyl-N-(3,4-dimethoxy-$\beta$-phenethyl)amino]propyloxy}benzene-sulphonyl]indene oxalate A mixture of 0.005 mol of 2-(4-hydroxybenzenesulphonyl)indene and 3.5 g of crushed potassium carbonate in 10 ml of dimethylsulphoxide was stirred for 30 min. After that, 0.006 mol of 1-chloro-3-[N-methyl-N-(3,4-dimethoxy-$\beta$-phenethyl)amino]propane oxalate was added while stirring was maintained for 24 hours at room-temperature. The medium was poured into water and extracted with ethyl ether. The ethereal solution was washed with water, dried on anhydrous sodium sulphate and filtered. The ethyl ether was eliminated with a rotatory evaporator and the residue so obtained was purified by chromatography on a silica column. The base so provided was then transformed into an oxalate by adding oxalic acid in ethyl ether.

In this manner 2-[4-{3-[N-methyl-N-(3,4-dimethoxy-β-phenethyl)amino]propyloxy}benzenesulphonyl]indene oxalate was obtained.

M.P. : 176° C. (ethanol/isopropanol).

EXAMPLE 88

According to known pharmaceutical techniques, a capsule containing the following ingredients was prepared:

| Ingredient | mg |
| --- | --- |
| Compound of the invention | 100.0 |
| Starches | 99.5 |
| Colloidal silica | 0.5 |
| | 200.0 |

We claim:

1. An aminoalkoxyphenyl compound of formula:

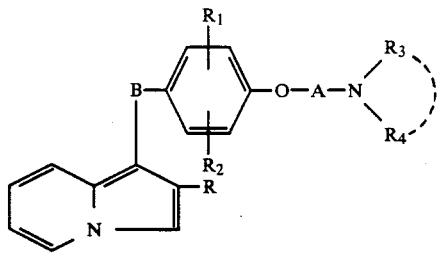

in which:

B represents —S—, —SO— or —$SO_2$— group,

R denotes hydrogen, a linear- or branched-alkyl radical, a cycloalkyl radical containing at most 6 carbon atoms or a phenyl group which is unsubstituted or substituted with one or more substituents, which may be identical or different, selected from halogen atoms and from lower alkyl, lower alkoxy or nitro groups, $R_1$ and $R_2$, which are identical or different, each denote hydrogen, a methyl or ethyl radical or a halogen, A denotes a linear- or branched-alkylene radical having from 2 to 5 carbon atoms or a 2-hydroxypropylene radical in which the hydroxy is optionally substituted by a lower alkyl radical, $R_3$ denotes a linear- or branched-alkyl radical or a radical of formula:

Alk—$R_5$ in which Alk denotes a single bond or a linear- or branched-alkylene radical having from 1 to 5 carbon atoms and $R_5$ denotes a pyridyl, phenyl, 2,3-methylenedioxyphenyl or 3,4-methylenedioxyphenyl radical or a phenyl group substituted with one or more substituents, which may be identical or different, selected from halogen atoms, lower alkyl groups or lower alkoxy groups, $R_4$ denotes hydrogen or an alkyl radical, or $R_3$ and $R_4$, when taken together, denote a 1,4-tetramethylene, 1,5-pentamethylene, 3-oxa-1,5-pentamethylene, 3-aza-1,5-pentamethylene, 3-methylaza-1,5-pentamethylene, 4-phenylaza-1,5-pentamethylene or —CH=CH—N=CH— radical, as well as a pharmaceutically acceptable salt of this compound.

2. An aminoalkoxyphenyl composition of formula:

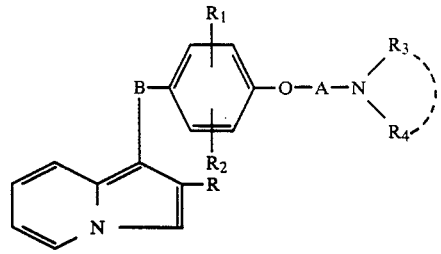

in which:

B represents a —S—, —SO— or —$SO_2$— group,

R denotes hydrogen or a methyl, ethyl, n-propyl, isopropyl, n-butyl, isobutyl, tert-butyl, 1-methylpropyl, n-pentyl, neopentyl, phenyl, monofluoro-, monochloro- or monobromophenyl, difluoro-, dichloro-, or dibromophenyl, monomethyl- or dimethylphenyl, monomethoxy or dimethoxyphenyl, or nitrophenyl radical or a methylphenyl radical substituted with a halogen atom, $R_1$ and $R_2$, which are identical or different, each denote hydrogen, chlorine, bromine or iodine or a methyl radical, A denotes a 1,2-ehtylene, 1,3- propylene, 2- methyl-1,3-propylene, 1,4-tetramethylene, 1,5- pentamethylene or 2-hydroxypropylene radical, $R_3$ denotes a methyl, ethyl, n-propyl, isopropyl, n-butyl, isobutyl, tert-butyl, 1-methylpropyl, n-pentyl, n-hexyl, n-heptyl, n-octyl, phenyl, benzyl, phenethyl, methoxyphenethyl, dimethoxyphenethyl, dimethylphenethyl, dimethoxyphenyl, dimethoxybenzyl or pyridyl ethyl radical or a phenethyl radical substituted in the aromatic portion with methyl and methoxy radicals, $R_4$ denotes hydrogen or a methyl, ethyl, n-propyl, isopropyl, n-butyl, iso-butyl, tert-butyl, n-pentyl, neopentyl, n-hexyl, n-heptyl or n-octyl radical, $R_3$ and $R_4$, when taken together, denote a 1,4-tetramethylene, 1,5-pentamethylene, 3-oxa-1,5-pentamethylene, 3-aza-1,5-pentamethylene, 3-methylaza-1,5-pentamethylene, 3-phenylaza-1,5-pentamethylene or —CH=CH—N=CH— radical, as well as a pharmaceutically acceptable salt of this compound.

3. An aminoalkoxyphenyl compound of formula:

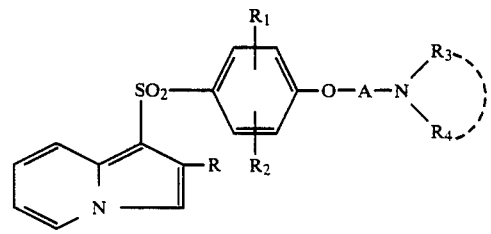

in which:

R denotes hydrogen, a linear- or branched-alkyl radical, a cycloalkyl radical containing at most 6 carbon atoms or a phenyl group which is unsubstituted or substituted with one or more substituents, which may be identical or different, selected from halogen atoms and from lower alkyl, lower alkoxy or nitro groups, $R_1$ and $R_2$, which are identical or different, each denote hydrogen, a methyl or ethyl radical or a halogen, A denotes a straight- or branched-alkylene radical having from 2 to 5 carbon atoms or a 2-hydroxypropylene radical in which the hydroxy is optionally substituted by a lower alkyl radical, $R_3$ denotes an alkyl radical $R_4$ denotes hydrogen or an alkyl radical, or $R_3$ and $R_4$, when taken together, denote a 1,4-tetramethylene, 1,5-pentamethylene, 3-oxa-1,5 pentamethylene, 3-aza-1,5-pentamethylene, 3-methylaza-1,5-pentamethylene, 3-phenylaza-1,5-pentamethylene or —CH=CH—N=CH— radical, as well as a pharmaceutically acceptable salt of this compound.

4. An aminoalkoxyphenyl compound of formula:

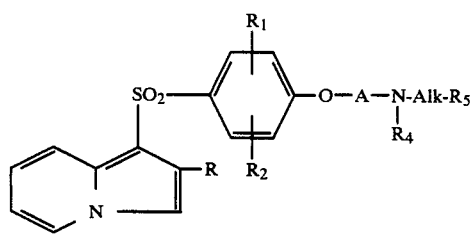

in which:

R denotes hydrogen, a linear- or branched-alkyl radical, a cycloalkyl radical containing at most 6 carbon atoms or a phenyl group which is unsubstituted or substituted with one or more substituents, which may be identical or different, selected from halogen atoms and from lower alkyl, lower alkoxy or nitro groups, $R_1$ and $R_2$, which are identical or different, each denote hydrogen, a methyl or ethyl radical or a halogen, A denotes a straight- or branched-alkylene radical having from 2 to 5 carbon atoms or a 2-hydroxypropylene radical in which the hydroxy is optionally substituted by a lower alkyl radical, Alk denotes a single bond or a linear- or branched-alkylene radical having from 1 to 5 carbon atoms, $R_5$ denotes a pyridyl, phenyl, 2,3-methylenedioxyphenyl or 3,4-methylenedioxyphenyl radical or a phenyl group substituted with one or more substituents, which may be identical or different, selected from halogen atoms, lower alkyl groups or lower alkoxy groups, $R_4$ denotes hydrogen or an alkyl radical, as well as pharmaceutically acceptable salts of this compound.

5. An aminoalkoxyphenyl compound according to claim 4 in which

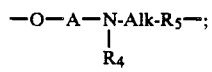

represents a [N-methyl-N-(3,4-dimethoxy-β-phenethyl)amino]propyloxy group.

6. An aminoalkoxyphenyl compound according to claim 4 in which R represents an isoproypl or cyclopropyl group.

7. An aminoalkoxyphenyl compound according to claim 4 which is 2-Isopropyl-1-[4{3-[N-methyl-N-(3,4-dimethoxy-β-phenethyl)amino]propyloxy}benzensulphonyl]-indolizine and pharmaceutically acceptable salts.

8. An aminoalkoxyphenyl compound according to claim 4 wherein the pharmaceutically acceptable salt is the oxalate or hydrochloride.

9. An aminoalkoxyphenyl compound according to claim 3 in which R represents an isopropyl or cyclopropyl group.

10. An aminoalkoxyphenyl compound according to claim 3 wherein the pharmaceutically acceptable salt is the oxalate or hydrochloride.

11. Apharamceutical or veterinary composition for use in the treatment of angina pectoris, hypertension and arrhythmia comprising an effective amount for treating angina pectoris, hypertension and arrhythmia of at least one indolizine compound according to claim 1.

12. A pharmaceutical or veterinary composition for use in the treatment of angine pectoris, hypertension and arrhythmia comprising an effective amount for treating angina pectoris, hypertension and arrhythmia of at least one indolizine compound according to claim 2.

13. A pharmaceutical or veterinary composition for use in the treatment comprising an effective amount for treating angina pectoris, hypertension and arrhythmia of at least one indolizine compound according to claim 3.

14. A pharmaceutical or veterinary composition for use in the treatment of angina pectoris, hypertension and arrhythmia comprising an effective amount for treating angine pectoris, hypertension and arrhythmia of at least one indolizine compound according to claim 4.

15. A method of treating angina pectoris, hypertension, arrhythmia and cerebral vascular insufficiency in a host in need of such treatment comprising the administration to this host of an effective dose of an aminoalkoxyphenyl derivative according to claim 1.

16. A method of treating angina pectoris, hypertension, arrhythmia and cerebral vascular insfficiency in a host in need of such treatment. comprising the administration to this host of an effective dose of an aminoalkoxyphenyl derivative according to claim 2.

17. A method of treating angina pectoris, hypertension, arrhythmia and cerebral vascular insufficiency in a host in need of such treatment comprising the administration to this host of an effective dose of an aminoalkoxyphenyl derivative according to claim 3.

18. A method of treating angina pectoris, hypertension, arrhythmia and cerebral vascular insufficiency in a host in need of such treatment comprising the administration to this host of an effective dose of an aminoalkoxyphenyl derivative according to claim 4.

19. An aminoalkoxyphenyl compound according to claim 1 wherein $R_3$ represents a 3,4-dimethoxyphenyl, 3,4-dimethoxybenzyl or 3,4-dimethoxyphenethyl radical.

20. An aminoalkoxyphenyl compound according to claim 2 wherein $R_3$ represents a 3,4-dimethoxyphenyl, 3,4-dimethoxybenzyl or 3,4-dimethoxyphenethyl radical.

21. An aminoalkoxyphenyl compound according to claim 1 wherein the pharmaceutically acceptable salt is the hydrochloride.

22. An aminoalkoxyphenyl compound according to claim 2 wherein the pharmaceutical acceptable salt is the hydrochloride.

23. A pharmaceutical or veterinary composition according to claim 11 for the treatment of angina pectoris, hypertension and arrhythmia containing from 50 mg to 500 mg of active principle.

24. A pharmaceutical or veterinary composition according to claim 12 for the treatment of angina pectoris, hypertension and arrhythmia, containing from 50 mg to 500 mg of active principle.

25. A pharmaceutical or veterinary composition according to claim 13 for the treatment of angina pectoris, hypertension and arrhythmia containing from 50 mg to 500 mg of active principle.

26. A pharmaceutical or veterinary composition according to claim 14 for the treatment of angina pectoris, hypertension and arrhythmia containing from 50 mg to 500 mg of active principle.

27. An aminoalkoxyphenyl compound according to claim 3 which is 2-Isopropyl-1[4-{3-[N-methyl-N-(3,4-dimethoxy-$\beta$-phenethyl)amino]propyloxy}benzenesulphonyl}indolizine and its pharmaceutically acceptable salts;

2-Isopropyl-1-{4-[3[3(di-n-butylamino)propyloxy]-benzenesulphonyl}indolizine and its pharmaceutically acceptable salts;

2-Ethyl-1-[4-{3-[N-methyl-N-(3,4-dimethoxy-$\beta$-phenethyl)amino]propyloxy}benzenesulphonyl]indolizine and its pharmaceutically acceptable salts; or 2-Ethyl-1-{4-[3-(di-n-butylamino)propyloxy]benzenesulphonyl}indolizine and its pharmaceutically acceptable salts.

28. 2-Isopropyl-1-[4-[3-[N-methyl-N-oxide-N-(3,4-dimethoxy-$\beta$-phenethyl)amino]propyloxy]-benzenesulphonyl]indolizine and pharmaceutically acceptable salts thereof.

* * * * *